United States Patent [19]

Arnold et al.

[11] Patent Number: 5,717,109

[45] Date of Patent: Feb. 10, 1998

[54] EXCITATORY AMINO ACID RECEPTOR ANTAGONISTS

[75] Inventors: M. Brian Arnold, Bargersville; Thomas J. Bleisch, Indianapolis; David R. Helton; Mary Jeanne Kallman, both of Greenfield; Paul L. Ornstein, Carmel; Darryle D. Schoepp, Indianapolis; Joseph P. Tizzano, New Palestine, all of Ind.

[73] Assignee: Eli Lilly and Company, Lilly Corporate Center, Ind.

[21] Appl. No.: 500,303

[22] Filed: Jul. 10, 1995

Related U.S. Application Data

[63] Continuation-in-part of Ser. No. 303,255, Sep. 8, 1994, abandoned.

[51] Int. Cl.[6] .................. A61K 31/19; C07C 101/20; C07D 209/04; C07D 333/22; C07D 31/80; C07C 229/00; C07C 207/00
[52] U.S. Cl. .................. 548/511; 514/454; 514/461; 514/514; 514/531; 514/538; 514/566; 548/319.1; 549/72; 549/390; 560/20; 560/36; 560/45; 560/46; 560/47; 562/433; 562/435; 562/441; 562/442; 562/444; 562/451; 562/456; 562/458
[58] Field of Search .................. 562/506, 433, 562/441, 442, 435, 444, 456, 451, 458; 548/319.1, 511; 540/316; 514/572, 566, 514, 454, 461, 538, 539; 560/20, 36, 45, 46, 47; 549/72, 390

[56] References Cited

U.S. PATENT DOCUMENTS

| | | | |
|---|---|---|---|
| 2,564,649 | 3/1951 | Rogers | 548/319.1 |
| 2,572,842 | 10/1951 | MacDonald | 562/575 |
| 2,824,132 | 2/1958 | Matzuk et al. | 548/319.1 |
| 3,547,948 | 12/1970 | Shen et al. | 548/319.1 |
| 3,636,098 | 1/1972 | Shima et al. | 522/575 |
| 4,061,542 | 12/1977 | Denmy et al. | 548/319.1 |
| 4,959,493 | 9/1990 | Ohfune et al. | 562/506 |
| 5,068,412 | 11/1991 | Ohfune et al. | 562/506 |
| 5,089,662 | 2/1992 | Wegner et al. | 562/506 |
| 5,177,109 | 1/1993 | Pelliciari et al. | 514/572 |

FOREIGN PATENT DOCUMENTS

| | | | |
|---|---|---|---|
| 94-06743 | 3/1994 | WIPO | 562/506 |
| WO 95/15940 | 6/1995 | WIPO | 562/506 |

OTHER PUBLICATIONS

Br. J. Pharmacol. (1994), 112, 809–816; Actions of two new antagonists showing selectivity for different subtypes of metabotropic glutamate receptor in the neonatal rat spinal cord. Jane et al.

Tetrahedron Letters, vol. 30, No. 29, pp. 3803–3804, 1989 New Routes to the Synthesis of CIS–α–(carboxycyclopropyl) glycines from 1–glutamic acid, conformationally restricted analogues of the excitatory neurotransmitter 1–glutamic acid (Shimamoto et al).

Tetrahedron Letters, vol. 29, No. 10, pp. 1181–1184, 1988 Synthesis of Trans–and CIS–α–(carboxycyclopropyl) glycines, novel neuroinhibitory amino acids as 1–glutamate analogue (Yamanoi et al).

Primary Examiner—Floyd D. Higel
Attorney, Agent, or Firm—Martin A. Hay; David E. Boone

[57] ABSTRACT

The present invention provides compounds of formula

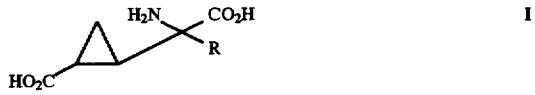

I in which R represents an organic group, or a pharmaceutically acceptable metabolically labile ester or amide thereof, or a pharmaceutically acceptable salt thereof, which are useful as antagonists of one or more of the actions of L-glutamate at metabotropic excitatory amino acid receptors.

14 Claims, No Drawings

EXCITATORY AMINO ACID RECEPTOR ANTAGONISTS

This application is a continuation-in-part of U.S. application Ser. No. 08/303,255 filed on Sep. 8th, 1994 (abandoned).

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Antagonists of these receptors are useful for the treatment of acute and chronic neurodegenerative conditions, and as antipsychotic, anticonvulsant, analgesic, anxiolytic, antidepressant, and anti-emetic agents.

SUMMARY OF THE INVENTION

The present invention provides a compound of formula

I in which R represents an organic group,
or a pharmaceutically acceptable metabolically labile ester or amide thereof,
or a pharmaceutically acceptable salt thereof. It also provides processes for preparing the compounds, pharmaceutical compositions containing the compounds and a method of antagonizing one or more of the actions of L-glutamate at metabotropic excitatory amino acid receptors using the compounds.

DETAILED DESCRIPTION OF THE INVENTION

The present invention provides a compound of formula

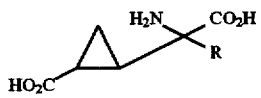

I in which
R represents an organic group.
The organic group represented by R may be a group of formula —L—Q in which
L represents a bond or a diradical of formula

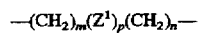

in which
m is 1 to 10;
p is 0 or 1;
n is 0 to 6; and
$Z^1$ is oxygen, sulphur or a group of formula $NR^a$ in which $R^a$ represents hydrogen, (1–6C)alkyl or phenyl(1–3C)alkyl; and Q is hydrogen, an optionally substituted heteroaromatic group, an optionally substituted aromatic group, a non-aromatic carbocyclic group, a non-aromatic heterocyclic group, or a non-aromatic monocyclic carbocyclic group fused with one or two monocyclic aromatic or heteroaromatic groups, a non-aromatic monocyclic heterocyclic group fused with one or two monocyclic aromatic or heteroaromatic groups; or a group of formula —$C(R^1R^2R^3)$ in which $R^1$ represents (1–6C)alkyl, an optionally substituted heteroaromatic group, an optionally substituted aromatic group, a non-aromatic carbocyclic group, a non-aromatic heterocyclic group, or a non-aromatic monocyclic carbocyclic group fused with one or two monocyclic aromatic or heteroaromatic groups, a non-aromatic monocyclic heterocyclic group fused with one or two monocyclic aromatic or heteroaromatic groups;
one or both of $R^2$ and $R^3$ is as defined for $R^1$ or represents a group of formula —$Z^2$—$R^4$ in which $Z^2$ represents a bond, O, S, $CH_2$ or —$NR^b$— in which $R^b$ represents hydrogen, (1–6C) alkyl or phenyl(1–3C)alkyl, and $R^4$ represents an optionally substituted heteroaromatic group or an optionally substituted aromatic group;
and the remainder of $R^2$ and $R^3$ represents hydrogen;
provided that when Q represents hydrogen, L does not represent a bond;

or a pharmaceutically acceptable metabolically labile ester or amide thereof;

or a pharmaceutically acceptable salt thereof.

In the compounds of formula I, the substituents on the cyclopropyl ring are in the trans configuration.

It will be appreciated that the compounds of formula I contain at least three asymmetric carbon atoms; two being in the cyclopropane ring and one being attached thereto. Accordingly, the compounds according to the invention may exist in and be isolated in the forms of two different diastereomeric pairs (each being a 1:1 mixture of two enantiomers) and four isomers. The S,S,S isomer is preferred.

As used herein, the term heteroaromatic group includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or a 5–6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, benzofuryl, benzothiophenyl, benzimidazolyl, benzoxazolyl, benzothiazolyl and indolyl.

The term aromatic group includes phenyl and a polycyclic aromatic carbocyclic ring such as naphthyl.

The term "optionally substituted", as used in the term "optionally substituted heteroaromatic or aromatic group", herein signifies that one or more substituents may be present, said substituents being selected from atoms and groups which, when present in the compound of formula I, do not prevent the compound of formula I from functioning as an antagonist of the action of L-glutamate at metabotropic glutamate receptors.

Examples of atoms and groups which may be present in an optionally substituted heteroaromatic or aromatic group are amino, hydroxy, nitro, halogeno, (1–6C) alkyl, (1–6C) alkoxy, (1–6C)alkylthio, carboxy, (1–6C) alkoxycarbonyl, carbamoyl, (1–6C) alkanoylamino, (1–6C)alkylsulphonyl, (1–6C) alkylsulphonylamino, optionally substituted phenyl, phenoxy, phenylthio, phenylsulphonyl, phenylsulphonylamino, toluenesulphonylamino, and (1–6C) fluoroalkyl. Examples of particular values are amino, hydroxy, fluoro, chloro, bromo, iodo, methyl, methoxy, methylthio, carboxy, acetylamino, methanesulphonyl, nitro, acetyl, phenoxy, phenylthio, phenylsulphonyl, methanesulphonylamino and trifluoromethyl.

Examples of values for an optionally substituted aromatic group are 1-naphthyl, 2-naphthyl, phenyl, 2-biphenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4-dichlorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl, and 4-carboxyphenyl.

The term "non-aromatic carbocyclic group" includes a monocyclic group, for example a (3–10C)cycloalkyl group, such as cyclopropyl, cyclobutyl, cyclopentyl, cyclohexyl, cycloheptyl, cyclooctyl, cyclononyl or cyclodecyl, and a fused polycyclic group such as 1-adamantyl or 2-adamantyl, 1-decalyl, 2-decalyl, 4a-decalyl, bicyclo[3.3.0]oct-1-yl, -2-yl or -3-yl, bicyclo[4.3.0]non-1-yl, -2-yl, -3-yl or -7-yl, bicyclo[5.3.0]dec-1-yl, -2-yl, -3-yl, -4-yl, -8-yl or -9-yl and bicyclo[3.3.1]non-1-yl,-2-yl,-3-yl or 9-yl.

The term "non-aromatic heterocyclic group" includes a 4 to 7 membered ring containing one or two heteroatoms selected from oxygen, sulphur and nitrogen, for example azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl.

The term "a non-aromatic monocyclic carbocyclic group fused with one or two monocyclic aromatic or heteroaromatic groups" includes a (3–10C)cycloalkyl group fused with a benzene ring or a an aromatic 5–6 membered ring containing from one to four heteroatoms selected from oxygen, sulfur and nitrogen, such as indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, -5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl.

The term "a non-aromatic monocyclic heterocyclic group fused with one or two monocyclic aromatic or heteroaromatic groups" includes a 4 to 7 membered ring containing one or two heteroatoms selected from oxygen, sulphur and nitrogen, fused with a benzene ring or a an aromatic 5–6 membered ring containing from one to four heteroatoms selected from oxygen, sulfur and nitrogen, such as 2,3-dihydrobenzopyran-2-yl, -3-yl or -4-yl, xanthen-9-yl, 1,2,3,4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl.

Unless specified otherwise, the term "alkyl" means a straight chain or branched alkyl group. Examples of values for a (1–6C)alkyl group include (1–4C)alkyl such as methyl, ethyl, propyl, isopropyl, butyl and isobutyl.

Particular values for m are 1, 2, 3, 4, 5, 6, 7, 8, 9 and 10. Preferably m is 1, 2, 3, 4, 5, or 6.

Particular values for n are 0, 1, 2, 3, 4, 5 and 6. Preferably n is 0.

Particular values for $Z^1$ are O, S and NH.

Examples of values for L are a bond, methylene, ethylene, propylene, butylene, pentylene and methyleneoxy.

Examples of values for Q when it represents an optionally substituted heteroaromatic group are 1-methylindol-3-yl, 2-thiophenyl and 3-thiophenyl.

Examples of values for Q when it represents an optionally substituted aromatic group are 1-naphthyl, 2-naphthyl, phenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4- dichlorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl and 4-carboxyphenyl.

Examples of values for Q when it represents a non-aromatic carbocyclic group are cyclobutyl, cyclopentyl, cyclohexyl, 1-adamantyl and bicyclo[3,3,1]non-9-yl.

An example of a value for Q when it represents a non-aromatic heterocyclic group is piperidin-4-yl.

An example of a value for Q when it represents a non-aromatic monocyclic carbocyclic group fused with one or two monocyclic aromatic or heteroaromatic groups is indanyl, for example indan-2-yl.

An example of a non-aromatic monocyclic heterocyclic group fused with one or two monocyclic aromatic or heteroaromatic groups is xanthen-9-yl (dibenzopyran-4-yl).

An example of a value for $R^1$ when it represents a (1–6C) alkyl group is methyl.

An example of a value for $R^1$ when it represents an optionally substituted aromatic group is phenyl.

Particular values for $R^2$ when it represents a group of formula —$Z^2$—$R^4$ are phenyl, benzyl, phenoxy, anilino or phenylthio.

Example of values for $R^2$ and $R^3$ are hydrogen and methyl.

Particular values for Q when it represents a group of formula —$C(R^1R^2R^3)$ are isopropyl, 1-phenylethyl, dibenzylmethyl, diphenylmethyl and di-(4-chlorophenyl) methyl.

When $R^1$ and $R^2$ each represents a (1–6C)alkyl group, particular values for $R^1$ and $R^2$ are methyl.

R preferably represents (dibenzopyran-4-yl)methyl, (2,2-diphenyl)ethyl, 2-(3-methylphenyl)ethyl, 2-(4-fluorophenyl)ethyl, 2-(3,5-dichlorophenyl)ethyl or 2-(3,4-difluorophenyl)ethyl.

Q preferably represents hydrogen; 1-methylindol-3-yl; 2-thiophenyl; 3-thiophenyl; naphth-1-yl; naphth-2-yl; phenyl which is unsubstituted or substituted by one or two of hydroxy, halogeno, (1–6C)alkyl, (1–6C)alkoxy, carboxy, phenyl, phenoxy or (1–6C)fluoroalkyl; pentafluorophenyl; cyclobutyl; cyclopentyl; cyclohexyl; 1-adamantyl; piperidin-4-yl; indan-2-yl; xanthen-9-yl; isopropyl; 1-phenylethyl; dibenzylmethyl or diphenylmethyl.

More preferably Q represents hydrogen, 1-methylindol-3-yl, 2-thiophenyl, 3-thiophenyl, 1-naphthyl, 2-naphthyl, phenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorphenyl, 2-chlorophenyl, 3-chlorophenyl, 4-chlorophenyl, 2,4-dichlorophenyl, 3,4-dichlorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl, 4-carboxyphenyl, cyclobutyl, cyclopentyl, cyclohexyl, 1-adamantyl, bicyclo[3,3,1]non-9-yl, piperidin-4-yl, indan-2-yl, xanthen-9-yl, isopropyl, 1-phenylethyl or diphenylmethyl.

More preferably Q represents 3-methylphenyl, diphenylmethyl, xanthen-9-yl, 4-fluorophenyl, 3,5-dichlorophenyl or 3,4-difluorophenyl.

Particularly preferred compounds according to the invention are those described in Examples 2, 3, 5, 15, 17, 18, 20, 21, 22, 23, 24, 25, 26, 27, 29, 30, 31, 32, 33, 34, 35, 36, 37, 38, 41, 44, 46, 47, 48, 50, 53, 54, 55, 56, 57, 58, 59, 60, 61, 62, 64, 68, 71, 72, 73, 75, 76, 77, 78, 79, 80, 81, 82 and 84 herein. The compounds of Examples 5, 21, 27, 29, 30, 35, 37, 38, 46, 48, 53, 54, 64, 68, 72, 75, 77, 78, 79 and 81 are more preferred. Of these, the compounds of Examples 64, 68 and 72 are especially preferred.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, naphthalene-2-sulfonate, mandelate, magnesium, tetramethylammonium, potassium, trimethylammonium, sodium, methylammonium, calcium, and the like salts.

Pharmaceutically acceptable metabolically labile ester and amide of compounds of formula I are ester or amide derivatives of compounds of formula I that are hydrolyzed in vivo to afford said compound of formula I and a pharmaceutically acceptable alcohol or amine. Examples of labile esters include ester formed with (1–6C) alkanol in which the alkanol moiety may be optionally substituted by a (1–8C) alkoxy group, for example methanol, ethanol, propanol and methoxyethanol. Example of metabolically labile amides include amides formed with amines such as methylamine.

According to another aspect, the present invention provides a process for the preparation of a compound of formula I, or a pharmaceutically acceptable metabolically labile ester or amide thereof, or a pharmaceutically acceptable salt thereof, which comprises (a) hydrolyzing a compound of formula

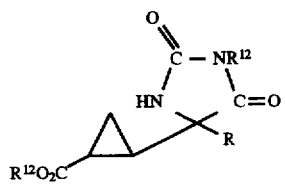

II or (b) deprotecting a compound of formula

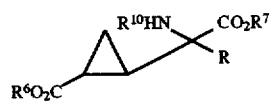

III in which $R^{12}$ represents hydrogen, a (1–4C)alkyl group, a phenyl (1–4C)alkyl group in which the phenyl group is unsubstituted or substituted by halogeno, (1–4C) alkyl or (1–4C)alkoxy, or a (3–4C)alkenyl group; one or both of $R^6$ and $R^7$ represents a carboxyl protecting group; and the remainder represents hydrogen; and $R^{10}$ represents hydrogen or an amine protecting group followed where necessary and/or desired by recovering one diastereomer or one isomer of said compound of formula I and/or forming a pharmaceutically acceptable metabolically labile ester or amide thereof and/or forming a pharmaceutically acceptable salt thereof.

The protection of carboxylic acid and amine groups, is generally described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups include acyl groups, such as groups of formula $R^{11}CO$ in which $R^{11}$ represents (1–6C) alkyl, (3–10C) cycloalkyl, phenyl(1–6C) alkyl, phenyl, (1–6C) alkoxy, phenyl(1–6C)alkoxy, or a (3–10C) cycloalkoxy, wherein a phenyl group may optionally be substituted by one or two substituents independently selected from amino, hydroxy, nitro, halogeno, (1–6C) alkyl, (1–6C) alkoxy, carboxy, (1–6C) alkoxycarbonyl, carbamoyl, (1–6C) alkanoylamino, (1–6C) alkylsulphonylamino, phenylsulphonylamino, toluenesulphonylamino, and (1–6C) fluoroalkyl.

The compounds of formula II are preferably hydrolyzed in the presence of a base, for example an alkali metal hydroxide such as lithium, sodium or potassium hydroxide, or an alkaline earth metal hydroxide such as barium hydroxide. The hydrolysis is conveniently performed in water in a closed vessel at a temperature in the range of from 150° to 300° C.

Particular values for $R^{12}$ are hydrogen, methyl, ethyl, n-propyl, n-butyl, benzyl, 4-methoxybenzyl, phenylethyl and phenylpropyl.

The compounds of formula III may be deprotected by a conventional method. Thus, an alkyl carboxyl protecting group may be removed by hydrolysis. The hydrolysis may conveniently be performed by heating the compound of formula III in the presence of either a base, for example an alkali metal hydroxide such as lithium, sodium or potassium hydroxide, or an alkaline metal hydroxide, such as barium hydroxide or an acid such as hydrochloric acid. The hydrolysis is conveniently performed at a temperature in the range of from 10° to 300° C. An aralkyl carboxyl protecting group may conveniently be removed by hydrogenation. The hydrogenation may conveniently be effected by reacting the compound of formula III with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° to 100° C.

An acyl, amine protecting group is also conveniently removed by hydrolysis, for example as described for the removal of an alkyl carboxyl protecting group.

The compounds of formula II in which may be prepared by reacting a compound of formula IV

IV in which $R^8$ represents a hydrogen atom or a (1–6C) alkyl group, with an alkali metal cyanide, such as lithium, sodium or potassium cyanide, and ammonium carbonate in an aqueous alcohol, such as aqueous ethanol. Conveniently the reaction is performed at a temperature in the range of from 35° to 150° C. If desired, the compounds of formula II may then be alkylated, for example using a compound of formula $R^{12}Cl$. As described in more detail hereinafter, the alkylated compounds are readily separated into their diastereomer.

The compounds of formula IV may be prepared by reacting a compound of formula V

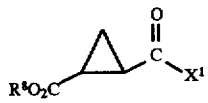

V in which $X^1$ represents a leaving atom or group and $R^8$ represents a (1–6C) alkyl, with an appropriate organometallic reagent, optionally in the presence of a palladium(0) or a palladium (II) catalyst.

Examples of appropriate organometallic reagents are organocadmium, organotin, organozinc and organocuprate reagents. An organozinc reagent may conveniently be formed by reacting a compound of formula RX in which X represents bromide or iodide with zinc/copper couple (formed, for example, from a 2% aqueous solution of copper(II) sulfate with zinc dust [Smith, *Org. Syn.* 1961, 41, 72]), or zinc foil (Gaudemar, *Bull. Soc. Chim. Fr.* 1962, 974) or activated zinc dust (prepared using a reagent such as 1,2-dibromoethane [Knochel, *J. Org. Chem.* 1988, 53, 2390] or chlorotrimethylsilane [Picotin, *J. Org. Chem.* 1987, 52, 4796]). An organotin reagent may be, for example, a compound of formula $(R^9)_3SnR$ in which $R^9$ represents a n-butyl group. An organocuprate reagent may be prepared by reacting a compound of formula RLi with a copper(I) salt such as copper(I) bromide.dimethyl sulfide, copper(I) iodide or copper(I) cyanide. The compound of formula RLi may be prepared by reacting a compound of formula RX in which X represents bromide or iodide with lithium metal doped with 1% sodium or by metal halogen exchange with either n-butyllithium or t-butyllithium.

When X is iodide, the compounds of formula RX are either commercially available or are readily prepared from the corresponding commercially available alcohol by using typical procedures known to one skilled in the art. For example, the alcohol can be converted to the corresponding mesylate with methanesulfonyl chloride or methane sulfonic anhydride with a base such as triethylamine in a solvent such as dichloromethane or ether, followed by reaction of the mesylate with sodium, potassium or lithium iodide in a solvent such as acetone. Alternatively, the alcohol can be converted to the iodide by treatment with triphenylphosphine, iodine and imidazole in a solvent such as dichloromethane or benzene; by treatment with iodotrimethylsilane in a solvent such as chloroform, acetonitrile or dichloromethane; or by treatment with chlorotrimethylsilane and sodium iodide in a solvent such as acetonitrile. In some cases, a carboxylic acid is commercially available, and this can be converted to the corresponding alcohol by treatment with a reducing agent such as borane or lithium aluminum hydride, in a solvent such as tetrahydrofuran or ether. In some cases, a carboxylic ester is commercially available, and this can be converted to the corresponding alcohol by treatment with a reducing agent such as lithium aluminum hydride, lithium borohydride or zinc borohydride in a solvent such as tetrahydrofuran or ether.

The leaving atom or group represented by $X^1$ may be, for example, a halogen atom such as a chlorine atom.

Palladium catalysis may be required for reactions of a compound of formula V with organozinc and organotin reagents. Examples of palladium catalysts include tetrakis (triphenylphosphine)palladium(0) and bis (triphenylphosphine)palladium(II) dichloride.

The reactions of a compound of formula V with an organometallic reagent are conveniently performed in an organic solvent such as benzene, toluene, tetrahydrofuran, ether, dioxane and 1,2-dimethoxyethane and at a temperature in the range of from −78° C. to the reflux temperature of the solvent.

Compounds of formula IV in which R represents a group —(CH$_2$)$_m$Q in which m is 2 to 10 and Q is as defined previously, may also be prepared by hydrogenating a compound of formula VII

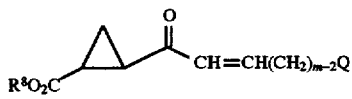
VII

The hydrogenation is conveniently performed in the presence of a palladium catalyst, such as palladium on charcoal, in an organic solvent such as ethanol.

The compounds of formula VII may be prepared by reacting a compound of formula VIII

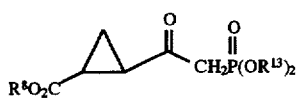
VIII in which $R^{13}$ represents a (1–4C) alkyl group, such as methyl with an aldehyde of formula

VIII in the presence of a strong base, such as sodium hydride or sodium bis(trimethylsilyl)amide. The reaction is conveniently performed in the presence of an organic solvent such as tetrahydrofuran at about ambient temperature.

The compounds of formula VIII may be prepared by reacting a (1–4C)dialkyl methylphosphonate, such as dimethyl methylphosphonate with a strong base, such as butyl lithium, and then copper (I) iodide, followed by a compound of formula V.

The compounds of formula III in which $R^7$ represents a hydrogen atom may be prepared by hydrolyzing a compound of formula VI

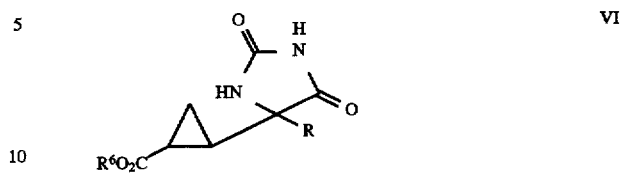

in which $R^6$ represents a carboxyl protecting group.

The hydrolysis may be performed according to the method of process (a) described herein above. It will be appreciated that the protecting group $R^6$ and/or the reaction conditions should be chosen such that the group $R^6$ is not removed.

Alternatively, the compounds of formula III may be prepared by reaction of a compound of formula I with an appropriate acyl halide or carbonyl chloride, in a solvent such as water, in the presence of a base such as sodium hydroxide, potassium carbonate, sodium bicarbonate or triethylamine. The corresponding substituted amine may then be reacted with a (1–6C) alkyl halide in the presence of a base such as potassium carbonate, sodium bicarbonate, triethylamine or di-i-propyl-N-ethylamine in a solvent such as dimethylformamide, dimethylsulfoxide or acetonitrile. Alternatively, compounds of formula III may be prepared by reaction of a compound of formula I with a (1–6C) alcohol, in the presence of an acid catalyst such as hydrogen chloride or sulfuric acid, or a dehydrating agent such as thionyl chloride. The derived diester may then be reacted with an acyl halide, a carbonyl chloride or a carboxylic acid that is activated with a reagent such as dicyclohexylcarbodiimide, N-hydroxysuccinimide, or i-butylchloroformate, in the presence of a base such as triethylamine, di-i-propyl-N-ethylamine, pyridine or 4-N,N-dimethylaminopyridine, in a solvent such as tetrahydrofuran or dichloromethane.

The compounds of formula V may be prepared by a method analogous to that described for the preparation of compounds of formula II, starting from a compound of formula IV of which $R^8$ represents an appropriate carboxyl protecting group.

When an isomer of a compound of formula I is desired, this may conveniently be prepared starting from an isomer of a compound of formula V. Thus, for example, di(1R,2S, 5R-methyl) 1S,2S-cyclopropane-1,2-dicarboxylate and di(1S,2R,5S-methyl) 1R,2R-cyclopropane-1,2-dicarboxylate may be prepared according to the method of K. Furuta, K. Iwanaga and H. Yamamoto, Organic Synthesis, 1988, 67, 76–85. These compounds may be partially hydrolyzed using aqueous sodium hydroxide in isopropyl alcohol, then reacted with thionyl chloride to afford, respectively, 1S,2S-2-(1R,2S,5R-carbomenthyloxy) cyclopropane-1-carbonyl chloride and 1R,2R-2-(1S,2R,5S carbomenthyloxy)cyclopropane-1-carbonyl chloride. The compound of formula V may then be converted into a compound of formula I by a method as described hereinabove, modified by incorporation of a step of separating the diastereomeric hydantoins. The diastereomeric hydantoins may be separated, for example, by chromatography, crystallisation or by reaction with a (1–4C) alkyl halide, a phenyl(1–4C)alkyl halide or a (3–4C)alkenyl halide, such as 4-methoxybenzyl chloride to afford a compound of formula II in which $R^{12}$ is (1–4C)alkyl, phenyl (1–4C)alkyl or (3–4C)alkenyl, followed by separating the resultant diastereomers by chromatography, and then removing the alkyl, phenylalkyl or alkyl groups, for example by reaction with ceric ammonium nitrate, or by direct hydrolysis of the hydantoin, such as by heating to about 200° C. in a sealed vessel in the presence of sodium hydroxide.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idopathic and drug-induced Parkinson's. The present invention also provides methods for treating these disorders which comprises administering to a patient in need thereof an effective amount of a compound of formula I or a pharmaceutically acceptable metabolically labile ester or amide thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester or amide thereof, or a pharmaceutically acceptable salt thereof.

Experiments were performed to demonstrate the ability of the formula I compounds to affect the excitatory amino acid receptors. The affinity for metabotropic glutamate receptors was demonstrated by the selective displacement of 1S,3R-ACPD-sensitive [³H]glutamate binding to rat brain cell membranes. The binding of [³H]glutamate was conducted with crude membranes of rat forebrain as described by Schoepp and True. Schoepp and True, *Neuroscience Lett.*, 145, 100–104 (1992) and True and Schoepp, *Society for Neuroscience Abstracts*, 19, 470 (1993). IC$_{50}$ values for the inhibition of [³H]glutamate binding, or the percent displacement of [³H]glutamate binding at a 10 μM concentration, of the formula I compound, is shown in Table II.

| Example #[a] | ACPD-Sensitive [³H]Glutamate Binding[b] IC$_{50}$ (μM) or (% Displacement at 10 μM) |
|---|---|
| 1 | (61%) |
| 2 | 0.32 |
| 3 | 0.63 |
| 4 | 2.3 |
| 5 | 0.076 |
| 6 | 7.1 |
| 7 | 7.0 |
| 8 | 6.2 |
| 9 | 2.2 |
| 10 | 2.1 |
| 11 | 1.4 |
| 12 | 1.8 |
| 13 | 1.7 |
| 14 | (17%) |
| 15 | 0.70 |
| 16 | 1.1 |
| 17 | 0.85 |
| 18 | 0.14 |
| 19 | 2.8 |
| 20 | 0.57 |
| 21 | 0.038[c] |
| 22 | 0.59 |
| 23 | 0.26 |
| 24 | 0.11 |
| 25 | 0.41 |
| 26 | 0.17[c] |
| 27 | 0.042 |
| 28 | 1.4 |
| 29 | 0.10 |
| 30 | 0.080 |
| 31 | 0.30 |
| 32 | 0.17 |
| 33 | 0.46 |
| 34 | 0.12 |
| 35 | 0.009 |
| 36 | 0.20 |
| 37 | 0.064 |
| 38 | 0.055 |
| 39 | 11.2[c] |
| 40 | 29.5 |
| 41 | 1.4 |
| 42 | (39%) |
| 43 | (32%) |
| 44 | 0.38 |
| 45 | (42%) |
| 46 | 0.077 |
| 47 | 0.22 |
| 48 | 0.038 |
| 49 | 1.5 |
| 50 | 0.37 |
| 51 | (15% @ 1 μM) |
| 52 | 4.9 |
| 53 | 0.095[c] |
| 54 | 0.023 |
| 55 | 0.12 |
| 56 | 0.61 |
| 57 | 0.48 |
| 58 | 0.58 |
| 59 | 0.21 |
| 60 | 0.17 |
| 61 | 0.28 |
| 62 | 0.23 |
| 63 (R,S,S) | 2.0[c] |
| 64 (S,S,S) | 0.035 ± 0.005[d] |
| 65 (R,R,R) | (45%) |
| 66 (S,R,R) | (36%) |
| 67 (R,S,S) | (22%)[b] |
| 68 (S,S,S) | 0.012 ± 0.003[d] |
| 69 (R,R,R) | (13%)[d] |
| 70 (R,R,R) | 8.1 |
| 71 (R,S,S) | 0.53 |
| 72 (S,S,S) | 0.014[c] |
| 73 (S,R,R) | 0.86[c] |
| 74 (R,R,R) | 4.2 |
| 75 | 0.025 |
| 76 | 0.51 |

-continued

| Example #[a] | ACPD-Sensitive [³H]Glutamate Binding[b] IC$_{50}$ (µM) or (% Displacement at 10 µM) |
|---|---|
| 77 | 0.060 |
| 78 | 0.037 |
| 79 | 0.049 |
| 80 | 0.37 |
| 81 | (57% @ 0.1 µM) |
| 82 | 0.68 |
| 83 | 2.6 |
| 84 | 0.36 |

[a]All compounds are a mixture of four stereoisomers (S,S,S; R,S,S; S,R,R; R,R,R; the first letter denotes stereochemistry at the amino acid carbon, and the next two letters denote stereochemistry at the cyclopropane carbons), unless otherwise noted.
[c]Average of two determinations.
[d]Average of three determinations.

Based on studies of receptor mediated changes in intracellar second messengers, metabotropic glutamate receptor are either coupled to enhanced phosphoinositide hydrolysis or decreases in forskolin-stimulated cAMP formation. Thus, mGluR antagonist activities of compounds may be determined by their ability to reverse mGluR agonist (1S,3R-ACPD, 100 µM)-evoked ³H-inositol phosphate formation in slices of the rat hippocampus as described by D. D. Schoepp et al., *Journal of Neurochemistry* 63: 769–772, 1994. Compounds may also be tested for ability to prevent inhibition of forskolin (30 µM)-stimulated cAMP formation by an mGluR agonist (1S,3R-ACPD, 20 µM) using slices of the rat hippocampus as described by D. D. Schoepp and B. G. Johnson, *Neurochemistry International* 22:277–283 (1993) and human mGluR2 expressing non-neuronal cells (D. D. Schoepp et al., *Neuropharmacology*, in press, 1995).

The antipsychotic activity of compounds according to the invention may be demonstrated using the well known conditional active avoidance model. This model was developed in the early 50s and 60s (Pfeiffer & Jenney, Ann. N.Y. Acad. Sci., 66: 293–246, 1957; Maffii, J. Pharm. Pharmacol., 11: 129–139, 1959; Cook & Weidley, Ann; N.Y. Acad. Sci., 66: 790–752, 1957; Janke, Handbook of Experimental Pharmacology, Vol. 55/I, New York: Plenum Press, 1978) and is still the primary model used to screen compounds for antipsychotic efficacy.

Rats were individually placed in a sound attenuated, two compartment test chamber. Active avoidance testing consisted of 20 trials each day. On each trial a light (130 v.) and a sound (85 dbA) were delivered simultaneously and 5 seconds later a 5 mA shock was delivered to the floor of the chamber. After 5 seconds the footshock, the light, and the sound were terminated. The animals learned to move from one side of the chamber to the other side when the light and sound cues were presented to avoid shock (avoidance responding) or the rat moved when the shock was administered (escape). Data were tabulated as mean percent escape or mean percent to avoidance for each test day. Prior to drug testing all animals were trained to successfully avoid shock delivery on 90% of trials.

Dosing of the compound of Example 72 at 0, 1, 3, 10 and 30 mg/kg. i.p. 20 minutes prior to testing produced a dose related decrease in avoidance responding while not affecting escape responding. This profile on conditioned avoidance is indicative of antipsychotic efficacy.

It is believed that the finding that the compound of Example 72 is active in the conditioned active avoidance model represents the first showing that compounds which are antagonists at metabotropic glutamate receptors are useful as antipsychotic agents.

According to another aspect, therefore, the present invention provides a method of treating psychosis, which comprises administering to a warm blooded mammal in need of treatment an effective amount of an antagonist which acts at metabotropic glutamate receptors.

The compounds of the present invention are preferably formulated prior to administration. Therefore, another aspect of the present invention is a pharmaceutical formulation comprising a compound of formula I in combination with one or more pharmaceutically-acceptable carriers, diluents, or excipients. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

| | Quantity (mg / capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| Active Ingredient | 100 mg |
| Mannitol | 100 mg |
| 5 N Sodium hydroxide | 200 μl |
| Purified water to total | 5 ml |

The following Examples further illustrate the compounds of the present invention and the methods for their synthesis. The Examples are not intended to be limiting to the scope of to use.

GENERAL EXPERIMENTAL

Benzene was dried by azeotropic distillation. Tetrahydrofuran was dried by distillation from sodium. All other solvents and reagents were used as obtained. Field desorption mass spectroscopy (FDMS) was performed using either a VG 70SE or a Varian MAT 731 instrument. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Elemental analyses for carbon, hydrogen and nitrogen were determined on a Control Equipment Corporation 440 Elemental Analyzer. "Chromatography" refers to flash chromatography (Still, W. C.; Kahn, M.; Mitra, A. *J. Org. Chem.* 1978, 43, 2923) on 230–400 mesh Silica Gel 60, using the amount of silica gel and solvent of elution referred to parenthetically in the text. "Cation exchange chromatography" refers to ion exchange with Dowex 50X-8 (100–200) resin ($H^+$ form). The resin was prepared by washing (in a coarse porosity sintered glass funnel) with water, then methanol, then water, then 3N ammonium hydroxide (pH≧12), then water, then 1N HCl (pH≦1), then water until the pH is neutral. The resin was packed into a glass column in water, and the compound (which is dissolved in water at a pH between 2 and 7) was slowly eluted onto the resin, then the column washed with water until the pH is neutral, then 50% aqueous THF, then water. The compound is eluted off of the resin with 10% aqueous pyridine, and product containing fractions (which are detected with ninhydrin stain on a TLC plate) are combined and concentrated in vacuo. This procedure is repeated two more times, and ensures complete removal of pyridine. "Anion exchange chromatography" refers to anion exchange with Bio-Rad AG1-X8 anion exchange resin (hydroxide form). The resin (obtained in acetate form) was prepared by washing (in a coarse porosity sintered glass funnel) with water, then methanol, then water, then twice with 1N sodium hydroxide (converts to the hydroxide form), then water until pH 7. The resin was packed into a glass column in water, and the compound (which is dissolved in water at a pH between 9 and 12) was slowly eluted onto the resin, then the column washed with water until the pH is neutral, then 50% aqueous THF, then water. The compound is eluted off of the resin with 3N aqueous acetic acid, and product containing fractions (which are detected with ninhydrin stain on a TLC plate) are combined and concentrated in vacuo.

PREPARATION 1

1SR,2SR-2-Carbethoxycyclopropane-1-carbonyl chloride

A 0° C. solution of 50 g (268 mmol) of diethyl 1SR,2SR-trans-cyclopropane-1,2-dicarboxylate and 54 mL (268 mmol) of 5N aqueous sodium hydroxide in 500 mL of ethanol was stirred 6 hr, then concentrated in vacuo. The residue was dissolved in 300 mL of water, washed twice with 200 mL each of ether, then the aqueous layer was acidified to pH 1 by the addition of concentrated hydrochloric acid. This solution was extracted four times with 200 mL each of ether, then the combined organic extracts were dried ($MgSO_4$), filtered and concentrated in vacuo. This residue was dissolved in 170 mL (277 g, 170 mmol) of thionyl chloride, stirred overnight at room temperature, then concentrated in vacuo to afford 32.5 g (69%) of the title compound.

PREPARATION 2

Typical procedure for the Preparation of an iodide from the corresponding alcohol: 1-Iodo-2,2-diphenylethane A solution of 19.8 g (75.7 mmol) of triphenylphosphine and 19.2 g (75.7 mmol) of iodine in 160 mL of dichloromethane was stirred 10 min at room temperature, then treated with 8.6 g (126 mmol) of imidazole, stirred an additional 10 min, then treated with 10 g (50.4 mmol) of 2,2-diphenylethanol in 30 mL of dichloromethane. After 1 hr more at room temperature, the mixture was washed with 160 mL of 10% aqueous sodium bisulfate, the organic layer was separated and the aqueous layer extracted three times with 100 mL each of ether. The combined organics were dried ($MgSO_4$), filtered and concentrated in vacuo. Chromatography of the residue (600 g of silica gel, 10% ethyl acetate/hexane) afforded 9.7 g (62%) of the title compound.

PREPARATION 3

Typical procedure for the Preparation of an alcohol from the corresponding carboxylic acid: 2-(2,5-dimethoxyphenyl)ethanol A 0° C. solution of 15 g (76 mmol) of 2,5-dimethoxyphenylacetic acid in 250 mL of tetrahydrofuran was treated dropwise with 15.3 mL of 10.0M borane methyl sulfide. After addition was complete, the mixture was stirred for 1 hr at 0° C. and 2 hr warming to room temperature. The reaction was quenched with 250 mL of saturated sodium bicarbonate, the organic layer was separated and the aqueous layer extracted four times with 70 mL each of ether. The combined organics were dried ($MgSO_4$), filtered and concentrated in vacuo to afford 13.1 g (95%) of the title compound.

PREPARATION 4

Dimethyl (1SR,2SR-2-carbethoxycycloprop-1-yl)-2-oxoethylphosphonate

To a −78° C. solution of 36.1 g (290.9 mmol) of dimethyl methylphosphonate in 560 mL of THF was added via cannulus 200 mL (320 mmol, 1.6M in hexane) of butyllithium. After 30 min at −78° C., 60.9 g (320 mmol) of copper(I) iodide was added, the mixture stirred for 1 hr at −45° C., then 56.5 g (320 mmol) of the material from Preparation 1 in 200 mL of THF was added at a moderate rate. After stirring for 2 hr more at −45° C., and at room temperature overnight, the reaction was quenched with 250 mL of 0.5M (in water) ethylene diamine tetraacetic acid (precipitate) followed by 250 mL of water and 600 mL of dichloromethane. The mixture was filtered through diatomaceous earth (0.75 inch layer in a 2 L sintered glass funnel), then the organic layer separated and the aqueous layer extracted twice with 300 mL each of dichloromethane. The combined organic extracts were dried ($MgSO_4$), filtered and concentrated in vacuo. Preparative HPLC afforded 33.1 g (39%) of the title compound.

PREPARATION 5

1S,2S-2-(1R,2S,5R-Carbomenthyloxy)cyclopropane-1-carbonyl chloride

A solution of 20 g (49.2 mmol) of di(1R,2S,5R-menthyl) 1S,2S-cyclopropane-1,2-dicarboxylate (K. Furuta, K. Iwanaga and H. Yamamoto, *Organic Synthesis*, 1988, 67, 76–85) and 10.8 mL (54.1 mmol) of 5N aqueous sodium hydroxide in 150 mL of isopropyl alcohol was stirred 18 hr at 55° C. , then concentrated in vacuo. The residue was dissolved in 150 mL of water, washed three times with 50 mL each of ether, then the aqueous layer was acidified to pH 1 by the addition of concentrated hydrochloric acid. This solution was extracted three times with 50 mL each of ether, then the combined organic extracts were dried ($MgSO_4$), filtered and concentrated in vacuo. This residue was dissolved in 100 mL (166 g, 1.4 mol) of thionyl chloride, stirred overnight at room temperature, then concentrated in vacuo to afford 10.9 g (94%) of the title compound.

PREPARATION 6

1R,2R-2-(1S,2R,5S Carbomenthyloxy)cyclopropane-1-carbonyl chloride

A solution of 18 g (44.3 mmol) of di(1S,2R,5S menthyl) 1R,2R-cyclopropane-1,2-dicarboxylate (K. Furuta, K. Iwanaga and H. Yamamoto, *Organic Synthesis*, 1988, 67, 76–85) and 9.8 mL (48.7 mmol) of 5N aqueous sodium hydroxide in 135 mL of isopropyl alcohol was stirred overnight at 70° C., then concentrated in vacuo. The residue was dissolved in 135 mL of water, washed three times with 50 mL each of ether, then the aqueous layer was acidified to pH 1 by the addition of 10% aqueous sodium bisulfate. This solution was extracted four times with 50 mL each of ethyl acetate, then the combined organic extracts were dried ($MgSO_4$), filtered and concentrated in vacuo. This residue was dissolved in 36 mL (58.7 g, 0.49 mol) of thionyl chloride, stirred overnight at room temperature, then concentrated in vacuo to afford 10.1 g (80%) of the title compound.

EXAMPLE 1

Preparation of 2SR- and 2RS-2-amino-2-(1SR, 2SR-2-carboxycyclopropan-1-yl)-3-phenylpropanoic acid A. (1SR,2SR-2-carbethoxycycloprop-1-yl) benzyl ketone: A 0° C. solution of 3.0 g (18 mmol) benzyl bromide and 1.8 g (27.6 mmol) of zinc/copper couple in 36 mL of benzene and 4 mL of N,N-dimethylacetamide was stirred for 3 hr, then treated with 0.5 g (0.5 mmol) of tetrakis (triphenylphosphine)palladium(0), 2.1 g (12 mmol) of the material from Preparation 1 and warmed to room temperature. After 30 min, the reaction was diluted with 40 mL of ethyl acetate and washed with 25 mL of 10% aqueous sodium bisulfate, 25 mL of saturated aqueous sodium bicarbonate and 25 mL of saturated aqueous sodium chloride. The organic layer was dried ($MgSO_4$), filtered and concentrated in vacuo. Chromatography (200 g of silica gel, 10% ethyl acetate/hexane) of the residue afforded 1.9 g (68%) of the title compound.

Analysis calculated for $C_{14}H_{16}O_3$: %C, 72.39; %H, 6.94. Found: %C, 72.30; %H, 6.74.

B. 5SR- and 5RS-5-(1SR,2SR-2-carboxycyclopropan-1-yl)-5-benzylimidazolidine-2,4-dione: A solution of 1.9 g (8 mmol) of the compound from Example 1A in 13 mL of ethanol was added to a solution of 1.3 g (20 mmol) of potassium cyanide and 2.8 g (36 mmol) of ammonium carbonate in 13 mL of water, then this mixture was placed in a 3.5×20 cm pressure tube, sealed with a #15 Teflon screw plug and heated to 90° C. for 24 hr. The mixture was cooled, vented, added to 100 mL of 10% aqueous sodium bisulfate and extracted three times with 40 mL each of ether. The combined organics were dried ($MgSO_4$), filtered and concentrated in vacuo to afford 2.2 g (100%) of the title compound.

C. A solution of 0.57 g (1.8 mmol) of the compound from Example 1B in 25 mL of 5N sodium hydroxide was placed in a 3.5×20 cm pressure tube, sealed with a #15 Teflon screw plug and heated to 125° C. for 24 hr. The mixture was cooled, vented, acidified to pH 4 with concentrated hydrochloric acid, then filtered and the precipitate washed three times with water. Cation exchange chromatography of the filtrate afforded a solid that was suspended in water and filtered, washed with water, acetone and ether and dried in vacuo at 60° C. to afford 0.073 g (16%) of the title compound.

Analysis calculated for $C_{13}H_{15}NO_4 \cdot 0.5\ H_2O$: %C, 60.46; %H, 6.24; %N, 5.42. Found: %C, 60.45; %H, 6.15; %N, 5.27.

Field Desorption Mass Spectrum: M+1=250.

EXAMPLE 2

Preparation of 2SR- and 2RS-2-amino-2-(1SR,2SR-2-carboxycyclopropan-1-yl)-4-phenylbutanoic acid A. (1SR,2SR-2-carbethoxycycloprop-1-yl) (2-(phenyl) eth-1-yl) ketone: A solution of 4.2 g (18 mmol) of (2-iodoethyl)benzene and 1.8 g (27.6 mmol) of zinc/copper couple in 40 mL of benzene and 4 mL of N,N-dimethylacetamide was stirred for 3 hr at 60° C., then treated with 0.5 g (0.5 mmol) of tetrakis(triphenylphosphine) palladium(0) and heated for 5 min more. The heating bath was removed, 2.1 g (12 mmol) of the material from Preparation 1 was added and the mixture stirred at room temperature for 1 hr. The mixture was diluted with 40 mL of ethyl acetate and filtered through diatomaceous earth. The filtrate was washed with 75 mL of 10% aqueous sodium bisulfate, 75 mL of saturated aqueous sodium bicarbonate and 75 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.0 g (68%) of the title compound.

Analysis calculated for $C_{15}H_{18}O_3$: %C, 73.15; %H, 7.37. Found: %C, 72.90; %H, 7.26.

B. 5SR- and 5RS-5-(1SR,2SR-2-carboxycyclopropan-1-yl)-5-(2-phenylethyl)imidazolidine-2,4-dione: A solution of 2.0 g (8 mmol) of the compound from Example 2A in 12 mL of ethanol was added to a solution of 1.3 g (20 mmol) of potassium cyanide and 2.8 g (36 mmol) of ammonium carbonate in 12 mL of water, then this mixture was placed in a 3.5×20 cm pressure tube, sealed with a #15 Teflon screw plug and heated to 90° C. for 24 hr. The mixture was cooled, vented, added to 100 mL of 10% aqueous sodium bisulfate and extracted three times with 40 mL each of ethyl acetate. The combined organics were dried ($MgSO_4$), filtered and concentrated in vacuo. This residue was dissolved in 50 mL of 1N sodium hydroxide and heated to reflux overnight, then cooled and acidified to pH 7. The resulting solid was filtered, washed with water and dried in vacuo at 60° C. to afford 2.0 g (94%) of the title compound.

C. A solution of 2.0 g (6.9 mmol) of the compound from Example 2B in 25 mL of 5N sodium hydroxide was placed in a 3.5×20 cm pressure tube, sealed with a #15 Teflon screw plug and heated to 125° C. for 24 hr. The mixture was cooled, vented, acidified to pH 7 with concentrated hydrochloric acid, then filtered and the precipitate washed three times with 10% pyridine/water. The filtrate was concentrated in vacuo, redissolved in water and again concentrated in vacuo. The redissolution in water and concentration in vacuo was repeated two more times. Cation exchange chromatography of the filtrate afforded a solid that was suspended in water and filtered, washed with water, acetone and ether and dried in vacuo at 60° C. to afford 0.88 g (48%) of the title compound.

Analysis calculated for $C_{14}H_{17}NO_4$: %C, 63.87; %H, 6.51; %N, 5.32. Found: %C, 63.80; %H, 6.37; %N, 5.49.

Field Desorption Mass Spectrum: M+1=264.

EXAMPLE 3

Preparation of 2SR- and 2RS-2-amino-2-(1SR,2SR-2-carboxycyclopropan-1-yl)-5-phenylpentanoic acid A. (1SR,2SR-2-carbethoxycycloprop-1-yl) (3-(phenyl) prop-1-yl) ketone: A solution of 5.6 g (22.6 mmol) of (3-iodoprop-1-yl)benzene and 1.8 g (27.6 mmol) of zinc/ copper couple in 40 mL of benzene and 4 mL of N,N-dimethylacetamide was stirred for 3 hr at 60° C., then treated with 0.5 g (0.5 mmol) of tetrakis(triphenylphosphine) palladium(0) and heated for 5 min more. The heating bath was removed, 2.1 g (12 mmol) of the material from Preparation 1 was added and the mixture stirred at room temperature for 1 hr. The mixture was diluted with 40 mL of ethyl acetate and filtered through diatomaceous earth. The filtrate was washed with 25 mL of 10% aqueous sodium bisulfate, 25 mL of saturated aqueous sodium bicarbonate and 25 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.7 g (86%) of the title compound.

B. (1SR,2SR-2-carboxycycloprop-1-yl) (3-(phenyl)prop-1-yl) ketone: A solution of 2.7 g (10.4 mmol) of the compound from Example 3A in 26 mL of ethanol and 11.4 mL of 1N sodium hydroxide was stirred overnight at room temperature, then concentrated in vacuo. The residue was dissolved in 10 mL of 1N sodium hydroxide, extracted twice with 20 mL each of ether, the aqueous layer was acidified to pH 1 with 10% sodium bisulfate and then extracted four times with 20 mL each of ether. The combined organics were dried (MgSO$_4$), filtered and concentrated in vacuo to afford 1.6 g (68%) of the title compound.

C. 5SR- and 5RS-5-(1SR,2SR-2-carboxycyclopropan-1-yl)-5-(3-phenylprop-1-yl)imidazolidine-2,4-dione: A solution of 1.6 g (6.9 mmol) of the compound from Example 3B in 12 mL of ethanol was added to a solution of 1.1 g (17.2 mmol) of potassium cyanide and 2.4 g (31 mmol) of ammonium carbonate in 12 mL of water, then this mixture was placed in a 3.5×20 cm pressure tube, sealed with a #15 Teflon screw plug and heated to 100° C. for 48 hr. The mixture was cooled, vented, and added to 100 mL of 10% aqueous sodium bisulfate. The resulting solid was filtered, washed with water and dried in vacuo at 60° C. to afford 1.7 g (80%) of the title compound.

D. A solution of 1.7 g (5.5 mmol) of the compound from Example 3C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of the residue afforded a solid that was suspended in water and filtered, washed with water, acetone and ether and dried in vacuo at 60° C. to afford 0.50 g (33%) of the title compound.

Analysis calculated for C$_{15}$H$_{19}$NO$_4$: %C, 64.97; %H, 6.91; %N, 5.05. Found: %C, 64.72; %H, 6.99; %N, 4.91.

Field Desorption Mass Spectrum: M=277.

EXAMPLE 4

Preparation of 2SR- and 2RS-2-amino-2-(1SR,2SR-2-carboxycyclopropan-1-yl)-6-phenylhexanoic acid A. (1SR,2SR-2-carbethoxycycloprop-1-yl) (4-(phenyl)but-1-yl) ketone: A solution of 4.6 g (18 mmol) of 1-iodo-4-phenylbutane and 1.8 g (27.6 mmol) of zinc/copper couple in 40 mL of benzene and 4 mL of N,N-dimethylacetamide was stirred for 3 hr at 60° C., then treated with 0.5 g (0.5 mmol) of tetrakis(triphenylphosphine)palladium(0) and heated for 5 min more. The heating bath was removed, 2.1 g (12 mmol) of the material from Preparation 1 was added and the mixture stirred at room temperature for 1 hr. The mixture was diluted with 40 mL of ethyl acetate and filtered through diatomaceous earth. The filtrate was washed with 25 mL of 10% aqueous sodium bisulfate, 25 mL of saturated aqueous sodium bicarbonate and 25 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.1 g (64%) of the title compound.

Analysis calculated for C$_{17}$H$_{22}$O$_3$: %C, 74.42; %H, 8.08. Found: %C, 74.67; %H, 8.06.

B. (1SR,2SR-2-carboxycycloprop-1-yl) (4-(phenyl)but-1-yl) ketone: A solution of 2.0 g (7.1 mmol) of the compound from Example 4A in 18 mL of ethanol and 7.8 mL of 1N sodium hydroxide was stirred overnight at room temperature, then concentrated in vacuo. The residue was dissolved in 10 mL of 1N sodium hydroxide, extracted twice with 20 mL each of ether, the aqueous layer was acidified to pH 1 with 10% sodium bisulfate and then extracted four times with 20 mL each of ether. The combined organics were dried (MgSO$_4$), filtered and concentrated in vacuo to afford 1.5 g (85%) of the title compound.

C. 5SR- and 5RS-5-(1SR,2SR-2-carboxycyclopropan-1-yl)-5-(4-phenylbut-1-yl)imidazolidine-2,4-dione: A solution of 1.5 g (6 mmol) of the compound from Example 4B in 10 mL of ethanol was added to a solution of 1.0 g (15 mmol) of potassium cyanide and 2.1 g (27 mmol) of ammonium carbonate in 10 mL of water, then this mixture was placed in a 3.5×20 cm pressure tube, sealed with a #15 Teflon screw plug and heated to 100° C. for 24 hr, at which time another 1.0 g portion of potassium cyanide and 2.1 g portion of ammonium carbonate were added and heating continued at 100° C. for another 24 hr. The mixture was cooled, vented, and added to 100 mL of 10% aqueous sodium bisulfate. The resulting solid was filtered, washed with water and dried in vacuo at 60° C. to afford 1.7 g (89%) of the title compound.

D. A solution of 1.7 g (5.4 mmol) of the compound from Example 4C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of the residue afforded a solid that was suspended in water and filtered, washed with water, acetone and ether and dried in vacuo at 60° C. to afford 0.72 g (45%) of the title compound.

Analysis calculated for C$_{16}$H$_{21}$NO$_4$: %C, 65.96; %H, 7.27; %N, 4.81. Found: %C, 65.70; %H, 7.24; %N, 4.72.

Field Desorption Mass Spectrum: M=291.

EXAMPLE 5

Preparation of 2SR- and 2RS-2-amino-2-(1SR,2SR-2-carboxycyclopropan-1-yl)-4,4-diphenylbutanoic acid A. (1SR,2SR-2-carbethoxycycloprop-1-yl) (2,2-(diphenyl)ethyl) ketone: A solution of 5.5 g (18 mmol) of 2,2-diphenyl-1-iodoethane and 1.8 g (27.6 mmol) of zinc/copper couple in 36 mL of benzene and 4 mL of N,N-dimethylacetamide was stirred for 3 hr at 60° C., then treated with 0.5 g (0.5 mmol) of tetrakis(triphenylphosphine) palladium(0) and heated for 5 min more. The heating bath was removed, 2.1 g (12 mmol) of the material from Preparation 1 was added and the mixture stirred at room temperature for 1 hr. The mixture was diluted with 40 mL of ethyl acetate and filtered through diatomaceous earth. The filtrate was washed with 25 mL of 10% aqueous sodium bisulfate, 25 mL of saturated aqueous sodium bicarbonate and 25 mL of saturated aqueous sodium chloride. The organic layer was dried (MgSO$_4$), filtered and concentrated in vacuo. Chromatography (200 g of silica gel, 20% ethyl acetate/hexane) of the residue afforded 3.4 g (88%) of the title compound.

Analysis calculated for C$_{21}$H$_{22}$O$_3$: %C, 78.23; %H, 6.88. Found: %C, 78.33; %H, 6.84.

B. (1SR,2SR-2-carboxycycloprop-1-yl) (2,2-(diphenyl)ethyl) ketone: A solution of 3.3 g (10.2 mmol) of the compound from Example 5A in 25 mL of ethanol and 11.2 mL of 1N sodium hydroxide was stirred overnight at room temperature, then concentrated in vacuo. The residue was dissolved in 10 mL of 10% sodium bisulfate and then extracted three times with 20 mL each of ether. The combined organics were dried (MgSO$_4$), filtered and concentrated in vacuo to afford 3.0 g (100%) of the title compound.

C. 5SR- and 5RS-5-(1SR,2SR-2-carboxycyclopropan-1-yl)-5-(2,2-(diphenyl)ethyl)imidazolidine-2,4-dione: A solution of 2.9 g (9.9 mmol) of the compound from Example 5B in 16 mL of ethanol was added to a solution of 1.6 g (24.7 mmol) of potassium cyanide and 3.5 g (44.5 mmol) of ammonium carbonate in 16 mL of water, then this mixture was placed in a 3.5×20 cm pressure tube, sealed with a #15 Teflon screw plug and heated to 90° C. for 48 hr. The mixture was cooled, vented, added to 100 mL of 10% aqueous sodium bisulfate and then extracted three times with 40 mL each of ether. The combined organics were dried (MgSO$_4$), filtered and concentrated in vacuo to afford 2.0 g (56%) of the title compound.

D. A solution of 2.0 g (5.5 mmol) of the compound from Example 5C in 25 mL of 5N sodium hydroxide was placed in a 3.5×20 cm pressure tube, sealed with a #15 Teflon screw plug and heated to 125° C. for 24 hr. The mixture was cooled and acidified to pH 7 with concentrated hydrochloric acid. The resulting solid was filtered and washed three times with 10 mL each of 10% pyridine/water. Recrystallization of the resulting solid from 1N hydrochloric acid and acetone afforded 1.4 g of a solid that was dissolved in 25 mL of 5N sodium hydroxide, placed in a 3.5×20 cm pressure tube, sealed with a #15 Teflon screw plug and heated to 125° C. for 24 hr. The mixture was cooled and acidified to pH 7 with concentrated hydrochloric acid. Cation exchange chromatography of this solution afforded a solid that was suspended in water and filtered, washed with water, acetone and ether and dried in vacuo at 60° C. to afford 0.67 g (35%) of the title compound.

Analysis calculated for $C_{20}H_{21}NO_4 \cdot 0.5\ H_2O$: %C, 68.95; %H, 6.36; %N, 4.02. Found: %C, 68.92; %H, 6.20; %N, 3.95.

Field Desorption Mass Spectrum: M=339.

EXAMPLE 6

Preparation of 2SR- and 2RS-2-amino-2-(1SR,2SR-2-carboxycyclopropan-1-yl)-5,5-diphenylpentanoic acid A. (1SR,2SR-2-carbethoxycycloprop-1-yl) (3,3-(diphenyl)prop-1-yl) ketone: A solution of 6 g (18 mmol) of 3,3-diphenyl-1-iodopropane and 1.8 g (27.6 mmol) of zinc/copper couple in 36 mL of benzene and 4 mL of N,N-dimethylacetamide was stirred for 1 hr at room temperature and 3 hr at 60° C., then treated with 0.5 g (0.5 mmol) of tetrakis(triphenylphosphine)palladium(0) and heated for 5 min more. The heating bath was removed, 2.1 g (12 mmol) of the material from Preparation 1 was added and the mixture stirred at room temperature for 1 hr. The mixture was diluted with 40 mL of ethyl acetate and filtered through diatomaceous earth. The filtrate was washed with 25 mL of 10% aqueous sodium bisulfate, 25 mL of saturated aqueous sodium bicarbonate and 25 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.1 g (77%) of the title compound.

Analysis calculated for $C_{22}H_{24}O_3$: %C, 78.54; %H, 7.19. Found: %C, 78.78; %H, 7.14.

B. 5SR- and 5RS-5-(1SR,2SR-2-carboxycyclopropan-1-yl)-5-(3,3-(diphenyl)prop-1-yl)imidazolidine-2,4-dione: A solution of 2.6 g (7.7 mmol) of the compound from Example 6A in 12 mL of ethanol was added to a solution of 1.2 g (19.2 mmol) of potassium cyanide and 2.7 g (34.6 mmol) of ammonium carbonate in 12 mL of water, then this mixture was placed in a 3.5×20 cm pressure tube, sealed with a #15 Teflon screw plug and heated to 50° C. for 72 hr and at 80° C. for 24 hr. The mixture was cooled and added to 100 mL of 10% aqueous sodium bisulfate and then extracted three times with 40 mL each of ethyl acetate. The combined organics were dried (MgSO$_4$), filtered and concentrated in vacuo. Chromatography (200 g of silica gel, 2% acetic acid/50% ethyl acetate/hexane) of the residue afforded 2.0 g (64%) of 5SR- and 5RS-5-(1SR,2SR-2-carbethoxycyclopropan-1-yl)-5-(3,3-(diphenyl)prop-1-yl)imidazolidine-2,4-dione and 1.0 g (34%) of the title compound.

C. A solution of 2.0 g (4.9 mmol) of 5SR- and 5RS-5-(1SR,2SR-2-carbethoxycyclopropan-1-yl)-5-(3,3-(diphenyl)prop-1-yl)imidazolidine-2,4-dione and 1.0 g (2.6 mmol) of the compound from Example 6C in 50 mL of 1N sodium hydroxide was heated to 100° C. for 24 hr, treated with an additional 25 mL of 1N NaOH, then stirred for 24 hr at reflux. The mixture was cooled and concentrated in vacuo. Anion exchange chromatography of the residue afforded 0.82 g (28%) of a solid that was determined to be mostly starting material. This material was heated to reflux for 48 hr in 10 mL of 5N sodium hydroxide, then cooled and acidified to pH 7 with concentrated hydrochloric acid. The residue was filtered, washing with water. Anion exchange chromatography of the filtrate afforded 0.34 g (12%) of a solid that was recrystallized from water and acetone to afford 0.21 g (8%) of the title compound.

Analysis calculated for $C_{21}H_{23}NO_4 \cdot 0.75\ H_2O$: %C, 68.74; %H, 6.73; %N, 3.82. Found: %C, 68.93; %H, 6.58; %N, 4.02.

Field Desorption Mass Spectrum: M=353.

EXAMPLE 7

Preparation of 2SR- and 2RS-2-amino-2-(1SR,2SR-2-carboxycyclopropan-1-yl)-6,6-diphenylhexanoic acid A. (1SR,2SR-2-carbethoxycycloprop-1-yl) (3,3-(diphenyl)prop-1-yl) ketone: A solution of 6 g (18 mmol) of 4,4-diphenyl-1-iodobutane and 1.8 g (27.6 mmol) of zinc/copper couple in 36 mL of benzene and 4 mL of N,N-dimethylacetamide was stirred for 3 hr at 60° C., then treated with 0.5 g (0.5 mmol) of tetrakis(triphenylphosphine) palladium(0) and heated for 5 min more. The heating bath was removed, 2.1 g (12 mmol) of the material from Preparation 1 was added and the mixture stirred at room temperature for 2 hr. The mixture was diluted with 40 mL of ethyl acetate, filtered through diatomaceous earth, and the filtrate concentrated in vacuo. Chromatography (200 g of silica gel, 20% ethyl acetate/hexane) of the residue afforded 3.1 g (73%) of the title compound.

Analysis calculated for $C_{23}H_{26}O_3 \cdot 0.35\ H_2O$: %C, 77.43; %H, 7.54. Found: %C, 77.40; %H, 7.50.

B. (1SR,2SR-2-carboxycycloprop-1-yl) (4,4-(diphenyl)but-1-yl) ketone: A solution of 3.0 g (8.6 mmol) of the compound from Example 7A in 19 mL of ethanol and 9.4 mL of 1N sodium hydroxide was stirred overnight at room temperature, then concentrated in vacuo. The residue was dissolved in 10 mL of 1N sodium hydroxide, extracted twice with 20 mL each of ether, the aqueous layer was acidified to pH 1 with 10% sodium bisulfate and then extracted four times with 20 mL each of ether. The combined organics were dried (MgSO$_4$), filtered and concentrated in vacuo to afford 2.7 g (100%) of the title compound.

C. 5SR- and 5RS-5-(1SR,2SR-2-carboxycyclopropan-1-yl)-5-(4,4-(diphenyl)but-1-yl)imidazolidine-2,4-dione: A solution of 2.7 g (8.3 mmol) of the compound from Example 7B in 14 mL of ethanol was added to a solution of 1.3 g (20.7 mmol) of potassium cyanide and 2.9 g (37.3 mmol) of ammonium carbonate in 14 mL of water, then this mixture was placed in a 3.5×20 cm pressure tube, sealed with a #15 Teflon screw plug and heated to 90° C. for 24 hr. The mixture was cooled, vented, added to 100 mL of 10% aqueous sodium bisulfate and then extracted three times with 40 mL each of ethyl acetate. The combined organics were dried (MgSO$_4$), filtered and concentrated in vacuo to afford 2.7 g (83%) of the title compound.

D. A solution of 2.7 g (6.9 mmol) of the compound from Example 7C in 25 mL of 5N sodium hydroxide was placed in a 3.5×20 cm pressure tube, sealed with a #15 Teflon screw plug and heated to 150° C. for 24 hr. The mixture was cooled and acidified to pH 4 with concentrated hydrochloric acid. The resulting solid was filtered and washed three times with 10 mL each of water, once with 10% pyridine/water and once again with water, then the filtrate concentrated in vacuo. Cation exchange chromatography of the residue afforded a solid that was suspended in water and filtered, washed with water, acetone and ether to afford 0.95 g (37%) of the title compound. A second crop was isolated from the filtrate and afforded 0.28 g (11%) of the title compound.

Analysis calculated for $C_{22}H_{25}NO_4 \cdot 0.5\ H_2O$: %C, 70.19; %H, 6.96; %N, 3.72. Found: %C, 69.75; %H, 6.63; %N, 3.99.

Field Desorption Mass Spectrum: M=367.

EXAMPLE 8

Preparation of 2SR- and 2RS-2-amino-2-(1SR,2SR-2-carboxycyclopropan-1-yl)propanoic acid A. (1SR,2SR-2-carbethoxycycloprop-1-yl) methyl ketone: To a 0° C. suspension of 4.7 g (24.8 mmol) of copper(I) iodide in 75 mL of THF was added 35.5 mL (49.7 mmol, 1.4M in ether) of methyl lithium. The mixture was cooled to –78° C., stirred for 30 min at that temperature, then treated with 4.0 g (22.6 mmol) of the material from Preparation 1 and stirred for an additional 1 hr. The reaction was quenched with 100 mL of saturated aqueous ammonium chloride, the organic layer separated and the aqueous layer extracted three times with 40 mL of ether. The combined organic layers were dried (MgSO$_4$), filtered and concentrated in vacuo. Chromatography (200 g of silica gel, 35% ethyl acetate/hexane) of the residue afforded 1.6 g (46%) of the title compound.

Analysis calculated for $C_8H_{12}O_3 \cdot 0.25\ H_2O$: %C, 59.80; %H, 7.84. Found: %C, 59.82; %H, 7.65.

B. (1SR,2SR-2-carboxycycloprop-1-yl) methyl ketone: A solution of 1.5 g (9.6 mmol) of the compound from Example 8A in 20 mL of ethanol and 10.6 mL of 1N sodium hydroxide was stirred at 50° C. for 2 hr, then concentrated in vacuo. The residue was dissolved in 20 mL of 1N hydrochloric acid and then extracted three times with 20 mL each of ethyl acetate. The combined organics were dried (MgSO$_4$), filtered and concentrated in vacuo to afford 1.2 g (100%) of the title compound.

C. 5SR- and 5RS-5-(1SR,2SR-2-carboxycyclopropan-1-yl)-5-methylimidazolidine-2,4-dione: A solution of 1.2 g (9.6 mmol) of the compound from Example 8B in 15 mL of ethanol was added to a solution of 3.1 g (48.0 mmol) of potassium cyanide and 6.7 g (86.4 mmol) of ammonium carbonate in 15 mL of water, then this mixture was heated to 50° C. for 24 hr. The mixture was cooled, added to 150 mL of 10% aqueous sodium bisulfate, then extracted three times with 100 mL each of ether, three times with 100 mL each of ethyl acetate and three times with 100 mL each of acetonitrile. The combined organics were dried (NaSO$_4$), filtered and concentrated in vacuo to afford 1.0 g (50%) of the title compound.

D. A solution of 3.9 g (10.6 mmol) of the compound from Example 8C and 7.3 g (23 mmol) of barium hydroxide in 20 mL of water was heated to 250° C. for 24 hr in a stainless steel high pressure reactor. The mixture was cooled and acidified to pH 7 with 1.3 mL (23 mmol) of concentrated sulfuric acid. The resulting solid was filtered and washed three times with 10 mL each of water. Cation exchange chromatography of the filtrate afforded a solid that was suspended in acetone and filtered, washed with acetone and ether and dried in vacuo at 60° C. to afford 0.28 g (35%) of the title compound.

Analysis calculated for $C_7H_{11}NO_4$: %C, 48.55; %H, 6.40; %N, 8.09. Found: %C, 48.69; %H, 6.41; %N, 7.96.

Field Desorption Mass Spectrum: M+1=174.

EXAMPLE 9

Preparation of 2SR- and 2RS-2-amino-2-(1SR,2SR-2-carboxycyclopropan-1-yl)butanoic acid A. (1SR,2SR-2-carbethoxycycloprop-1-yl) ethyl ketone: A solution of 5.1 g (33 mmol) of iodoethane and 3.3 g (50.6 mmol) of zinc/copper couple in 66 mL of benzene and 8 mL of N,N-dimethylacetamide was stirred for 3 hr at 50° C., then treated with 1.0 g (0.9 mmol) of tetrakis (triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.0 g (53%) of the title compound.

Analysis calculated for $C_9H_{14}O_3 \cdot 0.25\ H_2O$: %C, 61.87; %H, 8.37. Found: %C, 61.73; %H, 8.08.

B. (1SR,2SR-2-carboxycycloprop-1-yl) ethyl ketone: A solution of 1.9 g (11.2 mmol) of the compound from Example 9A in 28 mL of ethanol and 12.3 mL of 1N sodium hydroxide was stirred overnight at room temperature, then concentrated in vacuo. The residue was dissolved in 100 mL of 10% sodium bisulfate and extracted three times with 50 mL each of ether. The combined organics were dried (MgSO$_4$), filtered and concentrated in vacuo to afford 1.3 g (77%) of the title compound.

C. 5SR- and 5RS-5-(1SR,2SR-2-carboxycyclopropan-1-yl)-5-ethylimidazolidine-2,4-dione: A solution of 1.3 g (8.6 mmol) of the compound from Example 9B in 20 mL of ethanol was added to a solution of 1.4 g (21.5 mmol) of potassium cyanide and 3.0 g (38.6 mmol) of ammonium carbonate in 20 mL of water, then this mixture was placed in a 3.5×20 cm pressure tube, sealed with a #15 Teflon screw plug and heated to 100° C. for 24 hr. The mixture was cooled, vented, added to 150 mL of 10% aqueous sodium bisulfate and then extracted three times with 60 mL each of ether. The combined organics were dried (MgSO$_4$), filtered and concentrated in vacuo to afford 1.1 g (62%) of the title compound.

D. A solution of 1.1 g (5.3 mmol) of the compound from Example 9C in 25 mL of 5N sodium hydroxide was placed in a 3.5×20 cm pressure tube, sealed with a #15 Teflon screw plug and heated to 160° C. for 72 hr. The mixture was cooled and acidified to pH 7 with concentrated hydrochloric acid. The resulting solid was filtered and washed three times with 10% pyridine/water, then the filtrate concentrated in vacuo. Cation exchange chromatography of the residue afforded a solid that was suspended in water and filtered, washed with water, acetone and ether and dried in vacuo at 60° C. to afford 0.18 g (18%) of the title compound. Analysis calculated for C$_8$H$_{13}$NO$_4$: %C, 51.33; %H, 7.00; %N, 7.48. Found: %C, 51.05; %H, 6.88; %N, 7.45.

Field Desorption Mass Spectrum: M+1=188.

EXAMPLE 10

Preparation of 2SR- and 2RS-2-amino-2-(1SR,2SR-2-carboxycyclopropan-1-yl)pentanoic acid A. (1SR,2SR-2-carbethoxycycloprop-1-yl) n-propyl ketone: A solution of 6.0 g (33 mmol) of 1-iodopropane and 3.3 g (50.6 mmol) of zinc/copper couple in 66 mL of benzene and 8 mL of N,N-dimethylacetamide was stirred for 3 hr at 60° C., then treated with 1.0 g (0.9 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.9 g (73%) of the title compound.

B. (1SR,2SR-2-carboxycycloprop-1-yl) n-propyl ketone: A solution of 2.8 g (15.2 mmol) of the compound from Example 10A in 40 mL of ethanol and 16.7 mL of 1N sodium hydroxide was stirred overnight at room temperature, then concentrated in vacuo. The residue was dissolved in 100 mL of 10% sodium bisulfate and extracted three times with 50 mL each of ether. The combined organics were dried (MgSO$_4$), filtered and concentrated in vacuo to afford 2.1 g (87%) of the title compound.

C. 5SR- and 5RS-5-(1SR,2SR-2-carboxycyclopropan-1-yl)-5-n-propylimidazolidine-2,4-dione: A solution of 2.1 g (13.2 mmol) of the compound from Example 10B in 20 mL of ethanol was added to a solution of 2.1 g (33 mmol) of potassium cyanide and 4.6 g (59.3 mmol) of ammonium carbonate in 20 mL of water, then this mixture was placed in a 3.5×20 cm pressure tube, sealed with a #15 Teflon screw plug and heated to 100° C. for 24 hr. The mixture was cooled, vented, added to 100 mL of 10% aqueous sodium bisulfate and then extracted four times with 75 mL each of ether. The combined organics were dried (MgSO$_4$), filtered and concentrated in vacuo to afford 2.4 g (81%) of the title compound.

D. A solution of 2.4 g (10.7 mmol) of the compound from Example 10C in 30 mL of 5N sodium hydroxide was placed in a 3.5×20 cm pressure tube, sealed with a #15 Teflon screw plug and heated to 130° C. for 48 hr. The mixture was cooled and acidified to pH 7 with concentrated hydrochloric acid. The resulting solid was filtered and washed three times with 10% pyridine/water, then the filtrate concentrated in vacuo. Cation exchange chromatography of the residue afforded a solid that was suspended in water and filtered, washed with water, acetone and ether and dried in vacuo at 60° C. to afford 1.3 g (61%) of the title compound. Analysis calculated for C$_9$H$_{15}$NO$_4$: %C, 53.72; %H, 7.51; %N, 6.96. Found: %C, 53.46; %H, 7.50; %N, 6.97.

Field Desorption Mass Spectrum: M+1=202.

EXAMPLE 11

Preparation of 2SR- and 2RS-2-amino-2-(1SR,2SR-2-carboxycyclopropan-1-yl)hexanoic acid A. (1SR,2SR-2-carbethoxycycloprop-1-yl) n-butyl ketone: A solution of 6.0 g (33 mmol) of 1-iodobutane and 3.3 g (50.6 mmol) of zinc/copper couple in 66 mL of benzene and 8 mL of N,N-dimethylacetamide was stirred for 3 hr at 60° C., then treated with 1.0 g (0.9 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.2 g (73%) of the title compound.

Analysis calculated for C$_{11}$H$_{18}$O$_3$: %C, 66.64; %H, 9.15. Found: %C, 66.69; %H, 8.88.

B. (1SR,2SR-2-carboxycycloprop-1-yl) n-butyl ketone: A solution of 3.1 g (15.6 mmol) of the compound from Example 11A in 40 mL of ethanol and 17.2 mL of 1N sodium hydroxide was stirred overnight at room temperature, then concentrated in vacuo. The residue was dissolved in 100 mL of 10% sodium bisulfate and extracted three times with 50 mL each of ether. The combined organics were dried (MgSO$_4$), filtered and concentrated in vacuo to afford 2.4 g (90%) of the title compound.

C. 5SR- and 5RS-5-(1SR,2SR-2-carboxycyclopropan-1-yl)-5-n-butylimidazolidine-2,4-dione: A solution of 2.4 g (14 mmol) of the compound from Example 11B in 20 mL of ethanol was added to a solution of 2.3 g (35.1 mmol) of potassium cyanide and 5.0 g (63.2 mmol) of ammonium carbonate in 20 mL of water, then this mixture was placed in a 3.5×20 cm pressure tube, sealed with a #15 Teflon screw plug and heated to 100° C. for 24 hr. The mixture was cooled, vented, added to 100 mL of 10% aqueous sodium bisulfate and then extracted four times with 75 mL each of ether. The combined organics were dried (MgSO$_4$), filtered and concentrated in vacuo to afford 2.3 g (67%) of the title compound.

D. A solution of 2.3 g (9.4 mmol) of the compound from Example 11C in 30 mL of 5N sodium hydroxide was placed in a 3.5×20 cm pressure tube, sealed with a #15 Teflon screw plug and heated to 130° C. for 48 hr. The mixture was cooled and acidified to pH 7 with concentrated hydrochloric acid. The resulting solid was filtered and washed three times with 10% pyridine/water, then the filtrate concentrated in vacuo. Cation exchange chromatography of the residue afforded a solid that was suspended in water and filtered, washed with water, acetone and ether and dried in vacuo at 60° C. to afford 1.2 g (59%) of the title compound.

Analysis calculated for C$_{10}$H$_{17}$NO$_4$: %C, 55.80; %H, 7.96; %N, 6.51. Found: %C, 56.96; %H, 7.93; %N, 6.28.

Field Desorption Mass Spectrum: M+1=216.

EXAMPLE 12

Preparation of 2SR- and 2RS-2-amino-2-(1SR,2SR-2-carboxycyclopropan-1-yl)heptanoic acid A. (1SR,2SR-2-carbethoxycycloprop-1-yl) n-pentyl ketone: A solution of 6.5 g (33 mmol) of 1-iodobutane and 3.3 g (50.6 mmol) of zinc/copper couple in 66 mL of benzene and 8 mL of N,N-dimethylacetamide was stirred for 3 hr at 60° C., then treated with 1.0 g (0.9 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 10% ethyl acetate/hexane) of the residue afforded 4.0 g (86%) of the title compound.

B. (1SR,2SR-2-carboxycycloprop-1-yl) n-pentyl ketone: A solution of 3.9 g (18.4 mmol) of the compound from Example 12A in 45 mL of ethanol and 20.2 mL of 1N sodium hydroxide was stirred overnight at room temperature, then concentrated in vacuo. The residue was dissolved in 100 mL of 10% sodium bisulfate and extracted three times with 50 mL each of ether. The combined organics were dried ($MgSO_4$), filtered and concentrated in vacuo to afford 2.6 g (77%) of the title compound.

C. 5SR- and 5RS-5-(1SR,2SR-2-carboxycyclopropan-1-yl)-5-n-pentylimidazolidine-2,4-dione: A solution of 2.6 g (14.1 mmol) of the compound from Example 12B in 20 mL of ethanol was added to a solution of 2.3 g (35.1 mmol) of potassium cyanide and 5.0 g (63.2 mmol) of ammonium carbonate in 20 mL of water, then this mixture was placed in a 3.5×20 cm pressure tube, sealed with a #15 Teflon screw plug and heated to 100° C. for 24 hr. The mixture was cooled, vented, added to 100 mL of 10% aqueous sodium bisulfate and then extracted four times with 75 mL each of ether. The combined organics were dried ($MgSO_4$), filtered and concentrated in vacuo to afford 3.0 g (84%) of the title compound.

D. A solution of 3.0 g (11.8 mmol) of the compound from Example 12C in 30 mL of 5N sodium hydroxide was heated to 250° C. for 24 hr in a stainless steel high pressure reactor. The mixture was cooled and acidified to pH 7 with concentrated hydrochloric acid. The resulting solid was filtered and washed three times with 10% pyridine/water, then the filtrate concentrated in vacuo. Cation exchange chromatography of the residue afforded a solid that was suspended in water and filtered, washed with water, acetone and ether and dried in vacuo at 60° C. to afford 0.39 g (13%) of the title compound.

Analysis calculated for $C_{11}H_{19}NO_4 \cdot 0.3\ H_2O$: %C, 56.30; %H, 8.42; %N, 5.97. Found: %C, 55.99; %H, 8.04; %N, 6.52.

Field Desorption Mass Spectrum: M+1=230.

EXAMPLE 13

Preparation of 2SR- and 2RS-2-amino-2-(1SR,2SR-2-carboxycyclopropan-1-yl)decanoic acid A. (1SR,2SR-2-carbethoxycycloprop-1-yl) n-octyl ketone: A solution of 7.9 g (33 mmol) of 1-iodooctane and 3.3 g (50.6 mmol) of zinc/copper couple in 66 mL of benzene and 8 mL of N,N-dimethylacetamide was stirred for 3 hr at 60° C., then treated with 1.0 g (0.9 mmol) of tetrakis(triphenylphosphine) palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 10% ethyl acetate/hexane) of the residue afforded 4.9 g (88%) of the title compound.

Analysis calculated for $C_{15}H_{26}O_3$: %C, 70.83; %H, 10.30. Found: %C, 70.54; %H, 10.24.

B. (1SR,2SR-2-carboxycycloprop-1-yl) n-octyl ketone: A solution of 4.8 g (18.9 mmol) of the compound from Example 13A in 45 mL of ethanol and 20.7 mL of 1N sodium hydroxide was stirred overnight at room temperature, then concentrated in vacuo. The residue was dissolved in 100 mL of 10% sodium bisulfate and extracted three times with 50 mL each of ether. The combined organics were dried ($MgSO_4$), filtered and concentrated in vacuo to afford 3.1 g (72%) of the title compound.

C. 5SR- and 5RS-5-(1SR,2SR-2-carboxycyclopropan-1-yl)-5-n-octylimidazolidine-2,4-dione: A solution of 3.1 g (13.7 mmol) of the compound from Example 13B in 20 mL of ethanol was added to a solution of 2.2 g (34.2 mmol) of potassium cyanide and 4.8 g (61.6 mmol) of ammonium carbonate in 20 mL of water, then this mixture was placed in a 3.5×20 cm pressure tube, sealed with a #15 Teflon screw plug and heated to 100° C. for 24 hr. The mixture was cooled, vented, added to 150 mL of 10% aqueous sodium bisulfate and then extracted four times with 75 mL each of ether. The combined organics were dried ($MgSO_4$), filtered and concentrated in vacuo to afford 3.4 g (84%) of the title compound.

D. A solution of 3.4 g (11.5 mmol) of the compound from Example 13C in 25 mL of 5N sodium hydroxide was placed in a 3.5×20 cm pressure tube, sealed with a #15 Teflon screw plug and heated to 150° C. for 72 hr. The mixture was cooled and acidified to pH 7 with concentrated hydrochloric acid. The resulting solid was filtered and washed three times with 10% pyridine/water, then the filtrate concentrated in vacuo. Cation exchange chromatography of the residue afforded a solid that was suspended in water and filtered, washed with water, acetone and ether and dried in vacuo at 60° C. to afford 0.37 g (12%) of the title compound.

Analysis calculated for $C_{14}H_{25}NO_4$: %C, 61.97; %H, 9.29; %N, 5.16. Found: %C, 62.17; %H, 9.04; %N, 5.39.

Field Desorption Mass Spectrum: M+1=272.

EXAMPLE 14

Preparation of 2SR- and 2RS-2-amino-2-(1SR,2SR-2-carboxycyclopropan-1-yl)-3-methylbutanoic acid A. (1SR,2SR-2-carbethoxycycloprop-1-yl) (2-propyl) ketone: A solution of 5.6 g (33 mmol) of 2-iodopropane and 3.3 g (50.6 mmol) of zinc/copper couple in 66 mL of benzene and 8 mL of N,N-dimethylacetamide was stirred for 3 hr at 60° C., then treated with 1.0 g (0.9 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO₄), filtered and concentrated in vacuo. Chromatography (200 g of silica gel, 10% ethyl acetate/hexane) of the residue afforded 3.0 g (73%) of the title compound.

Analysis calculated for $C_{10}H_{16}O_3$: %C, 65.19; %H, 8.75. Found: %C, 65.15; %H, 8.51.

B. (1SR,2SR-2-carboxycycloprop-1-yl) (2-propyl) ketone: A solution of 2.8 g (15.2 mmol) of the compound from Example 14A in 33 mL of ethanol and 16.7 mL of 1N sodium hydroxide was stirred overnight at room temperature, then concentrated in vacuo. The residue was dissolved in 40 mL of water, extracted once with 25 mL of ether, the aqueous phase was brought to pH 2 with 50 mL of 10% sodium bisulfate and then extracted three times with 50 mL each of ether. The combined organics were dried (MgSO₄), filtered and concentrated in vacuo to afford 2.0 g (84%) of the title compound.

C. 5SR- and 5RS-5-(1SR,2SR-2-carboxycyclopropan-1-yl)-5-(1-methylethyl)imidazolidine-2,4-dione: A solution of 2.0 g (12.8 mmol) of the compound from Example 14B in 20 mL of ethanol was added to a solution of 2.1 g (32 mmol) of potassium cyanide and 4.5 g (57.6 mmol) of ammonium carbonate in 20 mL of water, then this mixture was placed in a 3.5×20 cm pressure tube, sealed with a #15 Teflon screw plug and heated to 90° C. for 24 hr. The mixture was cooled, vented, added to 150 mL of 10% aqueous sodium bisulfate and then extracted four times with 75 mL each of ether. The combined organics were dried (MgSO₄), filtered and concentrated in vacuo to afford 3.4 g (84%) of the title compound.

D. A solution of 2.2 g (9.7 mmol) of the compound from Example 14C in 50 mL of 1N sodium hydroxide was heated to reflux for 24 hr, then 25 mL of 5N sodium hydroxide was added and reflux continued for another 24 hr. The mixture was cooled and acidified to pH 7 with concentrated hydrochloric acid. The resulting solid was filtered and washed three times with water. Cation exchange chromatography of the filtrate afforded a solid that was suspended in water and filtered, washed with water, acetone and ether and dried in vacuo at 60° C. to afford 0.37 g (12%) of the title compound.

Analysis calculated for $C_9H_{15}NO_4 \cdot 0.75\ NH_4OH$: %C, 47.51; %H, 8.31; %N, 10.77. Found: %C, 47.10; %H, 7.82; %N, 10.50.

Field Desorption Mass Spectrum: M+1=202.

EXAMPLE 15

Preparation of 2SR- and 2RS-2-amino-2-(1SR,2SR-2-carboxycyclopropan-1-yl)-4-methylpentanoic acid A. (1SR,2SR-2-carbethoxycycloprop-1-yl) (2-methylpropyl) ketone: A solution of 6.0 g (33 mmol) of 1-iodo-2-methylpropane and 3.3 g (50.6 mmol) of zinc/copper couple in 66 mL of benzene and 8 mL of N,N-dimethylacetamide was stirred for 3 hr at 60° C., then treated with 1.0 g (0.9 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO₄), filtered and concentrated in vacuo. Chromatography (200 g of silica gel, 10% ethyl acetate/hexane) of the residue afforded 3.6 g (83%) of the title compound.

Analysis calculated for $C_{11}H_{18}O_3 \cdot 0.25\ H_2O$: %C, 65.16; %H, 9.20. Found: %C, 65.12; %H, 8.82.

B. (1SR,2SR-2-carboxycycloprop-1-yl) (2-methylpropyl) ketone: A solution of 3.6 g (18.1 mmol) of the compound from Example 15A in 40 mL of ethanol and 19.9 mL of 1N sodium hydroxide was stirred overnight at room temperature, then concentrated in vacuo. The residue was dissolved in 50 mL of 10% sodium bisulfate and then extracted three times with 25 mL each of ether. The combined organics were dried (MgSO₄), filtered and concentrated in vacuo to afford 2.3 g (73%) of the title compound.

C. 5SR- and 5RS-5-(1SR,2SR-2-carboxycyclopropan-1-yl)-5-(2-methylpropyl)imidazolidine-2,4-dione: A solution of 2.3 g (13.2 mmol) of the compound from Example 15B in 22 mL of ethanol was added to a solution of 2.1 g (33 mmol) of potassium cyanide and 4.6 g (59.5 mmol) of ammonium carbonate in 22 mL of water, then this mixture was placed in a 3.5×20 cm pressure tube, sealed with a #15 Teflon screw plug and heated to 90° C. for 48 hr. The mixture was cooled, vented, added to 150 mL of 10% aqueous sodium bisulfate and then extracted four times with 75 mL each of ether. The combined organics were dried (MgSO₄), filtered and concentrated in vacuo to afford 2.2 g (77%) of the title compound.

D. A solution of 2.2 g (8.2 mmol) of the compound from Example 15C in 30 mL of 5N sodium hydroxide was placed in a 3.5×20 cm pressure tube, sealed with a #15 Teflon screw plug and heated to 100° C. for 24 hr. The mixture was cooled and acidified to pH 4 with concentrated hydrochloric acid. The resulting solid was filtered and washed three times with water. Cation exchange chromatography of the filtrate afforded a solid that was suspended in water and filtered, washed with water, acetone and ether and dried in vacuo at 60° C. to afford 0.34 g (19%) of the title compound.

Analysis calculated for $C_{10}H_{17}NO_4$: %C, 55.80; %H, 7.96; %N, 6.51. Found: %C, 55.57; %H, 8.03; %N, 6.50.

Field Desorption Mass Spectrum: M+1=216.

EXAMPLE 16

Preparation of 2SR- and 2RS-2-amino-2-(1SR,2SR-2-carboxycyclopropan-1-yl)-5-methylhexanoic acid A. (1SR,2SR-2-carbethoxycycloprop-1-yl) (3-methylbutyl) ketone: A solution of 5.3 g (26.8 mmol) of 1-iodo-3-methylbutane and 2.6 g (41.0 mmol) of zinc/copper couple in 66 mL of benzene and 8 mL of N,N-dimethylacetamide was stirred for 3 hr at 60° C., then treated with 0.8 g (0.7 mmol) of tetrakis(triphenylphosphine)palladium(0) and heated for 5 min more. The heating bath was removed, 3.1 g (17.8 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO₄), filtered and concentrated in vacuo. Chromatography (200 g of silica gel, 10% ethyl acetate/hexane) of the residue afforded 3.0 g (79%) of the title compound.

B. (1SR,2SR-2-carboxycycloprop-1-yl) (3-methylbutyl) ketone: A solution of 2.6 g (12.3 mmol) of the compound from Example 16A in 27 mL of ethanol and 13.5 mL of 1N sodium hydroxide was stirred overnight at room temperature, then concentrated in vacuo. The residue was dissolved in 40 mL of water, extracted twice with 25 mL of ether, the aqueous phase was brought to pH 2 with concentrated hydrochloric acid and then extracted four times with 50 mL each of ether. The combined organics were dried (MgSO$_4$), filtered and concentrated in vacuo to afford 1.8 g (81%) of the title compound.

C. 5SR- and 5RS-5-(1SR,2SR-2-carboxycyclopropan-1-yl)-5-(3-methylbutyl)imidazolidine-2,4-dione: A solution of 1.9 g (10.3 mmol) of the compound from Example 16B in 17 mL of ethanol was added to a solution of 1.7 g (25.8 mmol) of potassium cyanide and 3.6 g (46.4 mmol) of ammonium carbonate in 17 mL of water, then this mixture was placed in a 3.5×20 cm pressure tube, sealed with a #15 Teflon screw plug and heated to 150° C. for 24 hr. The mixture was cooled, vented, added to 200 mL of 10% aqueous sodium bisulfate and then extracted four times with 75 mL each of ether. The combined organics were dried (MgSO$_4$), filtered and concentrated in vacuo to afford 2.3 g (88%) of the title compound.

D. A solution of 2.3 g (9.0 mmol) of the compound from Example 16C in 30 mL of 5N sodium hydroxide was heated to 250° C. for 24 hr in a stainless steel high pressure reactor. The mixture was cooled and acidified to pH 7 with concentrated hydrochloric acid. Cation exchange chromatography of this material afforded a solid that was suspended in water and filtered, washed with water, acetone and ether and dried in vacuo at 60° C. to afford 0.36 g (13%) of the title compound.

Analysis calculated for $C_{11}H_{19}NO_4$: %C, 57.63; %H, 8.35; %N, 6.11. Found: %C, 57.50; %H, 8.29; %N, 6.10.

Field Desorption Mass Spectrum: M+1=230.

EXAMPLE 17

Preparation of 2SR- and 2RS-2-amino-2-(1SR,2SR-2-carboxycyclopropan-1-yl)-6-methylheptanoic acid A. (1SR,2SR-2-carbethoxycycloprop-1-yl) (4-methylpentyl) ketone: A solution of 4.9 g (23 mmol) of 1-iodo-4-methylpentane and 2.2 g (35.2 mmol) of zinc/copper couple in 66 mL of benzene and 8 mL of N,N-dimethylacetamide was stirred for 3 hr at 60° C., then treated with 0.7 g (0.6 mmol) of tetrakis(triphenylphosphine) palladium(0) and heated for 5 min more. The heating bath was removed, 2.7 g (15.3 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.0 g (58%) of the title compound.

Analysis calculated for $C_{13}H_{22}O_3$.0.25 $H_2O$: %C, 67.65; %H, 9.83. Found: %C, 68.06; %H, 9.60.

B. (1SR,2SR-2-carboxycycloprop-1-yl) (4-methylpentyl) ketone: A solution of 1.9 g (8.4 mmol) of the compound from Example 17A in 19 mL of ethanol and 9.2 mL of 1N sodium hydroxide was stirred overnight at room temperature, then concentrated in vacuo. The residue was dissolved in 40 mL of water, extracted twice with 25 mL of ether, the aqueous phase was brought to pH 2 with concentrated hydrochloric acid and then extracted three times with 50 mL each of ether. The combined organics were dried (MgSO$_4$), filtered and concentrated in vacuo to afford 1.5 g (88%) of the title compound.

C. 5SR- and 5RS-5-(1SR,2SR-2-carboxycyclopropan-1-yl)-5-(4-methylpentyl)imidazolidine-2,4-dione: A solution of 1.5 g (7.4 mmol) of the compound from Example 17B in 12 mL of ethanol was added to a solution of 1.2 g (18.4 mmol) of potassium cyanide and 2.6 g (33.1 mmol) of ammonium carbonate in 12 mL of water, then this mixture was placed in a 3.5×20 cm pressure tube, sealed with a #15 Teflon screw plug and heated to 150° C. for 24 hr. The mixture was cooled, vented, added to 200 mL of 10% aqueous sodium bisulfate and then extracted four times with 75 mL each of ether. The combined organics were dried (MgSO$_4$), filtered and concentrated in vacuo to afford 1.7 g (84%) of the title compound.

D. A solution of 1.7 g (6 mmol) of the compound from Example 17C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of this material afforded a solid that was suspended in water and filtered, washed with water, acetone and ether and dried in vacuo at 60° C. to afford 0.85 g (58%) of the title compound.

Analysis calculated for $C_{12}H_{21}NO_4$.0.5 $H_2O$: %C, 57.12; %H, 8.79; %N, 5.55. Found: %C, 57.53; %H, 8.44; %N, 5.88.

Field Desorption Mass Spectrum: M+1=244.

EXAMPLE 18

Preparation of 2SR- and 2RS-2-amino-2-(1SR,2SR-2-carboxycyclopropan-1-yl )-4-(naphth-1-yl) butanoic acid A. (1SR,2SR-2-carbethoxycycloprop-1-yl) (2-(naphth-1-yl)ethyl) ketone: A solution of 5.7 g (20.2 mmol) of 1-iodo-2-(naphth-1-yl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis(triphenylphosphine) palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.0 g (75%) of the title compound.

Analysis calculated for $C_{19}H_{20}O_3$: %C, 77.00; %H, 6.80. Found: %C, 76.93; %H, 7.03.

B. (1SR,2SR-2-carboxycycloprop-1-yl) (2-(naphth-1-yl) ethyl) ketone: A solution of 2.9 g (9.8 mmol) of the compound from Example 18A in 22 mL of ethanol and 10.8 mL of 1N sodium hydroxide was stirred overnight at room temperature, then concentrated in vacuo. The residue was dissolved in 40 mL of water, brought to pH 2 with concentrated hydrochloric acid, and the resulting solid was filtered, washed three times with 10 mL each of water, then dried in vacuo at 60° C. to afford 2.5 g (96%) of the title compound.

C. 5SR- and 5RS-5-(1SR,2SR-2-carboxycyclopropan-1-yl)-5-(2-(naphth-1-yl)ethyl)imidazolidine-2,4-dione: A solution of 2.5 g (9.4 mmol) of the compound from Example 18B in 15 mL of ethanol was added to a solution of 1.5 g (23.6 mmol) of potassium cyanide and 3.3 g (42.4 mmol) of ammonium carbonate in 12 mL of water, then this mixture was placed in a 3.5×20 cm pressure tube, sealed with a #15 Teflon screw plug and heated to 150° C. for 24 hr. The mixture was cooled, vented, added to 200 mL of 10% aqueous sodium bisulfate and then extracted four times with 75 mL each of ether. The product precipitated from the ether and was filtered, washed with ether and dried in vacuo to afford 1.4 g (44%) of the title compound.

D. A solution of 1.4 g (4.1 mmol) of the compound from Example 18C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of this material afforded a solid that was suspended in water and filtered, washed with water, acetone and ether and dried in vacuo at 60° C. to afford 0.66 g (51%) of the title compound.

Analysis calculated for $C_{18}H_{19}NO_4$: %C, 69.00; %H, 6.11; %N, 4.47. Found: %C, 69.84; %H, 6.29; %N, 4.04.

Field Desorption Mass Spectrum: M=313.

EXAMPLE 19

Preparation of 2SR- and 2RS-2-amino-2-(1SR,2SR-2-carboxycyclopropan-1-yl)-4-(naphth-2-yl)butanoic acid A. (1SR,2SR-2-carbethoxycycloprop-1-yl) (2-(naphth-2-yl)ethyl) ketone: A solution of 5.7 g (20.2 mmol) of 1-iodo-2-(naphth-2-yl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.2 g (80%) of the title compound.

Analysis calculated for $C_{19}H_{20}O_3$: %C, 77.00; %H, 6.80. Found: %C, 76.76; %H, 6.71.

B. (1SR,2SR-2-carboxycycloprop-1-yl) (2-(naphth-1-yl)ethyl) ketone: A solution of 3.2 g (10.8 mmol) of the compound from Example 19A in 24 mL of ethanol and 11.9 mL of 1N sodium hydroxide was stirred overnight at room temperature, then concentrated in vacuo. The residue was dissolved in 25 mL of water, extracted once with 25 mL of ether, then brought to pH 2 with concentrated hydrochloric acid. The resulting solid was filtered, washed three times with 10 mL each of water, then dried in vacuo at 60° C. to afford 2.4 g (83%) of the title compound.

C. 5SR- and 5RS-5-(1SR,2SR-2-carboxycyclopropan-1-yl)-5-(2-(naphth-2-yl)ethyl)imidazolidine-2,4-dione: A solution of 2.4 g (8.9 mmol) of the compound from Example 19B in 15 mL of ethanol was added to a solution of 1.5 g (23.6 mmol) of potassium cyanide and 3.1 g (40.2 mmol) of ammonium carbonate in 12 mL of water, then this mixture was placed in a 3.5×20 cm pressure tube, sealed with a #15 Teflon screw plug and heated to 120° C. for 24 hr. The mixture was cooled, vented, added to 150 mL of 10% aqueous sodium bisulfate, and the resulting precipitate was filtered, washed three times with water and dried in vacuo at 60° C. to afford 2.9 g (97%) of the title compound.

D. A solution of 2.9 g (8.6 mmol) of the compound from Example 19C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of this material afforded a solid that was suspended in water and filtered, washed with water, acetone and ether and dried in vacuo at 60° C. to afford 1.5 g (54%) of the title compound.

Analysis calculated for $C_{18}H_{19}NO_4$: %C, 69.00; %H, 6.11; %N, 4.47. Found: %C, 68.70; %H, 6.11; %N, 4.34.

Field Desorption Mass Spectrum: M=313.

EXAMPLE 20

Preparation of 2SR- and 2RS-2-amino-2-(1SR,2SR-2-carboxycyclopropan-1-yl)-4-(2-methylphenyl)butanoic acid A. (1SR,2SR-2-carbethoxycycloprop-1-yl) (2-(2-methylphenyl)ethyl) ketone: A solution of 5.0 g (20.2 mmol) of 1-iodo-2-(2-methylphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.4 g (97%) of the title compound.

B. (1SR,2SR-2-carboxycycloprop-1-yl) (2-(2-methylphenyl)ethyl) ketone: A solution of 3.4 g (13.0 mmol) of the compound from Example 20A in 29 mL of ethanol and 14.3 mL of 1N sodium hydroxide was stirred overnight at room temperature, then concentrated in vacuo. The residue was dissolved in 25 mL of water, brought to pH 2 with concentrated hydrochloric acid. The resulting solution was extracted three times with 25 mL each of ether, then the combined organics were dried (MgSO$_4$), filtered and concentrated in vacuo at 60° C. to afford 2.5 g (83%) of the title compound.

C. 5SR- and 5RS-5-(1SR,2SR-2-carboxycyclopropan-1-yl)-5-(2-(2-methylphenyl)ethyl)imidazolidine-2,4-dione: A solution of 2.4 g (10.4 mmol) of the compound from Example 20B in 17 mL of ethanol was added to a solution of 1.7 g (26.0 mmol) of potassium cyanide and 3.7 g (47 mmol) of ammonium carbonate in 17 mL of water, then this mixture was placed in a 3.5×20 cm pressure tube, sealed with a #15 Teflon screw plug and heated to 120° C. for 24 hr. The mixture was cooled, vented, added to 150 mL of 10% aqueous sodium bisulfate, and the resulting precipitate was filtered and washed three times with water. Recrystallization from acetone/water afforded 2.5 g (83%) of the title compound.

D. A solution of 1.2 g (4.1 mmol) of the compound from Example 20C in 25 mL of 5N sodium hydroxide was heated to 250° C. for 24 hr in a stainless steel high pressure reactor. The mixture was cooled and acidified to pH 4 with concentrated hydrochloric acid. The resulting solid was filtered. Cation exchange chromatography of the filtrate afforded a solid that was suspended in water and filtered, washed with water, acetone and ether and dried in vacuo at 60° C. to afford 0.1 g (10%) of the title compound.

Analysis calculated for $C_{15}H_{19}NO_4$: %C, 64.97; %H, 6.91; %N, 5.05. Found: %C, 65.16; %H, 6.67; %N, 4.96.

Field Desorption Mass Spectrum: M=277.

EXAMPLE 21

Preparation of 2SR- and 2RS-2-amino-2-(1SR,2SR-2-carboxycyclopropan-1-yl)-4-(3-methylphenyl)butanoic acid A. (1SR,2SR-2-carbethoxycycloprop-1-yl) (2-(3-methylphenyl)ethyl) ketone: A solution of 5.0 g (20.2 mmol) of 1-iodo-2-(3-methylphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 1.1 g (31%) of the title compound.

Analysis calculated for $C_{16}H_{20}O_3$: %C, 73.82; %H, 7.74. Found: %C, 74.10; %H, 7.92.

B. (1SR,2SR-2-carboxycycloprop-1-yl) (2-(3-methylphenyl)ethyl) ketone: A solution of 1.1 g (4.2 mmol) of the compound from Example 21A in 10 mL of ethanol and 4.6 mL of 1N sodium hydroxide was stirred 2 hr at 50° C., then concentrated in vacuo. The residue was dissolved in 10 mL of water, extracted once with 10 mL of ether, then brought to pH 1 with concentrated hydrochloric acid. The resulting solution was extracted three times with 25 mL each of ether, then the combined organics were dried (MgSO$_4$), filtered and concentrated in vacuo at 60° C. to afford 0.8 g (82%) of the title compound.

C. 5SR- and 5RS-5-(1SR,2SR-2-carboxycyclopropan-1-yl)-5-(2-(3-methylphenyl)ethyl)imidazolidine-2,4-dione: A solution of 0.8 g (3.4 mmol) of the compound from Example 21B in 5 mL of ethanol was added to a solution of 0.5 g (8.5 mmol) of potassium cyanide and 1.2 g (15.3 mmol) of ammonium carbonate in 5 mL of water, then this mixture was placed in a 3.5×20 cm pressure tube, sealed with a #15 Teflon screw plug and heated to 120° C. for 24 hr. The mixture was cooled, vented, added to 150 mL of 1N hydrochloric acid, and the resulting precipitate was filtered and washed three times with water. Recrystallization from acetone/water afforded 0.4 g (40%) of the title compound.

D. A solution of 0.4 g (1.4 mmol) of the compound from Example 21C in 25 mL of 5N sodium hydroxide was heated to 250° C. for 24 hr in a stainless steel high pressure reactor. The mixture was cooled and acidified to pH 2 with concentrated hydrochloric acid. Cation exchange chromatography of this solution afforded a solid that was suspended in water and filtered, washed with water, acetone and ether and dried in vacuo at 60° C. to afford 0.16 g (41%) of the title compound.

Analysis calculated for $C_{15}H_{19}NO_4 \cdot 0.9 H_2O$: %C, 61.38; %H, 7.14; %N, 4.77. Found: %C, 61.44; %H, 6.68; %N, 4.81.

Field Desorption Mass Spectrum: M=277.

EXAMPLE 22

Preparation of 2SR- and 2RS-2-amino-2-(1SR,2SR-2-carboxycyclopropan-1-yl)-4-(4-methylphenyl)butanoic acid A. (1SR,2SR-2-carbethoxycycloprop-1-yl) (2-(4-methylphenyl)ethyl) ketone: A solution of 5.0 g (20.2 mmol) of 1-iodo-2-(4-methylphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.2 g (91%) of the title compound.

Analysis calculated for $C_{16}H_{20}O_3$: %C, 73.82; %H, 7.74. Found: %C, 74.04; %H, 7.72.

B. (1SR,2SR-2-carboxycycloprop-1-yl) (2-(4-methylphenyl)ethyl) ketone: A solution of 3.2 g (12.3 mmol) of the compound from Example 22A in 27 mL of ethanol and 13.5 mL of 1N sodium hydroxide was stirred overnight at room temperature, then concentrated in vacuo. The residue was dissolved in 25 mL of water, brought to pH 2 with concentrated hydrochloric acid. The resulting precipitate was filtered, washed three times with water and dried in vacuo at 60° C. to afford 1.7 g (59%) of the title compound.

C. 5SR- and 5RS-5-(1SR,2SR-2-carboxycyclopropan-1-yl-5-(2-(4-methylphenyl)ethyl)imidazolidine-2,4-dione: A solution of 1.7 g (7.3 mmol) of the compound from Example 22B in 12 mL of ethanol was added to a solution of 1.2 g (18.2 mmol) of potassium cyanide and 2.6 g (32.8 mmol) of ammonium carbonate in 12 mL of water, then this mixture was placed in a 3.5×20 cm pressure tube, sealed with a #15 Teflon screw plug and heated to 120° C. for 24 hr. The mixture was cooled, vented, added to 150 mL of 10% aqueous sodium bisulfate, and the aqueous layer extracted three times with 60 mL each of acetonitrile. The combined organics were dried (MgSO$_4$), filtered and concentrated in vacuo. Recrystallization from acetone/water afforded 1.8 g (81%) of the title compound.

D. 5SR- and 5RS-2,4-di-t-butoxycarbonyl-5-(1SR,2SR-2-carboxycyclopropan-1-yl)-5-(2-(4-methylphenyl)ethyl) imidazolidine-2,4-dione: A solution of 0.8 g (2.6 mmol) of the compound from Example 22C, 0.5 g (5.2 mmol) of triethylamine, 1.7 g (7.7 mmol) of di-t-butyl dicarbonate and 0.025 g (0.2 mmol) of 4-N,N-dimethylaminopyridine in 10 mL of acetonitrile was stirred at room temperature for 3 hr. The mixture was washed with 20 mL of 10% aqueous sodium bisulfate, the organic layer separated and the aqueous layer extracted three times with 25 mL of ether. The combined organics were dried (MgSO$_4$), filtered and concentrated in vacuo to afford 1.2 g (100%) of the title compound.

E. A solution of 1.2 g (2.6 mmol) of the compound from Example 22D in 25 mL of 1N sodium hydroxide was heated to reflux for 24 hr, then cooled and dissolved in 25 mL of concentrated hydrochloric acid. The resulting solution was placed in a 3.5×20 cm pressure tube, sealed with a #15 Teflon screw plug and heated to 150° C. for 8 hr. The solution was cooled, extracted once with 50 mL of ether, then concentrated in vacuo. Cation exchange chromatography of the residue afforded a solid that was suspended in water and filtered, washed with water, acetone and ether and dried in vacuo at 60° C. to afford 0.23 g (32%) of the title compound.

Analysis calculated for $C_{15}H_{19}NO_4$: %C, 64.97; %H, 6.91; %N, 5.05. Found: %C, 64.91; %H, 6.91; %N, 4.97.

Field Desorption Mass Spectrum: M=277.

EXAMPLE 23

Preparation of 2SR- and 2RS-2-amino-2-(1SR,2SR-2-carboxycyclopropan-1-yl)-4-(2-chlorophenyl) butanoic acid A. (1SR,2SR-2-carbethoxycycloprop-1-yl) (2-(2-chlorophenyl)ethyl) ketone: A solution of 5.3 g (20.2 mmol) of 1-iodo-2-(2-chlorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO₄), filtered and concentrated in vacuo. Chromatography (200 g of silica gel, 10% ethyl acetate/hexane) of the residue afforded 2.8 g (73%) of the title compound.

Analysis calculated for $C_{15}H_{17}ClO_3$: %C, 64.17; %H, 6.10. Found: %C, 63.93; %H, 6.14.

B. (1SR,2SR-2-carboxycycloprop-1-yl) (2-(2-chlorophenyl)ethyl) ketone: A solution of 2.6 g (9.2 mmol) of the compound from Example 23A in 20 mL of ethanol and 10.1 mL of 1N sodium hydroxide was stirred 24 hr at room temperature, then concentrated in vacuo. The residue was dissolved in 10 mL of water, extracted twice with 20 mL of ether, then brought to pH 1 with concentrated hydrochloric acid. The resulting solution was extracted four times with 25 mL each of ether, then the combined organics were dried (MgSO₄), filtered and concentrated in vacuo at 60° C. to afford 2.0 g (86%) of the title compound.

C. 5SR- and 5RS-5-(1SR,2SR-2-carboxycyclopropan-1-yl)-5-(2-(2-chlorophenyl)ethyl)imidazolidine-2,4-dione: A solution of 1.9 g (7.7 mmol) of the compound from Example 23B in 13 mL of ethanol was added to a solution of 1.2 g (19.2 mmol) of potassium cyanide and 2.7 g (34.6 mmol) of ammonium carbonate in 13 mL of water, then this mixture was placed in a 3.5×20 cm pressure tube, sealed with a #15 Teflon screw plug and heated to 120° C. for 24 hr. The mixture was cooled, vented, added to 200 mL of 1N hydrochloric acid, and the resulting precipitate was filtered, washed three times with water, dissolved in 25 mL of methanol and concentrated in vacuo, then dissolved in 25 mL of chloroform and concentrated in vacuo to afford 2.5 g (100%) of the title compound.

D. A solution of 2.5 g (7.7 mmol) of the compound from Example 23C in 25 mL of 5N sodium hydroxide was heated to 250° C. for 24 hr in a stainless steel high pressure reactor. The mixture was cooled and acidified to pH 2 with concentrated hydrochloric acid. Cation exchange chromatography of this solution afforded a solid that was suspended in water and filtered, washed with water, acetone and ether and dried in vacuo at 60° C. to afford 0.81 g (35%) of the title compound.

Analysis calculated for $C_{14}H_{16}NO_4Cl$: %C, 56.48; %H, 5.42; %N, 4.70. Found: %C, 56.76; %H, 5.48; %N, 4.76.

Field Desorption Mass Spectrum: M+1=298.

EXAMPLE 24

Preparation of 2SR- and 2RS-2-amino-2-(1SR,2SR-2-carboxycyclopropan-1-yl)-4-(3-chlorophenyl)butanoic acid A. (1SR,2SR-2-carbethoxycycloprop-1-yl) (2-(3-chlorophenyl)ethyl) ketone: A solution of 5.3 g (20.2 mmol) of 1-iodo-2-(3-chlorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 0 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried (MgSO₄), filtered and concentrated in vacuo. Chromatography (200 g of silica gel, 10% ethyl acetate/hexane) of the residue afforded 2.8 g (75%) of the title compound.

Analysis calculated for $C_{15}H_{17}ClO_3$: %C, 64.17; %H, 6.10. Found: %C, 63.96; %H, 6.28.

B. (1SR,2SR-2-carboxycycloprop-1-yl) (2-(3-chlorophenyl)ethyl) ketone: A solution of 2.8 g (10 mmol) of the compound from Example 24A in 22 mL of ethanol and 11 mL of 1N sodium hydroxide was stirred 24 hr at room temperature, then concentrated in vacuo. The residue was dissolved in 10 mL of water, extracted twice with 20 mL of ether, then brought to pH 1 with concentrated hydrochloric acid. The resulting solution was extracted four times with 25 mL each of ether, then the combined organics were dried (MgSO₄), filtered and concentrated in vacuo at 60° C. to afford 2.2 g (87%) of the title compound.

C. 5SR- and 5RS-5-(1SR,2SR-2-carboxycyclopropan-1-yl)-5-(2-(3-chlorophenyl)ethyl)imidazolidine-2,4-dione: A solution of 2.1 g (8.3 mmol) of the compound from Example 24B in 14 mL of ethanol was added to a solution of 1.3 g (20.8 mmol) of potassium cyanide and 2.9 g (37.4 mmol) of ammonium carbonate in 14 mL of water, then this mixture was placed in a 3.5×20 cm pressure tube, sealed with a #15 Teflon screw plug and heated to 120° C. for 24 hr. The mixture was cooled, vented, added to 200 mL of 1N hydrochloric acid, and the resulting precipitate was filtered, washed three times with water and dried in vacuo at 60° C. to afford 2.5 g (91%) of the title compound.

D. A solution of 2.4 g (7.4 mmol) of the compound from Example 24C in 25 mL of 5N sodium hydroxide was heated to 250° C. for 24 hr in a stainless steel high pressure reactor. The mixture was cooled and acidified to pH 7 with concentrated hydrochloric acid, affording a solid that was filtered and washed three times with water and twice with acetone. The solid was dissolved in water at pH 9, and cation exchange chromatography of this solution afforded a solid that was suspended in water and filtered, washed with water, acetone and ether and dried in vacuo at 60° C. to afford 0.91 g (41%) of the title compound.

Analysis calculated for $C_{14}H_{16}NO_4Cl$: %C, 56.48; %H, 5.42; %N, 4.70. Found: %C, 56.34; %H, 5.42; %N, 4.49.

Field Desorption Mass Spectrum: M=297.

EXAMPLE 25

Preparation of 2SR- and 2RS-2-amino-2-(1SR,2SR-2-carboxycyclopropan-1-yl)-4-(4-chlorophenyl)butanoic acid A. (1SR,2SR-2-carbethoxycycloprop-1-yl) (2-(4-chlorophenyl)ethyl) ketone: A solution of 5.3 g (20.2 mmol) of 1-iodo-2-(4-chlorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.3 g (60%) of the title compound.

Analysis calculated for $C_{15}H_{17}ClO_3$: %C, 64.17; %H, 6.10. Found: %C, 64.38; %H, 6.22.

B. (1SR,2SR-2-carboxycycloprop-1-yl) (2-(4-chlorophenyl)ethyl) ketone: A solution of 2.3 g (8.1 mmol) of the compound from Example 25A in 18 mL of ethanol and 8.9 mL of 1N sodium hydroxide was stirred 24 hr at room temperature, then concentrated in vacuo. The residue was dissolved in 10 mL of water, extracted twice with 20 mL of ether, then brought to pH 1 with concentrated hydrochloric acid. The resulting solution was extracted four times with 25 mL each of ether, then the combined organics were dried ($MgSO_4$), filtered and concentrated in vacuo at 60° C. to afford 1.8 g (90%) of the title compound.

C. 5SR- and 5RS-5-(1SR,2SR-2-carboxycyclopropan-1-yl)-5-(2-(4-chlorophenyl)ethyl)imidazolidine-2,4-dione: A solution of 1.8 g (7 mmol) of the compound from Example 25B in 13 mL of ethanol was added to a solution of 1.1 g (17.5 mmol) of potassium cyanide and 2.5 g (31.5 mmol) of ammonium carbonate in 13 mL of water, then this mixture was placed in a 3.5×20 cm pressure tube, sealed with a #15 Teflon screw plug and heated to 120° C. for 24 hr. The mixture was cooled, vented, added to 200 mL of 1N hydrochloric acid, and the resulting precipitate was filtered, washed three times with water, dissolved in 25 mL of methanol and concentrated in vacuo, then dissolved in 25 mL of chloroform and concentrated in vacuo to afford 2.0 g (88%) of the title compound.

D. A solution of 2.0 g (6.2 mmol) of the compound from Example 25C in 25 mL of 5N sodium hydroxide was heated to 250° C. for 24 hr in a stainless steel high pressure reactor. Cation exchange chromatography of this solution afforded a solid that was suspended in water and filtered, washed with water, acetone and ether and dried in vacuo at 60° C. to afford 0.81 g (35%) of the title compound.

Analysis calculated for $C_{14}H_{16}N_2O_4Cl$: %C, 56.48; %H, 5.42; %N, 4.70. Found: %C, 56.37; %H, 5.49; %N, 4.45.

Field Desorption Mass Spectrum: M=297.

EXAMPLE 26

Preparation of 2SR- and 2RS-2-amino-2-(1SR,2SR-2-carboxycyclopropan-1-yl)-4-(2-methoxyphenyl) butanoic acid A. (1SR,2SR-2-carbethoxycycloprop-1-yl) (2-(2-methoxyphenyl)ethyl) ketone: A solution of 5.3 g (20.2 mmol) of 1-iodo-2-(2-methoxyphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 10% ethyl acetate/hexane) of the residue afforded 1.1 g (30%) of the title compound.

Analysis calculated for $C_{16}H_{20}O_4 \cdot 0.25 H_2O$: %C, 65.18; %H, 7.01. Found: %C, 64.87; %H, 6.84.

B. (1SR,2SR-2-carboxycycloprop-1-yl) (2-(2-methoxyphenyl)ethyl) ketone: A solution of 2.3 g (8.1 mmol) of the compound from Example 26A in 9 mL of ethanol and 4.4 mL of 1N sodium hydroxide was stirred 24 hr at room temperature, then concentrated in vacuo. The residue was dissolved in 10 mL of concentrated hydrochloric acid and extracted four times with 25 mL each of ether, then the combined organics were dried ($MgSO_4$), filtered and concentrated in vacuo at 60° C. to afford 1.1 g (100%) of the title compound.

C. 5SR- and 5RS-5-(1SR,2SR-2-carboxycyclopropan-1-yl)-5-(2-(2-methoxyphenyl)ethyl)imidazolidine-2,4-dione: A solution of 1.0 g (4.3 mmol) of the compound from Example 26B in 7 mL of ethanol was added to a solution of 0.7 g (10.8 mmol) of potassium cyanide and 1.5 g (19.4 mmol) of ammonium carbonate in 7 mL of water, then this mixture was placed in a 3.5×20 cm pressure tube, sealed with a #15 Teflon screw plug and heated to 125° C. for 24 hr. The mixture was cooled, vented, added to 75 mL of 1N hydrochloric acid, then cooled to 0° C. overnight. The resulting precipitate was filtered, washed three times with water, then recrystallized from water and acetone to afford 0.8 g (58%) of the title compound.

D. A solution of 0.8 g (2.5 mmol) of the compound from Example 26C in 25 mL of 5N sodium hydroxide was heated to 250° C. for 24 hr in a stainless steel high pressure reactor. The mixture was cooled and acidified to pH 2 with concentrated hydrochloric acid. Cation exchange chromatography of this solution afforded a solid that was suspended in water and filtered, washed with water, acetone and ether and dried in vacuo at 60° C. to afford 0.29 g (40%) of the title compound.

Analysis calculated for $C_{15}H_{19}NO_5 \cdot 0.25 H_2O$: %C, 60.49; %H, 6.60; %N, 4.70. Found: %C, 60.71; %H, 6.39; %N, 4.78.

Field Desorption Mass Spectrum: M=293.

EXAMPLE 27

Preparation of 2SR- and 2RS-2-amino-2-(1SR,2SR-2-carboxycyclopropan-1-yl)-4-(3-methoxyphenyl)butanoic acid A. (1SR,2SR-2-carbethoxycycloprop-1-yl) (2-(3-methoxyphenyl)ethyl) ketone: A solution of 3.8 g (14.5 mmol) of 1-iodo-2-(3-methoxyphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.6 g (70%) of the title compound.

Analysis calculated for $C_{16}H_{20}O_4$: %C, 69.55; %H, 7.30. Found: %C, 69.28; %H, 7.39.

B. (1SR,2SR-2-carboxycycloprop-1-yl) (2-(3-methoxyphenyl)ethyl) ketone: A solution of 2.6 g (9.4 mmol) of the compound from Example 27A in 20 mL of ethanol and 10.3 mL of 1N sodium hydroxide was stirred 24 hr at room temperature, then concentrated in vacuo. The residue was dissolved in 20 mL of water and extracted once with ether. The aqueous layer was acidified to pH 1 with concentrated hydrochloric acid and extracted three times with 25 mL each of ether, then the combined organics were dried ($MgSO_4$), filtered and concentrated in vacuo at 60° C. to afford 1.9 g (80%) of the title compound.

C. 5SR- and 5RS-5-(1SR,2SR-2-carboxycyclopropan-1-yl)-5-(2-(3-methoxyphenyl)ethyl)imidazolidine-2,4-dione: A solution of 1.9 g (7.5 mmol) of the compound from Example 27B in 13 mL of ethanol was added to a solution of 1.2 g (19 mmol) of potassium cyanide and 2.6 g (33.9 mmol) of ammonium carbonate in 13 mL of water, then this mixture was placed in a 3.5×20 cm pressure tube, sealed with a #15 Teflon screw plug and heated to 125° C. for 24 hr. The mixture was cooled, vented, added to 150 mL of 10% aqueous sodium bisulfate, and the resulting precipitate was filtered, washed three times with water, then recrystallized from water and acetone to afford 1.7 g (72%) of the title compound.

D. A solution of 0.8 g (2.6 mmol) of the compound from Example 27C and 4.1 g (13 mmol) of barium hydroxide in 20 mL of water was heated to reflux for 72 hr. The mixture was cooled, neutralized with 0.7 mL (13 mmol) of concentrated sulfuric acid, then filtered and the filter cake washed twice with 10 mL each of boiling 10% pyridine/water. Cation exchange chromatography of the filtrate afforded a solid that was suspended in water and filtered, washed with water, acetone and ether and dried in vacuo at 60° C. to afford 0.11 g (14%) of the title compound.

Analysis calculated for $C_{15}H_{19}NO_5 \cdot 0.25\ H_2O$: %C, 60.49; %H, 6.60; %N, 4.70. Found: %C, 60.34; %H, 6.40; %N, 4.65.

Field Desorption Mass Spectrum: M=293.

EXAMPLE 28

Preparation of 2SR- and 2RS-2-amino-2-(1SR,2SR-2-carboxycyclopropan-1-yl)-4-(4-methoxyphenyl) butanoic acid A. (1SR,2SR-2-carbethoxycycloprop-1-yl) (2-(4-methoxyphenyl)ethyl) ketone: A solution of 3.8 g (14.5 mmol) of 1-iodo-2-(4-methoxyphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.9 g (78%) of the title compound.

Analysis calculated for $C_{16}H_{20}O_4$: %C, 69.55; %H, 7.30. Found: %C, 69.36; %H, 7.47.

B. (1SR,2SR-2-carboxycycloprop-1-yl) (2-(4-methoxyphenyl)ethyl) ketone: A solution of 2.1 g (7.6 mmol) of the compound from Example 28A in 17 mL of ethanol and 8.4 mL of 1N sodium hydroxide was stirred 24 hr at room temperature, then concentrated in vacuo. The residue was dissolved in 20 mL of 1N hydrochloric acid and extracted three times with 25 mL each of ether, then the combined organics were dried ($MgSO_4$), filtered and concentrated in vacuo to afford 1.5 g (83%) of the title compound.

C. 5SR- and 5RS-5-(1SR,2SR-2-carboxycyclopropan-1-yl)-5-(2-(4-methoxyphenyl)ethyl)imidazolidine-2,4-dione: A solution of 1.5 g (6.3 mmol) of the compound from Example 28B in 11 mL of ethanol was added to a solution of 1.0 g (15.7 mmol) of potassium cyanide and 2.2 g (28.3 mmol) of ammonium carbonate in 11 mL of water, then this mixture was placed in a 3.5×20 cm pressure tube, sealed with a #15 Teflon screw plug and heated to 125° C. for 24 hr. The mixture was cooled, vented, added to 150 mL of 1N hydrochloric acid, then cooled to 0° C. overnight. The resulting precipitate was filtered, washed three times with water, then recrystallized from water and acetone to afford 1.6 g (77%) of the title compound.

D. A solution of 1.5 g (4.7 mmol) of the compound from Example 28C in 25 mL of 5N sodium hydroxide was heated to 250° C. for 24 hr in a stainless steel high pressure reactor. The mixture was cooled and acidified to pH 4 with concentrated hydrochloric acid. The resulting solid was filtered, washed with water, acetone and ether and dried in vacuo at 60° C. to afford 0.72 g (52%) of the title compound.

Analysis calculated for $C_{15}H_{19}NO_5$: %C, 61.42; %H, 6.53; %N, 4.78. Found: %C, 61.15; %H, 6.34; %N, 4.55.

Field Desorption Mass Spectrum: M=293.

EXAMPLE 29

Preparation of 2SR- and 2RS-2-amino-2-(1SR,2SR-2-carboxycyclopropan-1-yl)-4-(2-hydroxyphenyl)butanoic acid A. A solution of 0.18 g (0.7 mmol) of the compound from Example 26D in 5 mL of 48% aqueous hydrobromic acid was heated to 110° C. for 24 hr, then cooled and concentrated in vacuo. The residue was dissolved in 5 mL of water and concentrated in vacuo, and this procedure was then repeated. Cation exchange chromatography of the residue gave a solid that was suspended in water and filtered, washed with water, acetone and ether and dried in vacuo at 60° C. to afford 0.092 g (47%) of the title compound.

Analysis calculated for $C_{14}H_{17}NO_5 \cdot 0.75\ H_2O$: %C, 57.43; %H, 6.37; %N, 4.78. Found: %C, 57.07; %H, 5.87; %N, 4.67.

Field Desorption Mass Spectrum: M=279.

EXAMPLE 30

Preparation of 2SR- and 2RS-2-amino-2-(1SR,2SR-2-carboxycyclopropan-1-yl)-4-(3-hydroxyphenyl) butanoic acid A. 2SR- and 2RS-2-amino-2-(1SR,2SR-2-carboxycyclopropan-1-yl)-4-(3-methoxyphenyl)butanoic acid and 2SR- and 2RS-2-amino-2-(1SR,2SR-2-carboxycyclopropan-1-yl)-4-(3-hydroxyphenyl)butanoic acid: A solution of 1.2 g (4.7 mmol) of the compound from Example 27C in 25 mL of 5N sodium hydroxide was heated to 250° C. for 24 hr in a stainless steel high pressure reactor. The mixture was cooled and acidified to pH 3 with concentrated hydrochloric acid. Cation exchange chromatography of this solution afforded a solid that was filtered, washed with water, acetone and ether and dried in vacuo at 60° C. to afford 0.50 g (44%) of a mixture of hydroxy and methoxy compounds by 1H NMR and mass spectral analysis.

B. A solution of 0.43 g (1.5 mmol) of the compounds from Example 30A in 5 mL of 48% aqueous hydrobromic acid was heated to 110° C. for 24 hr, then cooled and concentrated in vacuo. The residue was dissolved in 5 mL of water and concentrated in vacuo, and this procedure was then repeated. Cation exchange chromatography of the residue gave a solid that was suspended in water and filtered, washed with water, acetone and ether and dried in vacuo at 60° C. to afford 0.19 g (46%) of the title compound.

Analysis calculated for $C_{14}H_{17}NO_5 \cdot 0.5\ H_2O$: %C, 58.33; %H, 6.29; %N, 4.86. Found: %C, 58.29; %H, 6.13; %N, 4.83.

Field Desorption Mass Spectrum: M=279.

EXAMPLE 31

Preparation of 2SR- and 2RS-2-amino-2-(1SR,2SR-2-carboxycyclopropan-1-yl)-4-(4-hydroxyphenyl)butanoic acid A. A solution of 0.36 g (1.2 mmol) of the compound from Example 28D in 5 mL of 48% aqueous hydrobromic acid was heated to 110° C. for 24 hr, then cooled and concentrated in vacuo. The residue was dissolved in 5 mL of water and concentrated in vacuo, and this procedure was then repeated. Cation exchange chromatography of the residue gave a solid that was suspended in water and filtered, washed with water, acetone and ether and dried in vacuo at 60° C. to afford 0.17 g (52%) of the title compound.

Analysis calculated for $C_{14}H_{17}NO_5 \cdot 0.75\ H_2O$: %C, 57.43; %H, 6.37; %N, 4.78. Found: %C, 57.18; %H, 5.85; %N, 4.56.

Field Desorption Mass Spectrum: M+1=280.

EXAMPLE 32

Preparation of 2SR- and 2RS-2-amino-2-(1SR,2SR-2-carboxycyclopropan-1-yl)-4-(2,5-dimethoxyphenyl)butanoic acid A. (1SR,2SR-2-carbethoxycycloprop-1-yl) (2-(2,5-dimethoxyphenyl)ethyl) ketone: A solution of 4.2 g (14.5 mmol) of 1-iodo-2-(2,5-dimethoxyphenyl)ethane and 2.0 g (31 mmol) of zinc/copper couple in 66 mL of benzene and 8 mL of N,N-dimethylacetamide was stirred for 3 hr at 60° C., then treated with 0.3 g (0.3 mmol) of tetrakis(triphenylphosphine)palladium(0) and heated for 5 min more. The heating bath was removed, 2.4 g (13.5 mmol) of the material from Preparation 1 was added and the mixture stirred at room temperature for 72 hr. The mixture was diluted with 80 mL of ether and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 25% ethyl acetate/hexane) of the residue afforded 1.7 g (41%) of the title compound.

Analysis calculated for $C_{17}H_{22}O_4$: %C, 66.65; %H, 7.24. Found: %C, 66.42; %H, 7.21.

B. (1SR,2SR-2-carboxycycloprop-1-yl) (2-(2,5-dimethoxyphenyl)ethyl) ketone: A solution of 1.6 g (5.2 mmol) of the compound from Example 32A in 12 mL of ethanol and 5.7 mL of 1N sodium hydroxide was stirred 24 hr at room temperature, then concentrated in vacuo. The residue was dissolved in 50 mL of 10% aqueous sodium bisulfate and extracted three times with 35 mL each of ether, then the combined organics were dried ($MgSO_4$), filtered and concentrated in vacuo to afford 1.1 g (76%) of the title compound.

C. 5SR- and 5RS-5-(1SR,2SR-2-carboxycyclopropan-1-yl)-5-(2-(2,5-dimethoxyphenyl)ethyl)imidazolidine-2,4-dione: A solution of 1.1 g (3.9 mmol) of the compound from Example 32B in 10 mL of ethanol was added to a solution of 1.3 g (19.8 mmol) of potassium cyanide and 2.8 g (35.6 mmol) of ammonium carbonate in 10 mL of water, then this mixture was heated to 55° C. for 24 hr. The mixture was cooled and added to 150 mL of 10% aqueous sodium bisulfate. The resulting solid was filtered, washed three times with water, and dried in vacuo at 60° C. to afford 1.0 g (74%) of the title compound.

D. A solution of 1.0 g (2.9 mmol) of the compound from Example 32C in 10 mL of 5N sodium hydroxide was heated to 250° C. for 24 hr in a stainless steel high pressure reactor. The mixture was cooled and acidified to pH 7 with concentrated hydrochloric acid. Cation exchange chromatography of this solution gave a solid that was suspended in water and filtered, washed with water, acetone and ether and dried in vacuo at 60° C. to afford 0.28 g (30%) of the title compound.

Analysis calculated for $C_{16}H_{21}NO_6$: %C, 59.43; %H, 6.55; %N, 4.33. Found: %C, 59.60; %H, 6.46; %N, 4.52.

Field Desorption Mass Spectrum: M=323.

EXAMPLE 33

Preparation of 2SR- and 2RS-2-amino-2-(1SR,2SR-2-carboxycyclopropan-1-yl)-4-(3,4-dimethoxyphenyl)butanoic acid A. (1SR,2SR-2-carbethoxycycloprop-1-yl) (2-(3,4-dimethoxyphenyl)ethyl) ketone: A solution of 4.2 g (14.5 mmol) of 1-iodo-2-(3,4-dimethoxyphenyl)ethane and 2.0 g (31 mmol) of zinc/copper couple in 66 mL of benzene and 8 mL of N,N-dimethylacetamide was stirred for 3 hr at 60° C., then treated with 0.3 g (0.3 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 80 mL of ether and filtered through diatomaceous earth. The filtrate was washed with 50 mL of 10% aqueous sodium bisulfate, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 25% ethyl acetate/hexane) of the residue afforded 2.7 g (65%) of the title compound.

Analysis calculated for $C_{17}H_{22}O_4$: %C, 66.65; %H, 7.24. Found: %C, 67.17; %H, 7.15.

B. (1SR,2SR-2-carboxycycloprop-1-yl) (2-(3,4-dimethoxyphenyl)ethyl) ketone: A solution of 2.6 g (8.5 mmol) of the compound from Example 33A in 20 mL of ethanol and 9.3 mL of 1N sodium hydroxide was stirred 24 hr at room temperature, then concentrated in vacuo. The residue was dissolved in 50 mL of 10% aqueous sodium bisulfate and extracted three times with 35 mL each of ether, then the combined organics were dried ($MgSO_4$), filtered and concentrated in vacuo to afford 2.4 g (100%) of the title compound.

C. 5SR- and 5RS-5-(1SR,2SR-2-carboxycyclopropan-1-yl)-5-(2-(3,4-dimethoxyphenyl)ethyl)imidazolidine-2,4-dione: A solution of 2.3 g (8.3 mmol) of the compound from Example 33B in 14 mL of ethanol was added to a solution of 2.7 g (41.3 mmol) of potassium cyanide and 5.8 g (74.4 mmol) of ammonium carbonate in 14 mL of water, then this mixture was heated to 55° C. for 24 hr. The mixture was cooled and added to 150 mL of 10% aqueous sodium bisulfate. The resulting solid was filtered, washed three times with water, and dried in vacuo at 60° C. to afford 1.7 g (59%) of the title compound.

D. A solution of 1.7 g (4.8 mmol) of the compound from Example 33C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of this solution gave a solid that was suspended in acetone, refluxed for 2 hr, then cooled and filtered, washed with acetone and ether and dried in vacuo at 60° C. to afford 0.72 g (46%) of the title compound.

Analysis calculated for $C_{16}H_{21}NO_6 \cdot 0.25\ H_2O$: %C, 58.62; %H, 6.61; %N, 4.27. Found: %C, 58.48; %H, 6.18; %N, 4.40.

Field Desorption Mass Spectrum: M=323.

EXAMPLE 34

Preparation of 2SR,5SR-, 2SR,5RS-, 2RS,5SR- and 2RS, 5RS-2-amino-2-(1SR,2SR-2-carboxycyclopropan-1-yl )-4-methyl -4-phenylbutanoic acid A. (1SR,2SR-2-carbethoxycycloprop-1-yl) (2SR- and 2RS-2-methyl-2-phenylethyl) ketone: A solution of 5.0 g (20.2 mmol) of 2SR- and 2RS-1-iodo-2-methyl-2-phenylethane and 2.0 g (31 mmol) of zinc/copper couple in 66 mL of benzene and 8 mL of N,N-dimethylacetamide was stirred for 3 hr at 60° C., then treated with 0.3 g (0.3 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 150 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 10% ethyl acetate/hexane) of the residue afforded 3.3 g (94%) of the title compound.

Analysis calculated for $C_{16}H_{20}O_3$: %C, 73.82; %H, 7.74. Found: %C, 74.09; %H, 7.62.

B. (1SR,2SR-2-carboxycycloprop-1-yl) (2SR- and 2RS-2-methyl-2-phenylethyl) ketone: A solution of 3.3 g (12.7 mmol) of the compound from Example 34A in 28 mL of ethanol and 14 mL of 1N sodium hydroxide was stirred 24 hr at 60° C., then concentrated in vacuo. The residue was dissolved in 25 mL of water, extracted twice with 25 mL of ether, then the aqueous layer was acidified to pH 1 with 50 mL of 10% aqueous sodium bisulfate and extracted three times with 35 mL each of ether. The combined organics were dried (MgSO$_4$), filtered and concentrated in vacuo to afford 1.9 g (64%) of the title compound.

C. 5SR- and 5RS-5-(1SR,2SR-2-carboxycyclopropan-1-yl)-5-((2SR- and 2RS-2-methyl-2-phenyl)ethyl) imidazolidine-2,4-dione: A solution of 1.9 g (8.2 mmol) of the compound from Example 34B in 14 mL of ethanol was added to a solution of 2.7 g (41.3 mmol) of potassium cyanide and 5.7 g (73.6 mmol) of ammonium carbonate in 14 mL of water, then this mixture was heated to 80° C. for 24 hr. The mixture was cooled and added to 150 mL of 10% aqueous sodium bisulfate. The resulting solid was filtered, washed three times with water, and dried in vacuo at 60° C. to afford 1.8 g (74%) of the title compound.

D. A solution of 1.8 g (6 mmol) of the compound from Example 34C and 9.5 g (30.3 mmol) of barium hydroxide in 20 mL of water was heated to reflux for 72 hr. The mixture was cooled and treated with 1.7 mL (30.3 mmol) of concentrated sulfuric acid. The resulting solid was filtered and washed three times with water. Upon standing, a solid precipitates from the filtrate that is filtered, washed with water, acetone and ether. Cation exchange chromatography of this filtrate gave a solid that was suspended in water, filtered, washed with water, acetone and ether and dried in vacuo at 60° C. to afford 0.28 g (17%) of the title compound.

Analysis calculated for $C_{15}H_{19}NO_4$: %C, 64.97; %H, 6.91; %N, 5.05. Found: %C, 65.10; %H, 6.82; %N, 5.15.

Field Desorption Mass Spectrum: M=277.

EXAMPLE 35

Preparation of 2SR- and 2RS-2-amino-2-(1SR,2SR-2-carboxycyclopropan-1-yl)-3-(dibenzopyran-4-yl)propanoic acid A. (1SR,2SR-2-carbethoxycycloprop-1-yl) ((dibenzopyran-4-yl)methyl) ketone: A solution of 4.7 g (14.5 mmol) of (dibenzopyran-4-yl)methyl iodide and 2.0 g (31 mmol) of zinc/copper couple in 66 mL of benzene and 8 mL of N,N-dimethylacetamide was stirred for 3 hr at 60° C., then treated with 0.3 g (0.3 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 150 mL of ether and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 20% ethyl acetate/hexane) of the residue afforded 2.9 g (64%) of the title compound.

Analysis calculated for $C_{16}H_{20}O_3$: %C, 74.98; %H, 5.99. Found: %C, 75.02; %H, 5.84.

B. (1SR,2SR-2-carboxycycloprop-1-yl) ((dibenzopyran-4-yl)methyl) ketone: A solution of 2.9 g (8.6 mmol) of the compound from Example 35A in 20 mL of ethanol and 9.5 mL of 1N sodium hydroxide was stirred 24 hr at 50° C., then concentrated in vacuo. The residue was dissolved in 50 mL of 10% aqueous sodium bisulfate and extracted three times with 35 mL each of ether. The combined organics were dried (MgSO$_4$), filtered and concentrated in vacuo to afford 2.0 g (75%) of the title compound.

C. 5SR- and 5RS-5-(1SR,2SR-2-carboxycyclopropan-1-yl)-5-((dibenzopyran-4-yl)methyl)imidazolidine-2,4-dione: A solution of 2.0 g (6.5 mmol) of the compound from Example 35B in 11 mL of ethanol was added to a solution of 2.1 g (32.4 mmol) of potassium cyanide and 4.6 g (58.4 mmol) of ammonium carbonate in 11 mL of water, then this mixture was heated to 55° C. for 48 hr. The mixture was cooled and added to 150 mL of 10% aqueous sodium bisulfate. The resulting mixture was allowed to stand overnight at room temperature, then the solid was filtered, and recrystallization from acetone and water afforded 1.1 g (41%) of the title compound.

D. A solution of 1.0 g (2.6 mmol) of the compound from Example 35C and 4.2 g (13.2 mmol) of barium hydroxide in 10 mL of water was heated to reflux for 48 hr. The mixture was cooled and treated with 0.7 mL (13.2 mmol) of concentrated sulfuric acid. The resulting solid was filtered and washed three times with water. Cation exchange chromatography of the filtrate gave a solid that was suspended in water, filtered, washed with water, acetone and ether and dried in vacuo at 60° C. to afford 0.03 g (3%) of the title compound.

Analysis calculated for $C_{20}H_{19}NO_5 \cdot 0.4\ H_2O$: %C, 66.62; %H, 5.53; %N, 3.88. Found: %C, 66.54; %H, 5.19; %N, 4.29.

Field Desorption Mass Spectrum: M=353.

EXAMPLE 36

Preparation of 2SR- and 2RS-2-amino-2-(1SR,2SR-2-carboxycyclopropan-1-yl)-3-(adamant-1-yl)propanoic acid A. (1SR,2SR-2-carbethoxycycloprop-1-yl) (2-(adamant-1-yl)ethyl) ketone: A solution of 4.9 g (17 mmol) of 1-iodo-2-(adamant-1-yl)ethane and 2.1 g (32.7 mmol) of zinc/copper couple in 47 mL of benzene and 5 mL of N,N-dimethylacetamide was stirred for 2 hr at 60° C., then treated with 0.3 g (0.3 mmol) of tetrakis(triphenylphosphine)palladium(0) and heated for 5 min more. The heating bath was removed, 2.5 g (14.2 mmol) of the material from Preparation 1 was added and the mixture stirred at room temperature for 1 hr. The mixture was diluted with 50 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried ($MgSO_4$), filtered and concentrated in vacuo. Chromatography (250 g of silica gel, 5% ethyl acetate/hexane) of the residue afforded 3.3 g (77%) of the title compound.

B. (1SR,2SR-2-carboxycycloprop-1-yl) (2-(adamant-1-yl)ethyl) ketone: A solution of 3.3 g (10.9 mmol) of the compound from Example 36A in 35 mL of ethanol and 6 mL of 2N sodium hydroxide was stirred 24 hr at room temperature, then concentrated in vacuo. The residue was dissolved in 40 mL of water, extracted three times with 25 mL each of ethyl acetate, then acidified to pH 1 with 50 mL of 10% aqueous sodium bisulfate and extracted four times with 50 mL each of ethyl acetate. The combined organics were dried ($MgSO_4$), filtered and concentrated in vacuo to afford 2.8 g (94%) of the title compound.

C. 5SR- and 5RS-5-(1SR,2SR-2-carboxycyclopropan-1-yl)-5-(2-(adamant-1-yl)ethyl)imidazolidine-2,4-dione: A solution of 2.7 g (9.9 mmol) of the compound from Example 36B in 10 mL of ethanol was added to a solution of 1.6 g (24.7 mmol) of potassium cyanide and 4.3 g (44.5 mmol) of ammonium carbonate in 10 mL of water, then this mixture was placed in a 3.5×20 cm pressure tube, sealed with a #15 Teflon screw plug and heated to 125° C. for 24 hr. The mixture was cooled, vented, added to 125 mL of 10% aqueous sodium bisulfate, and the resulting precipitate was filtered, washed three times with water, then recrystallized from water and acetone to afford 2.1 g (60%) of the title compound.

D. A solution of 2.0 g (5.7 mmol) of the compound from Example 36C in 25 mL of 5N sodium hydroxide was heated to 250° C. for 24 hr in a stainless steel high pressure reactor. The mixture was cooled and acidified to pH 2 with concentrated hydrochloric acid, then diluted with 350 mL of acetone. The top layer of this biphasic solution was concentrated in vacuo to 100 mL, and the resulting precipitate was filtered, washing with water and acetone. This material was suspended in 10 mL of water, and sufficient 5N sodium hydroxide was added until the material dissolved, then the pH was adjusted to 2 with 5N hydrochloric acid. The resulting solid was filtered, washed with water and dried in vacuo at 60° C. to afford 0.64 g (35%) of the title compound.

Analysis calculated for $C_{18}H_{27}NO_4 \cdot 0.7\ H_2O$: %C, 64.55; %H, 8.58; %N, 4.18. Found: %C, 64.58; %H, 8.44; %N, 4.28.

Field Desorption Mass Spectrum: M+1=322.

EXAMPLE 37

Preparation of 2SR- and 2RS-2-amino-2-(1SR,2SR-2-carboxycyclopropan-1-yl)-4-(3-(trifluoromethyl)phenyl) butanoic acid A. (1SR,2SR-2-carbethoxycycloprop-1-yl) (2-(3-(trifluoromethyl)phenyl)ethyl) ketone: A solution of 7.1 g (23.8 mmol) of 1-iodo-2-(3-(trifluoromethyl)phenyl)ethane and 3.0 g (45.5 mmol) of zinc/copper couple in 65 mL of benzene and 7 mL of N,N-dimethylacetamide was stirred for 3 hr at 60° C., then treated with 0.5 g (0.4 mmol) of tetrakis(triphenylphosphine)palladium(0) and heated for 5 min more. The heating bath was removed, 3.5 g (19.8 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried ($MgSO_4$), filtered and concentrated in vacuo. Chromatography (250 g of silica gel, 15% ethyl acetate/hexane) of the residue afforded 4.1 g (65%) of the title compound.

Analysis calculated for $C_{16}H_{17}F_3O_3$: %C, 61.14; %H, 5.45. Found: %C, 61.38; %H, 5.44.

B. (1SR,2SR-2-carboxycycloprop-1-yl) (2-(3-(trifluoromethyl)phenyl)ethyl) ketone: A solution of 3.7 g (12.9 mmol) of the compound from Example 37A in 40 mL of ethanol and 3.8 mL of 5N sodium hydroxide was stirred 24 hr at room temperature, then concentrated in vacuo. The residue was dissolved in 50 mL of 10% sodium bisulfate and extracted four times with 25 mL each of ethyl acetate, then the combined organics were dried ($MgSO_4$), filtered and concentrated in vacuo to afford 3.7 g (100%) of the title compound.

C. 5SR- and 5RS-5-(1SR,2SR-2-carboxycyclopropan-1-yl)-5-(2-(3-(trifluoromethyl)phenyl)ethyl)imidazolidine-2,4-dione: A solution of 3.7 g (12.9 mmol) of the compound from Example 37B in 15 mL of ethanol was added to a solution of 4.2 g (64.5 mmol) of potassium cyanide and 11.2 g (116.1 mmol) of ammonium carbonate in 15 mL of water, then this mixture was heated to 55° C. for 24 hr. The mixture was cooled and added to 300 mL of 10% aqueous sodium bisulfate, and the resulting precipitate was filtered, washed three times with water, and dried in vacuo at 60° C. to afford 4.6 g (100%) of the title compound.

D. A solution of 4.6 g (12.9 mmol) of the compound from Example 37C and 20.4 g (64.5 mmol) of barium hydroxide in 20 mL of water was heated to 250° C. for 24 hr in a stainless steel high pressure reactor. The mixture was cooled and acidified to pH 5 with concentrated sulfuric acid, affording a solid that was filtered and washed with water. The filtrate was concentrated in vacuo to afford a solid, and this was suspended in water and filtered. Cation exchange chromatography of the filtrate afforded a solid that was suspended in water and filtered, washed with water, acetone and ether and dried in vacuo at 60° C. to afford 1.3 g (30%) of the title compound.

Analysis calculated for $C_{15}H_{16}F_3NO_4 \cdot 0.5\ H_2O$: %C, 52.94; %H, 5.04; %N, 4.12. Found: %C, 53.01; %H, 4.81; %N, 4.00.

Field Desorption Mass Spectrum: M+1=332.

EXAMPLE 38

Preparation of 2SR- and 2RS-2-amino-2-(1SR,2SR-2-carboxycyclopropan-1-yl)-4-(3-bromophenyl) butanoic acid A. (1SR,2SR-2-carbethoxycycloprop-1-yl) (2-(3-bromophenyl)ethyl) ketone: A solution of 5.3 g (17 mmol) of 1-iodo-2-(3-bromophenyl)ethane and 2.1 g (32.7 mmol) of zinc/copper couple in 47 mL of benzene and 5 mL of N,N-dimethylacetamide was stirred for 2 hr at 60° C., then treated with 0.5 g (0.4 mmol) of tetrakis (triphenylphosphine)palladium(0) and heated for 5 min more. The heating bath was removed, 2.5 g (14.2 mmol) of the material from Preparation 1 was added and the mixture stirred at room temperature for 1 hr. The mixture was diluted with 80 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried (MgSO₄), filtered and concentrated in vacuo. Chromatography (150 g of silica gel, 15% ethyl acetate/hexane) of the residue afforded 2.8 g (65%) of the title compound.

Analysis calculated for $C_{15}H_{17}BrO_3$: %C, 55.40; %H, 5.27. Found: %C, 55.69; %H, 5.26.

B. (1SR,2SR-2-carboxycycloprop-1-yl) (2-(3-bromophenyl)ethyl) ketone: A solution of 2.8 g (8.6 mmol) of the compound from Example 38A in 25 mL of ethanol and 9.5 mL of 1N sodium hydroxide was stirred 24 hr at room temperature, then concentrated in vacuo. The residue was dissolved in 50 mL of 10% sodium bisulfate and extracted four times with 50 mL each of ethyl acetate, then the combined organics were dried (MgSO₄), filtered and concentrated in vacuo to afford 2.3 g (89%) of the title compound.

C. 5SR- and 5RS-5-(1SR,2SR-2-carboxycyclopropan-1-yl)-5-(2-(3-bromophenyl)ethyl)imidazolidine-2,4-dione: A solution of 2.3 g (7.7 mmol) of the compound from Example 38B in 10 mL of ethanol was added to a solution of 2.5 g (38.4 mmol) of potassium cyanide and 6.7 g (69.2 mmol) of ammonium carbonate in 10 mL of water, then this mixture was heated to 55° C. for 24 hr. The mixture was cooled and added to 150 mL of 10% aqueous sodium bisulfate, and the resulting precipitate was filtered, washed three times with water, then recrystallized from water and acetone to afford 2.3 g (83%) of the title compound.

D. A solution of 2.3 g (6.2 mmol) of the compound from Example 38C and 9.8 g (30.9 mmol) of barium hydroxide in 50 mL of water was heated to 250° C. for 24 hr in a stainless steel high pressure reactor. The mixture was cooled and acidified to pH 2 with concentrated sulfuric acid, affording a solid that was filtered and washed with water. Cation exchange chromatography of the filtrate afforded a solid that was suspended in water and filtered, washed with water, acetone and ether and dried in vacuo at 60° C. to afford 0.4 g (19%) of the title compound.

Analysis calculated for $C_{15}H_{16}BrNO_4 \cdot 0.25\ H_2O$: %C, 48.50; %H, 4.80; %N, 4.04. Found: %C, 48.52; %H, 4.85; %N, 3.87.

Field Desorption Mass Spectrum: M+1=342.

EXAMPLE 39

Preparation of 2SR- and 2RS-2-amino-2-(1SR,2SR-2-carboxycyclopropan-1-yl)-3-phenoxypropanoic acid A. (Phenoxymethyl)tri-n-butylstannane: A solution of 11.4 g (26.5 mmol) of (iodomethyl)tri-n-butylstannane, 2.5 g (26.5 mmol) of phenol and 4.4 g (31.7 mmol) of potassium carbonate in 75 mL of THF was stirred 24 hr at room temperature, then an additional 3.5 g (25.3 mmol) of potassium carbonate and 1 g (10.6 mmol) of phenol were added and the mixture was then heated to reflux for 24 hr. The mixture was cooled, diluted with 150 mL of ether and washed once with 75 mL of water. The organic layer was separated and the aqueous layer extracted three times with 25 mL each of ether, then the combined organics were dried (MgSO₄), filtered and concentrated in vacuo. Chromatography (400 g of silica gel, hexane) of the residue afforded 4.7 g (44%) of the title compound.

B. (1SR,2SR-2-carbethoxycycloprop-1-yl) (phenoxymethyl) ketone: A solution of 2.1 g (11.8 mmol) of the material from Preparation 1, 4.7 g (11.8 mmol) of the compound from Example 39A and 0.05 g (0.04 mmol) of tetrakis(triphenylphosphine)palladium(0) in 35 mL of THF was heated to reflux for 4.5 hr, then treated with 50 mg (0.07 mmol) of bis(triphenylphosphine)palladium(II) dichloride and the mixture heated at reflux overnight. Another 50 mg (0.07 mmol) of bis(triphenylphosphine)palladium(II) dichloride and 0.6 g (3.4 mmol) of the material from Preparation 1 were added, and the mixture refluxed for 5 hr. The mixture was cooled, diluted with 80 mL of ether and washed with 50 mL of 10% aqueous sodium bisulfate, 50 mL of saturated aqueous sodium bicarbonate and 50 mL of 50% aqueous potassium fluoride. The organic layer was dried (MgSO₄), filtered and concentrated in vacuo. Chromatography (125 g of silica gel, 20% ethyl acetate/hexane) of the residue afforded 2.7 g (92%) of the title compound.

C. (1SR,2SR-2-carboxycycloprop-1-yl) (2-(3-bromophenyl)ethyl) ketone: A solution of 2.7 g (11 mmol) of the compound from Example 39B in 35 mL of ethanol and 12.1 mL of 1N sodium hydroxide was stirred 48 hr at room temperature, then concentrated in vacuo. The residue was dissolved in 25 mL of water and extracted twice with 25 mL of ether, then acidified with 25 mL of 10% sodium bisulfate and extracted four times with 50 mL each of ethyl acetate. The combined organics were dried (MgSO₄), filtered and concentrated in vacuo to afford 1.6 g (60%) of the title compound.

D. 5SR- and 5RS-5-(1SR,2SR-2-carboxycyclopropan-1-yl)-5-(phenoxymethyl)imidazolidine-2,4-dione: A solution of 1.6 g (7 mmol) of the compound from Example 39C in 8 mL of ethanol was added to a solution of 2.3 g (35.2 mmol) of potassium cyanide and 6.1 g (63.4 mmol) of ammonium carbonate in 8 mL of water, then this mixture was heated to 55° C. for 24 hr. The mixture was cooled and added to 150 mL of 10% aqueous sodium bisulfate, then extracted five times with 50 mL each of ethyl acetate. The combined organics were dried (MgSO₄), filtered and concentrated in vacuo. Recrystallization from water and acetone afforded 0.9 g (43%) of the title compound.

E. A solution of 0.9 g (3 mmol) of the compound from Example 39D and 4.8 g (15.2 mmol) of barium hydroxide in 25 mL of water was heated to 250° C. for 24 hr in a stainless steel high pressure reactor. The mixture was cooled and acidified to pH 3 with concentrated sulfuric acid, affording a solid that was filtered and washed with water. The filtrate was concentrated in vacuo to ~5 mL, and the resulting solid was filtered, washed with water, acetone and ether and dried in vacuo at 60° C. Recrystallization from water afforded 0.22 g (28%) of the title compound.

Analysis calculated for $C_{13}H_{15}NO_5$: %C, 58.86; %H, 5.70; %N, 5.28. Found: %C, 58.67; %H, 5.77; %N, 5.13.

Field Desorption Mass Spectrum: M=265.

EXAMPLE 40

Preparation of 2SR- and 2RS-2-amino-2-(1SR,2SR-2-carboxycyclopropan-1-yl)-3-cyclobutylpropanoic acid A. (1SR,2SR-2-carbethoxycycloprop-1-yl) ((cyclobutyl)methyl) ketone: A solution of 4.7 g (24.2 mmol) of (cyclobutyl)methyl iodide and 3.3 g (50.6 mmol) of zinc/copper couple in 66 mL of benzene and 8 mL of N,N-dimethylacetamide was stirred for 3 hr at 50° C., then treated with 0.6 g (0.5 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 66 mL of ethyl acetate and filtered through diatomaceous earth. The filtrate was washed with 150 mL of 10% aqueous sodium bisulfate, 150 mL of saturated aqueous sodium bicarbonate and 150 mL of saturated aqueous sodium chloride. The organic layer was dried ($MgSO_4$), filtered and concentrated in vacuo. Chromatography (200 g of silica gel, 10% ethyl acetate/hexane) of the residue afforded 3.3 g (71%) of the title compound.

Analysis calculated for $C_{12}H_{18}O_3$: %C, 68.55; %H, 8.63. Found: %C, 68.40; %H, 8.55.

B. (1SR,2SR-2-carboxycycloprop-1-yl) ((cyclobutyl)methyl) ketone: A solution of 3.3 g (15.7 mmol) of the compound from Example 40A in 35 mL of ethanol and 17.2 mL of 1N sodium hydroxide was stirred 24 hr at room temperature and 24 hr at 75° C., then concentrated in vacuo. The residue was dissolved in 35 mL of 1N hydrochloric acid and extracted four times with 35 mL each of ether. The combined organics were dried ($MgSO_4$), filtered and concentrated in vacuo to afford 2.4 g (82%) of the title compound.

C. 5SR- and 5RS-5-(1SR,2SR-2-carboxycyclopropan-1-yl)-5-((cyclobutyl)methyl)imidazolidine-2,4-dione: A solution of 2.4 g (12.9 mmol) of the compound from Example 40B in 20 mL of ethanol was added to a solution of 2.1 g (32.4 mmol) of potassium cyanide and 4.5 g (58.3 mmol) of ammonium carbonate in 20 mL of water, then this mixture was placed in a 3.5×20 cm pressure tube, sealed with a #15 Teflon screw plug and heated to 150° C. for 24 hr. The mixture was cooled, vented, added to 150 mL of 1N hydrochloric acid, and the mixture was then cooled overnight at 0° C. The resulting solid was filtered and washed three times with water. Recrystallization from acetone/water afforded 0.8 g (24%) of the title compound.

D. A solution of 0.8 g (3.1 mmol) of the compound from Example 40C in 25 mL of 5N sodium hydroxide was heated to 250° C. for 24 hr in a stainless steel high pressure reactor. The mixture was cooled and acidified to pH 6 with concentrated hydrochloric acid. Cation exchange chromatography of this solution gave a solid that was suspended in water, filtered, washed with water, acetone and ether and dried in vacuo at 60° C. to afford 0.09 g (10%) of the title compound.

Analysis calculated for $C_{11}H_{17}NO_4$: %C, 58.14; %H, 7.54; %N, 6.16. Found: %C, 57.89; %H, 7.60; %N, 6.04.

Field Desorption Mass Spectrum: M+1=228.

EXAMPLE 41

Preparation of 2SR- and 2RS-2-amino-2-(1SR,2SR-2-carboxycyclopropan-1-yl)-3-cyclopentylpropanoic acid A. (1SR,2SR-2-carbethoxycycloprop-1-yl) ((cyclopentyl)methyl) ketone: A solution of 5.1 g (24.2 mmol) of (cyclopentyl)methyl iodide and 3.3 g (50.6 mmol) of zinc/copper couple in 66 mL of benzene and 8 mL of N,N-dimethylacetamide was stirred for 3 hr at 50° C., then treated with 0.5 g (0.4 mmol) of tetrakis(triphenylphosphine)palladium(0) and heated for 5 min more. The heating bath was removed, 3.8 g (22 mmol) of the material from Preparation 1 was added and the mixture stirred at room temperature for 1 hr. The mixture was diluted with 66 mL of ethyl acetate and filtered through diatomaceous earth. The filtrate was washed with 150 mL of 10% aqueous sodium bisulfate, 150 mL of saturated aqueous sodium bicarbonate and 150 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.4 g (49%) of the title compound.

Analysis calculated for $C_{13}H_{20}O_3$: %C, 69.61; %H, 8.99. Found: %C, 70.06; %H, 8.69.

B. (1SR,2SR-2-carboxycycloprop-1-yl) ((cyclopentyl)methyl) ketone: A solution of 2.4 g (10.7 mmol) of the compound from Example 41A in 25 mL of ethanol and 11.8 mL of 1N sodium hydroxide was stirred 24 hr at room temperature and 24 hr at 75° C., then concentrated in vacuo. The residue was dissolved in 40 mL of water, extracted twice with 25 mL each of ether, then acidified to pH 1 with 50 mL of 10% aqueous sodium bisulfate and extracted three times with 35 mL each of ether. The combined organics were dried ($MgSO_4$), filtered and concentrated in vacuo to afford 1.5 g (71%) of the title compound.

C. 5SR- and 5RS-5-(1SR,2SR-2-carboxycyclopropan-1-yl)-5-((cyclopentyl)methyl)imidazolidine-2,4-dione: A solution of 1.5 g (7.6 mmol) of the compound from Example 41B in 12 mL of ethanol was added to a solution of 2.5 g (38.2 mmol) of potassium cyanide and 5.4 g (68.8 mmol) of ammonium carbonate in 12 mL of water, then this mixture was heated to reflux for 24 hr. At this time an additional 2.5 g (38.2 mmol) of potassium cyanide and 5.4 g (68.8 mmol) of ammonium carbonate were added and the mixture was heated at 60° C. for 24 hr. The mixture was cooled and added to 150 mL of 10% aqueous sodium bisulfate. The resulting mixture was allowed to stand overnight at room temperature, then the solid was filtered, washed with water and dried in vacuo at 60° C. to afford 1.0 g (50%) of the title compound.

D. A solution of 1.0 g (3.8 mmol) of the compound from Example 41C and 5.9 g (18.8 mmol) of barium hydroxide in 13 mL of water was heated to reflux for 72 hr. The mixture was cooled and treated with 1 mL (18 mmol) of concentrated sulfuric acid. The resulting solid was filtered and washed three times with water. Cation exchange chromatography of the filtrate gave a solid that was suspended in water, filtered, washed with water, acetone and ether and dried in vacuo at 60° C. to afford 0.16 g (18%) of the title compound.

Analysis calculated for $C_{12}H_{19}NO_4$: %C, 59.73; %H, 7.94; %N, 5.80. Found: %C, 59.74; %H, 8.08; %N, 5.90.

Field Desorption Mass Spectrum: M+1=242.

EXAMPLE 42

Preparation of 2SR- and 2RS-2-amino-2-(1SR,2SR-2-carboxycyclopropan-1-yl)-3-((4-carboxy)phenyl)propanoic acid A. (1SR,2SR-2-carbethoxycycloprop-1-yl) ((4-cyanophenyl)methyl) ketone: A 0° C. solution of 3.5 g (18 mmol) (4-cyanophenyl)methyl bromide and 1.8 g (27.6 mmol) of zinc/copper couple in 36 mL of benzene and 4 mL of N,N-dimethylacetamide was stirred for 3 hr, then treated with 0.5 g (0.5 mmol) of tetrakis(triphenylphosphine)palladium(0), 2.1 g (12 mmol) of the material from Preparation 1 and warmed to room temperature. After 30 min, the reaction was diluted with 40 mL of ethyl acetate and washed with 25 mL of 10% aqueous sodium bisulfate, 25 mL of saturated aqueous sodium bicarbonate and 25 mL of saturated aqueous sodium chloride. The organic layer was dried (MgSO$_4$), filtered and concentrated in vacuo. Chromatography (200 g of silica gel, 25% ethyl acetate/hexane) of the residue afforded 2.4 g (77%) of the title compound.

Analysis calculated for $C_{15}H_{15}NO_3$: %C, 70.02; %H, 5.88; %N, 5.44. Found: %C, 69.74; %H, 5.72; %N, 5.14.

B. (1SR,2SR-2-carboxycycloprop-1-yl) ((4-cyanophenyl)methyl) ketone: A solution of 2.3 g (9.0 mmol) of the compound from Example 42A in 20 mL of ethanol and 9.9 mL of 1N sodium hydroxide was stirred 24 hr at room temperature, then concentrated in vacuo. The residue was dissolved in 40 mL of water, extracted twice with 25 mL each of ether, then acidified to pH 2 with 50 mL of 10% aqueous sodium bisulfate and extracted three times with 35 mL each of ethyl acetate. The combined organics were dried (MgSO$_4$), filtered and concentrated in vacuo, the residue was then suspended in 50% ethyl acetate/hexane and filtered to afford 1.3 g (61%) of the title compound.

C. 5SR- and 5RS-5-(1SR,2SR-2-carboxycyclopropan-1-yl)-5-((4-carboxyphenyl)methyl)imidazolidine-2,4-dione: A solution of 1.3 g (5.5 mmol) of the compound from Example 42B in 10 mL of ethanol was added to a solution of 0.9 g (13.7 mmol) of potassium cyanide and 1.9 g (24.7 mmol) of ammonium carbonate in 10 mL of water, then this mixture was placed in a 3.5×20 cm pressure tube, sealed with a #15 Teflon screw plug and heated to 90° C. for 24 hr. The mixture was cooled, vented, added to 100 mL of 10% aqueous sodium bisulfate and extracted three times with 75 mL each of ethyl acetate. The combined organics were dried (MgSO$_4$), filtered and concentrated in vacuo. A solution of this residue in 50 mL of 1N sodium hydroxide was heated to reflux for 48 hr, then cooled, acidified to pH 7 with concentrated hydrochloric acid, and anion exchange chromatography of this solution then afforded 0.18 g (11%) of the title compound.

D. A solution of 0.18 g (0.6 mmol) of the compound from Example 42C in 10 mL of 5N sodium hydroxide was placed in a 3.5×20 cm pressure tube, sealed with a #15 Teflon screw plug and heated to 150° C. for 24 hr. The mixture was cooled, vented, acidified to pH 4 with concentrated hydrochloric acid, then filtered, the precipitate washed three times with 10% pyridine/water and the filtrate concentrated in vacuo. Cation exchange chromatography of this residue afforded a solid that was suspended in water and filtered, washed with water, acetone and ether and dried in vacuo at 60° C. to afford 0.04 g (22%) of the title compound.

Analysis calculated for $C_{14}H_{15}NO_6 \cdot 0.5\ H_2O$: %C, 55.63; %H, 5.34; %N, 4.63. Found: %C, 55.65; %H, 5.05; %N, 4.64.

Field Desorption Mass Spectrum: M+1=294.

EXAMPLE 43

Preparation of 2SR- and 2RS-2-amino-2-(1SR,2SR-2-carboxycyclopropan-1-yl)-2-(indan-2-yl)ethanoic acid A. (1SR,2SR-2-carbethoxycycloprop-1-yl) (indan-2-yl) ketone: A solution of 4.9 g (20.2 mmol) of 2-iodoindane and 2.0 g (31.0 mmol) of zinc/copper couple in 66 mL of benzene and 8 mL of N,N-dimethylacetamide was stirred for 30 min at 60° C., then treated with 0.6 g (0.5 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 66 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.8 g (81%) of the title compound.

B. (1SR,2SR-2-carboxycycloprop-1-yl) (indan-2-yl) ketone: A solution of 2.7 g (10.4 mmol) of the compound from Example 43A in 23 mL of ethanol and 11.4 mL of 1N sodium hydroxide was stirred 24 hr at room temperature, then concentrated in vacuo. The residue was dissolved in 25 mL of water and extracted twice with 25 mL each of ether, then the aqueous layer was adjusted to pH 2 with concentrated hydrochloric acid and extracted four times with 35 mL each of ether. The combined organics were dried (MgSO$_4$), filtered and concentrated in vacuo to afford 1.9 g (79%) of the title compound.

C. 5SR- and 5RS-5-(1SR,2SR-2-carboxycyclopropan-1-yl)-5-(indan-2-yl)imidazolidine-2,4-dione: A solution of 2.4 g (12.9 mmol) of the compound from Example 43B in 15 mL of ethanol was added to a solution of 1.4 g (21.7 mmol) of potassium cyanide and 3.0 g (39.1 mmol) of ammonium carbonate in 15 mL of water, then this mixture was placed in a 3.5×20 cm pressure tube, sealed with a #15 Teflon screw plug and heated to 150° C. for 24 hr. The mixture was cooled, vented, added to 200 mL of 1N hydrochloric acid, then extracted four times with 75 mL each of ether. The combined organics were dried (MgSO$_4$), filtered and concentrated in vacuo. The residue was dissolved in 50 mL of methanol, concentrated in vacuo, then dissolved in 50 mL of chloroform and concentrated in vacuo to afford 2.6 g (100%) of the title compound.

D. A solution of 0.8 g (3.1 mmol) of the compound from Example 43C in 30 mL of 5N sodium hydroxide was heated to 250° C. for 24 hr in a stainless steel high pressure reactor. The mixture was cooled and acidified to pH 7 with concentrated hydrochloric acid. Cation exchange chromatography of this solution gave a solid that was suspended in water, filtered, washed with water, acetone and ether and dried in vacuo at 60° C. to afford 0.5 g (21%) of the title compound.

Analysis calculated for $C_{15}H_{17}NO_4$: %C, 65.44; %H, 6.22; %N, 5.09. Found: %C, 65.47; %H, 6.07; %N, 5.17.

Field Desorption Mass Spectrum: M=275.

EXAMPLE 44

Preparation of 2SR- and 2RS-2-amino-2-(1SR,2SR-2-carboxycyclopropan-1-yl)-4-(cyclohexyl) butanoic acid A. 5SR- and 5RS-5-(1SR,2SR-2-carboxycyclopropan-1-yl)-5-(2-(cyclohexyl)ethyl)imidazolidine-2,4-dione: A solution of 2.5 g (8.7 mmol) of the compound from Example 2B in 145 mL of ethanol was hydrogenated with 2.5 g of 5% rhodium on carbon at 60° C. and 60 psi for 24 hr. The mixture was cooled, filtered through diatomaceous earth and concentrated in vacuo. The residue was dissolved in ethyl acetate, using enough ethanol to achieve solution, and then filtered through diatomaceous earth. Concentration in vacuo of the filtrate afforded 2.1 g (82%) of the title compound.

B. A solution of 2.5 g (8.4 mmol) of the compound from Example 44A and 13.2 g (41.8 mmol) of barium hydroxide in 30 mL of water was heated to 250° C. for 24 hr in a stainless steel high pressure reactor. The mixture was cooled and acidified with 2.3 mL (41.8 mmol) of concentrated sulfuric acid, affording a solid that was filtered and washed with water and 10% pyridine/water. The filtrate was concentrated in vacuo, then cation exchange chromatography of the residue afforded a solid that was suspended in water and filtered, washed with water, acetone and ether and dried in vacuo at 60° C. Recrystallization from water afforded 1.0 g (44%) of the title compound.

Analysis calculated for $C_{14}H_{23}NO_4 \cdot 0.25\ H_2O$: %C, 61.41; %H, 8.65; %N, 5.11. Found: %C, 61.32; %H, 8.79; %N, 4.95.

Field Desorption Mass Spectrum: M+1=270.

EXAMPLE 45

Preparation of 2SR- and 2RS-2-amino-2-(1SR,2SR-2-carboxycyclopropan-1-yl)-2-(piperidin-4-yl) butanoic acid A. (1SR,2SR-2-carbethoxycycloprop-1-yl) ((N-t-butoxycarbonylpiperidin-4-yl)ethyl) ketone: A solution of 6.8 g (20.2 mmol) of 4-(iodoethyl)-N-(t-butoxycarbonyl) piperidine (Villalobos, et al., *J. Med. Chem.* 1994, 37, 2721) and 2.0 g (31.0 mmol) of zinc/copper couple in 66 mL of benzene and 8 mL of N,N-dimethylacetamide was stirred for 3 hr at 60° C., then treated with 0.6 g (0.5 mmol) of tetrakis)triphenylphosphine)palladium(0) and heated for 5 min more. The heating bath was removed, 2.4 g (13.5 mmol) of the material from Preparation 1 was added and the mixture stirred at room temperature for 24 hr, then at 60° C. for 24 hr, then room temperature for 72 hr. The mixture was diluted with 66 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 25% ethyl acetate/hexane) of the residue afforded 1.0 g (21%) of the title compound.

B. (1SR,2SR-2-carboxycycloprop-1-yl) ((N-t-butoxycarbonylpiperidin-4-yl)ethyl) ketone: A solution of 1.0 g (2.8 mmol) of the compound from Example 45A in 6 mL of ethanol and 3 mL of 1N sodium hydroxide was stirred 24 hr at room temperature, then concentrated in vacuo. The residue was dissolved in 10 mL of water and extracted with 10 mL of ether, then the aqueous layer was adjusted to pH 2 with concentrated hydrochloric acid and extracted three times with 20 mL each of ether. The combined organics were dried (MgSO$_4$), filtered and concentrated in vacuo to afford 1.0 g (100%) of the title compound.

C. 5SR- and 5RS-5-(1SR,2SR-2-carboxycyclopropan-1-yl)-5-((N-t-butoxycarbonylpiperidin-4-yl)ethyl) imidazolidine-2,4-dione: A solution of 1.0 g (3 mmol) of the compound from Example 45B in 9 mL of ethanol was added to a solution of 0.5 g (7.7 mmol) of potassium cyanide and 1.1 g (13.8 mmol) of ammonium carbonate in 9 mL of water, then this mixture was placed in a 3.5×20 cm pressure tube, sealed with a #15 Teflon screw plug and heated to 120° C. for 24 hr. The mixture was cooled, vented, added to 150 mL of 10% aqueous sodium bisulfate, then extracted four times with 50 mL each of ether. The combined organics were dried (MgSO$_4$), filtered and concentrated in vacuo to afford 0.6 g (52%) of the title compound.

D. A solution of 0.6 g (1.5 mmol) of the compound from Example 45C and 2.4 g (7.5 mmol) of barium hydroxide in 10 mL of water was heated to reflux for 24 hr. The mixture was cooled and treated with 0.8 mL (14.4 mmol) of concentrated sulfuric acid. The resulting solid was filtered and washed four times with water. Cation exchange chromatography of the filtrate gave a solid that was suspended in water, filtered, washed with water, acetone and ether and dried in vacuo at 60° C. to afford 0.25 g (61%) of the title compound. Analysis calculated for $C_{13}H_{22}N_2O_4$: %C, 65.44; %H, 6.22; %N, 5.09. Found: %C, 65.47; %H, 6.07; %N, 5.17.

Field Desorption Mass Spectrum: M=275.

EXAMPLE 46

Preparation of 2SR- and 2RS-2-amino-2-(1SR,2SR-2-carboxycyclopropan-1-yl)-4,4-di(4,4'-dichloro) phenylbutanoic acid A. (1SR,2SR-2-carbethoxycycloprop-1-yl) (2,2-((4,4'-dichloro)phenyl)ethyl) ketone: A solution of 5.6 g (114.5 mmol) of 2,2-((4,4'-dichloro)phenyl)-1-iodoethane and 2.0 g (31.0 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 60 mL of ethyl acetate and filtered through diatomaceous earth. The filtrate was washed with 100 mL of 1N aqueous hydrochloric acid, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 20% ethyl acetate/hexane) of the residue afforded 3.8 g (73%) of the title compound.

Analysis calculated for $C_{21}H_{20}O_3Cl_2$: %C, 64.46; %H, 5.15. Found: %C, 64.28; %H, 5.07.

B. (1SR,2SR-2-carboxycycloprop-1-yl) (2,2-((4,4'-dichloro)phenyl)ethyl) ketone: A solution of 3.7 g (9.5 mmol) of the compound from Example 46A in 20 mL of ethanol and 10.4 mL of 1N sodium hydroxide was stirred overnight at room temperature, then concentrated in vacuo. The residue was dissolved in 20 mL of in hydrochloric acid and then extracted three times with 20 mL each of ethyl acetate. The combined organics were dried (MgSO$_4$), filtered and concentrated in vacuo to afford 2.6 g (76%) of the title compound.

C. 5SR- and 5RS-5-(1SR,2SR-2-carboxycyclopropan-1-yl)-5-(2,2-((4,4'-dichloro)phenyl)ethyl)imidazolidine-2,4-dione: A solution of 2.6 g (7.2 mmol) of the compound from Example 46B in 12 mL of ethanol was added to a solution of 2.3 g (35.8 mmol) of potassium cyanide and 5.0 g (64.4 mmol) of ammonium carbonate in 12 mL of water, then this mixture was heated to 55° C. for 24 hr. Another 2.3 g (35.8 mmol) of potassium cyanide and 5.0 g (64.4 mmol) of ammonium carbonate was added and the mixture was heated to 55° C. for an additional 24 hr. The mixture was cooled and added to 200 mL of 10% aqueous sodium bisulfate. The resulting mixture was allowed to stand at room temperature, then the solid was filtered and recrystallization from acetone and water afforded 2.2 g (69%) of the title compound.

Analysis calculated for $C_{21}H_{18}N_2O_4Cl_2$: %C, 58.21; %H, 4.19, N, 6.47. Found: %C, 58.48; %H, 4.41, %N, 6.26.

D. A solution of 2.2 g (4.9 mmol) of the compound from Example 46C and 7.8 g (24.7 mmol) of barium hydroxide in 20 mL of water was heated to 250° C. for 24 hr in a stainless steel high pressure reactor. The mixture was cooled and acidified to pH 7 with 1.4 mL (24.7 mmol) of concentrated sulfuric acid. The resulting solid was filtered and washed three times with 10 mL each of 10% pyridine/water. Cation exchange chromatography of the filtrate afforded a solid that was suspended in water and filtered, washed with water and dried in vacuo at 60° C. to afford 0.32 g (16%) of the title compound.

Analysis calculated for $C_{20}H_{19}NO_4Cl_2 \cdot 0.75\ H_2O$: %C, 56.95; %H, 4.9; %N, 3.32. Found: %C, 56.85; %H, 4.62; %N, 3.32.

Field Desorption Mass Spectrum: M−1=407.

EXAMPLE 47

Preparation of 2SR- and 2RS-2-amino-2-(1SR,2SR-2-carboxycyclopropan-1-yl)-4-(2,4-dichlorophenyl)butanoic acid A. (1SR,2SR-2-carbethoxycycloprop-1-yl) (2-(2,4-dichlorophenyl)ethyl) ketone: A solution of 4.4 g (14.5 mmol) of 1-iodo-2-(2,4-dichlorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 60 mL of ethyl acetate and filtered through diatomaceous earth. The filtrate was washed with 100 mL of 1N aqueous hydrochloric acid, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 10% ethyl acetate/hexane) of the residue afforded 1.9 g (45%) of the title compound.

Analysis calculated for $C_{15}H_{16}O_3Cl_2$: %C, 57.16; %H, 5.12. Found: %C, 57.41; %H, 5.09.

B. (1SR,2SR-2-carboxycycloprop-1-yl) (2-(2,4-dichlorophenyl)ethyl) ketone: A solution of 1.8 g (5.7 mmol) of the compound from Example 47A in 12 mL of ethanol and 6.3 mL of 1N sodium hydroxide was stirred 24 hr at room temperature, then concentrated in vacuo. The residue was dissolved in 20 mL of water, extracted three times with 10 mL each of ether, then brought to pH 1 with concentrated hydrochloric acid. The resulting solution was extracted three times with 10 mL each of ethyl acetate, then the combined organics were dried (MgSO$_4$), filtered and concentrated in vacuo at 60° C. to afford 1.3 g (78%) of the title compound.

C. 5SR- and 5RS-5-(1SR,2SR-2-carboxycyclopropan-1-yl)-5-(2-(2,4-dichlorophenyl)ethyl)imidazolidine-2,4-dione: A solution of 1.3 g (4.5 mmol) of the compound from Example 47B in 10 mL of ethanol was added to a solution of 1.45 g (22.3 mmol) of potassium cyanide and 3.1 g (40.1 mmol) of ammonium carbonate in 10 mL of water, then this mixture was heated to 55° C. for 24 hr. The mixture was cooled and added to 100 mL of 10% aqueous sodium bisulfate. The resulting mixture was allowed to stand at room temperature, then the solid was filtered, and recrystallization from acetone and water afforded 1.2 g (73%) of the title compound.

Analysis calculated for $C_{15}H_{14}N_2O_4Cl_2$: %C, 50.44; %H, 3.95, N, 7.84. Found: %C, 50.66; %H, 4.19, %N, 7.56.

D. A solution of 0.52 g (1.4 mmol) of the compound from Example 47C and 2.3 g (7.2 mmol) of barium hydroxide in 20 mL of water was heated to 250° C. for 24 hr in a stainless steel high pressure reactor. The mixture was cooled and acidified to pH 7 with 0.4 mL (7.2 mmol) of concentrated sulfuric acid. The resulting solid was filtered and washed three times with 10 mL each of 10% pyridine/water. Cation exchange chromatography of the filtrate afforded a solid that was suspended in water and filtered, washed with water and dried in vacuo at 60° C. to afford 0.19 g (41%) of the title compound.

Analysis calculated for $C_{14}H_{15}NO_4Cl_2$: %C, 50.62; %H, 4.55; N, 4.22. Found: %C, 50.92; %H, 4.62; %N, 4.30.

Field Desorption Mass Spectrum: M+2=334.

EXAMPLE 48

Preparation of 2SR- and 2RS-2-amino-2-(1SR,2SR-2-carboxycyclopropan-1-yl)-4-(3,4-dichlorophenyl) butanoic acid A. (1SR,2SR-2-carbethoxycycloprop-1-yl) (2-(3,4-dichlorophenyl)ethyl) ketone: A solution of 4.4 g (14.5 mmol) of 1-iodo-2-(3,4-dichlorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 60 mL of ethyl acetate and filtered through diatomaceous earth. The filtrate was washed with 100 mL of 1N aqueous hydrochloric acid, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 10% ethyl acetate/hexane) of the residue afforded 2.4 g (57%) of the title compound.

Analysis calculated for $C_{15}H_{16}O_3Cl_2$: %C, 57.16; %H, 5.12. Found: %C, 57.39; %H, 5.06.

B. (1SR,2SR-2-carboxycycloprop-1-yl) (2-(3,4-dichlorophenyl)ethyl) ketone: A solution of 2.3 g (7.3 mmol) of the compound from Example 48A in 16 mL of ethanol and 8.0 mL of 1N sodium hydroxide was stirred 24 hr at room temperature, then concentrated in vacuo. The residue was dissolved in 20 mL of water, extracted three times with 10 mL each of ether, then brought to pH 1 with concentrated hydrochloric acid. The resulting solution was extracted three times with 10 mL each of ethyl acetate, then the combined organics were dried (MgSO$_4$), filtered and concentrated in vacuo at 60° C. to afford 1.6 g (76%) of the title compound.

C. 5SR- and 5RS-5-(1SR,2SR-2-carboxycyclopropan-1-yl)-5-(2-(3,4-dichlorophenyl)ethyl)imidazolidine-2,4-dione: A solution of 1.6 g (5.6 mmol) of the compound from Example 48B in 10 mL of ethanol was added to a solution of 1.8 g (27.9 mmol) of potassium cyanide and 3.9 g (50.1 mmol) of ammonium carbonate in 10 mL of water, then this mixture was heated to 5° C. for 24 hr. The mixture was cooled and added to 100 mL of 10% aqueous sodium bisulfate. The resulting mixture was allowed to stand at room temperature, then the solid was filtered, and recrystallization from acetone and water afforded 1.4 g (69%) of the title compound. Analysis calculated for $C_{15}H_{14}N_2O_4Cl_2$: %C, 50.44; %H, 3.95, N, 7.84. Found: %C, 50.72; %H, 4.02, %N, 7.75.

D. A solution of 1.3 g (3.6 mmol) of the compound from Example 48C and 5.7 g (18.2 mmol) of barium hydroxide in 20 mL of water was heated to 250° C. for 24 hr in a stainless steel high pressure reactor. The mixture was cooled and acidified to pH 7 with 1.0 mL (18.2 mmol) of concentrated sulfuric acid. The resulting solid was filtered and washed three times with 10 mL each of 10% pyridine/water. Cation exchange chromatography of the filtrate afforded a solid that was suspended in water and filtered, washed with water and dried in vacuo at 60° C. to afford 0.19 g (41%) of the title compound.

Analysis calculated for $C_{14}H_{15}NO_4Cl_2 \cdot 0.25\ H_2O$: %C, 49.94; %H, 4.64; %N, 4.16. Found: %C, 50.35; %H, 4.51; %N, 4.26.

Field Desorption Mass Spectrum: M=332.

EXAMPLE 49

Preparation of 2SR- and 2RS-2-amino-2-(1SR,2SR-2-carboxycyclopropan-1-yl)-4-(4-biphenyl) butanoic acid A. (1SR,2SR-2-carbethoxycycloprop-1-yl) (2-(4-biphenyl)ethyl) ketone: A solution of 2.4 g (13.5 mmol) of 1-iodo-2-(4-biphenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 60 mL of ethyl acetate and filtered through diatomaceous earth. The filtrate was washed with 100 mL of 1N aqueous hydrochloric acid, 100 mL of saturated aqueous sodium bicarbonate and 100 mL of saturated aqueous sodium chloride. The organic layer was dried ($MgSO_4$), filtered and concentrated in vacuo. Chromatography (200 g of silica gel, 10% ethyl acetate/hexane) of the residue afforded 1.6 g (36%) of the title compound.

Analysis calculated for $C_{21}H_{22}O_3$: %C, 78.23; %H, 6.88. Found: %C, 77.96; %H, 6.89.

B. (1SR,2SR-2-carboxycycloprop-1-yl) (2-(4-biphenyl)ethyl) ketone: A solution of 1.45 g (4.5 mmol) of the compound from Example 49A in 10 mL of ethanol and 4.9 mL of 1N sodium hydroxide was stirred 24 hr at room temperature, then concentrated in vacuo. The residue was dissolved in 20 mL of 1N hydrochloric acid and a precipitate forms. The white solid was filtered and washed three times with 5 mL of water, then dried in vacuo at 60° C. to afford 1.1 g (83%) of the title compound.

C. 5SR- and 5RS-5-(1SR,2SR-2-carboxycyclopropan-1-yl)-5-(2-(4-biphenyl)ethyl)imidazolidine-2,4-dione: A solution of 1.1 g (3.7 mmol) of the compound from Example 49B in 12 mL of ethanol was added to a solution of 1.2 g (18.7 mmol) of potassium cyanide and 2.6 g (33.6 mmol of ammonium carbonate in 12 mL of water, then this mixture was heated to 55° C. for 24 hr. The mixture was cooled and added to 150 mL of 10% aqueous sodium bisulfate. The resulting mixture was allowed to stand at room temperature, then the solid was filtered, and recrystallization from acetone and water afforded 1.0 g (74%) of the title compound.

Analysis calculated for $C_{21}H_{20}N_2O_4$: %C, 69.22; %H, 5.53, %N, 7.69. Found: %C, 69.25; %H, 5.63, %N, 7.63.

D. A solution of 1.0 g (2.7 mmol) of the compound from Example 49C and 4.3 g (13.7 mmol) of barium hydroxide in 20 mL of water was heated to 250° C. for 24 hr in a stainless steel high pressure reactor. The mixture was cooled and acidified to pH 7 with 0.76 mL (13.7 mmol) of concentrated sulfuric acid. The resulting solid was filtered and washed three times with 10 mL each of 10% pyridine/water. Cation exchange chromatography of the filtrate afforded a solid that was suspended in water and filtered, washed with water and dried in vacuo at 60° C. to afford 0.021 g (2%) of the title compound.

Analysis calculated for $C_{20}H_{21}NO_4 \cdot 0.65\ H_2O \cdot 0.25\ C_5H_5N$: %C, 68.82; %H, 6.40; %N, 4.72. Found: %C, 68.49; %H, 5.89; %N, 5.12.

Field Desorption Mass Spectrum: M=339.

EXAMPLE 50

Preparation of 2SR- and 2RS-2-amino-2-(1SR,2SR-2-carboxycyclopropan-1-yl)-4-(2,3,4,5,6-pentafluorophenyl) butanoic acid A. (1SR,2SR-2-carbethoxycycloprop-1-yl) (2-(4-biphenyl)ethyl) ketone: A solution of 4.6 g (14.5 mmol) of 1-iodo-2-(2,3,4,5,6-pentafluorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 60 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.5 g (55%) of the title compound.

Analysis calculated for $C_{15}H_{13}O_3F_5 \cdot 0.5\ CH_2Cl_2$: %C, 49.16; %H, 3.73. Found: %C, 48.67; %H, 3.5.

B. (1SR,2SR-2-carboxycycloprop-1-yl) (2-(2,3,4,5,6-pentafluorophenyl)ethyl) ketone: A solution of 2.4 g (7.1 mmol) of the compound from Example 50A in 15 mL of ethanol and 7.8 mL of 1N sodium hydroxide was stirred 24 hr at room temperature, then concentrated in vacuo. The residue was dissolved in 25 mL of 1N hydrochloric acid and then extracted three times with 10 mL each of ethyl acetate. The combined organics were dried ($MgSO_4$), filtered and concentrated in vacuo to afford 2.0 g (91%) of the title compound.

C. 5SR- and 5RS-5-(1SR,2SR-2-carboxycyclopropan-1-yl)-5-(2-(2,3,4,5,6-pentafluorophenyl)ethyl)imidazolidine-2,4-dione: A solution of 2.0 g (6.5 mmol) of the compound from Example 50B in 10 mL of ethanol was added to a solution of 2.1 g (32.4 mmol) of potassium cyanide and 4.5 g (58.4 mmol) of ammonium carbonate in 10 mL of water, then this mixture was heated to 55° C. for 24 hr. The mixture was cooled and added to 100 mL of 10% aqueous sodium bisulfate. The resulting mixture was allowed to stand at room temperature, then the solid was filtered, and recrystallization from acetone and water afforded 1.5 g (62%) of the title compound.

D. A solution of 1.5 g (4.0 mmol) of the compound from Example 50C and 6.3 g (20.2 mmol) of barium hydroxide in 15 mL of water was heated to 200° C. for 24 hr in a stainless steel high pressure reactor. The mixture was cooled and acidified to pH 7 with 4N sulfuric acid. The resulting solution was heated for 1 hr, then filtered and washed three times with 10 mL each water. Cation exchange chromatography of the filtrate afforded a solid that was suspended in water and filtered, washed with water, acetone, and ether and dried in vacuo at 60° C. to afford 0.44 g (31%) of the title compound.

Analysis calculated for $C_{14}H_{12}NO_4F_5$: %C, 47.60 %H, 3.42; %N, 3.97. Found: %C, 47.78; %H, 3.61; %N, 4.08.

Field Desorption Mass Spectrum: M−1=352.

EXAMPLE 51

Preparation of 2SR- and 2RS-2-amino-2-(1SR,2SR-2-carboxycyclopropan-1-yl)-4-benzyl-5-phenylpentanoic acid A. (1SR,2SR-2-carbethoxycycloprop-1-yl) (2-benzyl-3-(phenyl)prop-1-yl) ketone: A solution of 4.8 g (14.5 mmol) of 2-benzyl(3-iodoprop-1-yl)benzene and 2.0 g (31.0 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 60 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.0 g (42%) of the title compound.

Analysis calculated for $C_{23}H_{26}O_3$: %C, 78.83; %H, 7.48. Found: %C, 79.09 %H, 7.42.

B. (1SR,2SR-2-carboxycycloprop-1-yl) (2-benzyl-3-(phenyl)prop-1-yl) ketone: A solution of 2.0 g (5.7 mmol) of the compound from Example 51A in 13 mL of ethanol and 6.3 mL of 1N sodium hydroxide was stirred overnight at room temperature, then concentrated in vacuo. The residue was dissolved in 25 mL of 1N hydrochloric acid, extracted three times with 10 mL each of ethyl acetate. The combined organics were dried ($MgSO_4$), filtered and concentrated in vacuo to afford 1.7 g (92%) of the title compound.

C. 5SR- and 5RS-5-(1SR,2SR-2-carboxycyclopropan-1-yl)-5-(2-benzyl-3-phenylprop-1-yl)imidazolidine-2,4-dione: A solution of 1.7 g (5.3 mmol) of the compound from Example 51B in 20 mL of ethanol was added to a solution of 1.7 g (26.4 mmol) of potassium cyanide and 3.7 g (47.7 mmol) of ammonium carbonate in 20 mL of water, then this mixture was heated to 55° C. for 24 hr. The mixture was cooled and added to 150 mL of 10% aqueous sodium bisulfate, then extracted three times with 50 mL each of ethyl acetate. The combined organics were dried ($MgSO_4$), filtered and concentrated in vacuo to afford 1.7 g (81%) of the title compound.

D. A solution of 1.6 g (4.2 mmol) of the compound from Example 51C and 6.7 g (21.4 mmol) of barium hydroxide in 15 mL of water was heated to 250° C. for 24 hr in a stainless steel high pressure reactor. The mixture was cooled and acidified to pH 7 with 1.2 mL (21.4 mmol) concentrated sulfuric acid. The resulting solid was filtered and washed three times with 10 mL each of hot 10% pyridine/water. Cation exchange chromatography of the filtrate afforded a solid that was suspended in water and filtered, washed with water and dried in vacuo at 60° C. to afford 0.16 g (10%) of the title compound.

Analysis calculated for $C_{22}H_{25}NO_4 \cdot 0.75\ H_2O$: %C, 69.36; %H, 7.01%N, 3.68. Found: %C, 69.71; %H, 6.71; %N, 3.70.

Field Desorption Mass Spectrum: M=368.

EXAMPLE 52

Preparation of 2SR- and 2RS-2-amino-2-(1SR,2SR-2-carboxycyclopropan-1-yl)-4-(2,3-dimethoxyphenyl) butanoic acid A. (1SR,2SR-2-carbethoxycycloprop-1-yl) (2-(2,3-dimethoxyphenyl)ethenyl) ketone: A solution of 2.0 g (7.6 mmol) of the material from Preparation 4 in 5 mL dry tetrahydrofuran was added to a suspension of 0.3 g (7.6 mmol) sodium hydride in 15 mL of dry tetrahydrofuran, and the mixture was stirred for 20 min at room temperature. A solution of 1.3 g (7.6 mmol) of 2,3-dimethoxybenzaldehyde in 5 mL dry tetrahydrofuran was added and the mixture stirred for 4 hr at room temperature, then 0.1 g (2.5 mmol) sodium hydride was added and the mixture stirred for 18 hr more at room temperature. The mixture was added to 30 mL of water and 15 mL of ether, the organic layer separated and the aqueous layer extracted three times with 10 mL each of ether. The combined organics were dried ($MgSO_4$), filtered and concentrated in vacuo to afford 2.0 g (90%) of the title compound.

B. (1SR,2SR-2-carbethoxycycloprop-1-yl) (2-(2,3-dimethoxyphenyl)ethyl) ketone: A solution of 2.0 g (6.6 mmol) of the compound from Example 52A in 25 mL of ethanol and 0.4 g of 5% palladium on carbon was degassed (brief evacuation under vacuum for about 30 seconds followed by venting to nitrogen the first time and then to hydrogen the subsequent two times) and then stirred 24 hr at room temperature under hydrogen (in a balloon). The mixture was diluted with 25 mL of ethyl acetate, filtered through diatomaceous earth and concentrated in vacuo. Chromatography (200 g of silica gel, 25% ethyl acetate/hexane) of the residue afforded 1.3 g (66%) of the title compound. Analysis calculated for $C_{17}H_{22}O_5$: %C, 66.65; %H, 7.24. Found: %C, 66.62; %H, 7.32.

C. (1SR,2SR-2-carboxycycloprop-1-yl) (2-(2,3-dimethoxyphenyl)ethyl) ketone: A solution of 1.3 g (4.2 mmol) of the compound from Example 52B in 9 mL of ethanol and 4.6 mL of 1N sodium hydroxide was stirred 24 hr at room temperature, then concentrated in vacuo. The residue was dissolved in 25 mL of water, extracted three times with 10 mL each of ether, then brought to pH 1 with concentrated hydrochloric acid. The resulting solution was extracted three times with 20 mL each of ethyl acetate, then the combined organics were dried ($MgSO_4$), filtered and concentrated in vacuo at 60° C. to afford 0.68 g (58%) of the title compound.

D. 5SR- and 5RS-5-(1SR,2SR-2-carboxycyclopropan-1-yl)-5-(2-(2,3-dimethoxyphenyl)ethyl)imidazolidine-2,4-dione: A solution of 0.68 g (2.5 mmol) of the compound from Example 52C in 9 mL of ethanol was added to a solution of 0.81 g (12.4 mmol) of potassium cyanide and 1.7 g (22.5 mmol) of ammonium carbonate in 9 mL of water, then this mixture was heated to 55° C. for 24 hr. The mixture was cooled and added to 150 mL of 10% aqueous sodium bisulfate. The resulting solid was filtered, washed three times with water, and dried in vacuo at 60° C. to afford 0.60 g (69%) of the title compound.

E. A solution of 0.60 g (1.7 mmol) of the compound from Example 52D and 2.7 g (8.6 mmol) of barium hydroxide in 10 mL of water was heated to 200° C. for 24 hr in a stainless steel high pressure reactor. The mixture was cooled and acidified to pH 7 with 4N sulfuric acid. The resulting solid was filtered and washed three times with 10 mL each of water. Cation exchange chromatography of the filtrate afforded a solid that was suspended in water and filtered, washed with water, acetone, and ether and dried in vacuo at 60° C. to afford 0.13 g (24%) of the title compound.

Analysis calculated for $C_{16}H_{21}NO_6$: %C, 59.43; %H, 6.55 %N, 4.33. Found: %C, 59.27; %H, 6.33; %N, 4.29.

Field Desorption Mass Spectrum: M=323.

EXAMPLE 53

Preparation of 2SR- and 2RS-2-amino-2-(1SR,2SR-2-carboxycyclopropan-1-yl)-4-(3,5-dimethoxyphenyl) butanoic acid A. (1SR,2SR-2-carbethoxycycloprop-1-yl) (2-(3,5-dimethoxyphenyl)ethenyl) ketone: A solution of 2.0 g (7.6 mmol) of the material from Preparation 4 in 5 mL dry tetrahydrofuran was added to a suspension of 0.3 g (7.6 mmol) sodium hydride in 15 mL dry tetrahydrofuran, and the mixture was stirred for 20 min at room temperature. A solution of 1.3 g (7.6 mmol) of 3,5-dimethoxybenzaldehyde in 5 mL dry tetrahydrofuran was added and the mixture stirred for 3 hr at room temperature. The mixture was added to 30 mL of water and 15 mL of ether, the organic layer was separated and the aqueous layer then extracted three times with 10 mL each of ether. The combined organics were dried (MgSO$_4$), filtered and concentrated in vacuo to afford 2.1 g (92%) of the title compound.

B. (1SR,2SR-2-carbethoxycycloprop-1-yl) (2-(3,5-dimethoxyphenyl)ethyl) ketone: A solution of 2.1 g (7.0 mmol) of the compound from Example 53A in 25 mL of ethanol and 0.4 g of 5% palladium on carbon was degassed (brief evacuation under vacuum for about 30 seconds followed by venting to nitrogen the first time and then to hydrogen the subsequent two times) and then stirred 24 hr at room temperature under hydrogen (in a balloon). The mixture was diluted with 25 mL of ethyl acetate and filtered through diatomaceous earth and concentrated in vacuo. Chromatography (200 g of silica gel, 25% ethyl acetate/hexane) of the residue afforded 1.2 g (56%) of the title compound.

Analysis calculated for $C_{17}H_{22}O_5$: %C, 66.65; %H, 7.24. Found: %C, 66.46; %H, 7.34.

C. (1SR,2SR-2-carboxycycloprop-1-yl) (2-(3,5-dimethoxyphenyl)ethyl) ketone: A solution of 1.1 g (3.6 mmol) of the compound from Example 53B in 8 mL of ethanol and 4.0 mL of 1N sodium hydroxide was stirred 24 hr at room temperature, then concentrated in vacuo. The residue was dissolved in 25 mL of water, extracted twice with 10 mL each of ether, then brought to pH 1 with concentrated hydrochloric acid. The resulting solution was extracted three times with 20 mL each of ethyl acetate, then the combined organics were dried (MgSO$_4$), filtered and concentrated in vacuo at 60° C. to afford 0.77 g (77%) of the title compound.

D. 5SR- and 5RS-5-(1SR,2SR-2-carboxycyclopropan-1-yl)-5-(2-(3,5-dimethoxyphenyl)ethyl)imidazolidine-2,4-dione: A solution of 0.77 g (2.8 mmol) of the compound from Example 53C in 9 mL of ethanol was added to a solution of 0.91 g (14.0 mmol) of potassium cyanide and 1.9 g (25.2 mmol) of ammonium carbonate in 9 mL of water, then this mixture was heated to 55° C. for 24 hr. The mixture was cooled and added to 150 mL of 10% aqueous sodium bisulfate. The resulting solid was filtered, washed three times with water, and dried in vacuo at 60° C. to afford 0.89 g (92%) of the title compound.

E. A solution of 0.89 g (2.5 mmol) of the compound from Example 53D and 4.0 g (12.5 mmol) of barium hydroxide in 10 mL of water was heated to 150° C. for 24 hr in a stainless steel high pressure reactor. The mixture was cooled and acidified to pH 7 with 0.69 mL (12.5 mmol) concentrated sulfuric acid. The resulting solution was heated for 1 hr, then filtered and washed three times with 10 mL each water. Cation exchange chromatography of the filtrate afforded a solid that was suspended in water and filtered, washed with water, acetone, and ether and dried in vacuo at 60° C. to afford 0.16 g (19%) of the title compound.

Analysis calculated for $C_{16}H_{21}NO_6$: %C, 59.43; %H, 6.55 %N, 4.33. Found: %C, 59.13; %H, 6.48; %N, 4.32.

Field Desorption Mass Spectrum: M=323.

EXAMPLE 54

Preparation of 2SR- and 2RS-2-amino-2-(1SR,2SR-2-carboxycyclopropan-1-yl)-4-(4-fluorophenyl)butanoic acid A. (1SR,2SR-2-carbethoxycycloprop-1-yl) (2-(4-fluorophenyl)ethyl) ketone: A solution of 4.3 g (17.0 mmol) of 1-iodo-2-(4-fluorophenyl)ethane and 2.1 g (32.7 mmol) of zinc/copper couple in 47 mL of benzene and 4.7 mL of N,N-dimethylacetamide was stirred for 2 hr at 60° C. The heating bath was removed and the mixture treated with 0.32 g (0.3 mmol) of tetrakis(triphenylphosphine)palladium(0). 2.5 g (14.2 mmol) of the material from Preparation 1 was added and the mixture stirred at room temperature for 1.25 hr. The mixture was diluted with 50 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried (MgSO$_4$), filtered and concentrated in vacuo. Chromatography (175 g of silica gel, 15% ethyl acetate/hexane) of the residue afforded 1.3 g (36%) of the title compound.

Analysis calculated for $C_{15}H_{17}O_3F$: %C, 68.17; %H, 6.48. Found: %C, 68.03; %H, 6.24.

Field Desorption Mass Spectrum: M=264.

B. (1SR,2SR-2-carboxycycloprop-1-yl) (2-(4-fluorophenyl)ethyl) ketone: A solution of 1.3 g (5.0 mmol) of the compound from Example 54A in 20 mL of ethanol and 5.5 mL of 1N sodium hydroxide was stirred 24 hr at room temperature, then concentrated in vacuo. The residue was dissolved in 50 mL of 1N hydrochloric acid and extracted four times with 25 mL each of ethyl acetate, then the combined organics were dried (MgSO$_4$), filtered and concentrated in vacuo to afford 1.3 g (100%) of the title compound. Analysis calculated for $C_{13}H_{13}O_3F$: %C, 66.09; %H, 5.55. Found: %C, 66.36 %H, 5.57.

Field Desorption Mass Spectrum: M=237.

C. 5SR- and 5RS-5-(1SR,2SR-2-carboxycyclopropan-1-yl)-5-(2-(4-fluorophenyl)ethyl)imidazolidine-2,4-dione: A solution of 1.4 g (4.9 mmol) of the compound from Example 54B in 6 mL of ethanol was added to a solution of 1.6 g (24.2 mmol) of potassium cyanide and 4.2 g (43.6 mmol) of ammonium carbonate in 6 mL of water, then this mixture was heated to 55° C. for 24 hr. The mixture was cooled and added to 150 mL of 1N hydrochloric acid, and the resulting precipitate was filtered, washed three times with water, then recrystallized from water and acetone to afford 1.1 g (72%) of the title compound.

Analysis calculated for $C_{15}H_{15}N_2O_4F$: %C, 58.82; %H, 4.94; %N, 9.15. Found: %C, 59.10 %H, 4.97; %N, 9.15.

Field Desorption Mass Spectrum: M=307.

D. A Solution of 1.0 g (3.3 mmol) of the compound from Example 54C and 5.1 g (16.3 mmol) of barium hydroxide in 25 mL of water was heated to 250° C. for 24 hr in a stainless steel high pressure reactor. The mixture was cooled and acidified to pH 3 with concentrated sulfuric acid, affording a solid that was filtered then suspended in 25 mL of 10% aqueous pyridine and heated to 100° C. for 1 hr. The solid was filtered, then suspended in 3N ammonium hydroxide and filtered again. Cation exchange chromatography of the combined filtrates afforded a solid that was suspended in water and filtered, washed with water, acetone and ether and dried in vacuo at 60° C. to afford 0.23 g (25%) of the title compound.

Analysis calculated for $C_{14}H_{16}NO_4F \cdot 0.25\ H_2O$: %C, 58.65; %H, 5.84; %N, 4.89. Found: %C, 58.85; %H, 5.55; %N, 4.51.

Field Desorption Mass Spectrum: M=281.

EXAMPLE 55

Preparation of 2SR- and 2RS-2-amino-2-(1SR,2SR-2-carboxycyclopropan-1-yl)-4-(2-fluorophenyl)butanoic acid A. (1SR,2SR-2-carbethoxycycloprop-1-yl) (2-(2-fluorophenyl)ethyl) ketone: A solution of 4.3 g (17.0 mmol) of 1-iodo-2-(2-fluorophenyl)ethane and 2.1 g (32.7 mmol) of zinc/copper couple in 47 mL of benzene and 4.7 mL of N,N-dimethylacetamide was stirred for 2 hr at 60° C. The heating bath was removed and the mixture treated with 0.32 g (0.28 mmol) of tetrakis(triphenylphosphine)palladium(0). 2.5 g (14.2 mmol) of the material from Preparation 1 was added and the mixture stirred at room temperature for 2 hr. The mixture was diluted with 50 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 25% ethyl acetate/hexane) of the residue afforded 1.0 g (29%) of the title compound.

Analysis calculated for $C_{15}H_{17}O_3F \cdot 0.25\ H_2O$: %C, 67.03; %H, 6.56. Found: %C, 67.33; %H, 6.40.

B. (1SR,2SR-2-carboxycycloprop-1-yl) (2-(2-fluorophenyl)ethyl) ketone: A solution of 1.0 g (4.0 mmol) of the compound from Example 55A in 15 mL of ethanol and 4.4 mL of 1N sodium hydroxide was stirred 24 hr at room temperature, then concentrated in vacuo. The residue was dissolved in 50 mL of 10% sodium bisulfate and extracted four times with 25 mL each of ethyl acetate, then the combined organics were dried ($MgSO_4$), filtered and concentrated in vacuo to afford 0.8 g (80%) of the title compound.

Analysis calculated for $C_{13}H_{13}O_3F$: %C, 66.09; %H, 5.55. Found: %C, 66.36 %H, 5.60.

Field Desorption Mass Spectrum: M=236.

C. 5SR- and 5RS-5-(1SR,2SR-2-carboxycyclopropan-1-yl)-5-(2-(2-fluorophenyl)ethyl)imidazolidine-2,4-dione: A solution of 0.8 g (3.3 mmol) of the compound from Example 55B in 5.5 mL of ethanol was added to a solution of 1.1 g (16.3 mmol) of potassium cyanide and 2.8 g (29.3 mmol) of ammonium carbonate in 5.5 mL of water, then this mixture was heated to 55° C. for 24 hr. The mixture was cooled and added to 120 mL of 10% sodium bisulfate, and the resulting precipitate was filtered, washed three times with water, then recrystallized from water and acetone and dried in vacuo at 60° C. to afford 0.6 g (60%) of the title compound.

Analysis calculated for $C_{15}H_{15}N_2O_4F$: %C, 58.82; %H, 4.94; %N, 9.15. Found: %C, 59.01%H, 4.95; %N, 9.17.

Field Desorption Mass Spectrum: M=306.

D. A solution of 0.6 g (1.96 mmol) of the compound from Example 55C and 3.1 g (9.8 mmol) of barium hydroxide in 16 mL of water was heated to 250° C. for 24 hr in a stainless steel high pressure reactor. The mixture was cooled and acidified to pH 3 with concentrated sulfuric acid, affording a solid that was filtered then rinsed two times with 10 mL of 10% aqueous pyridine. Cation exchange chromatography of the filtrate afforded a solid that was recrystallized from water/acetone. The resulting solid was dried in vacuo at 60° C. to afford 46 mg (8%) of the title compound.

Analysis calculated for $C_{14}H_{16}NO_4F \cdot 0.3\ H_2O$: %C, 58.65; %H, 5.84; %N, 4.89. Found: %C, 58.41; %H, 5.48; %N, 4.74.

Field Desorption Mass Spectrum: M=282.

EXAMPLE 56

Preparation of 2SR- and 2RS-2-amino-2-(1SR,2SR-2-carboxycyclopropan-1-yl)-4-(4-(trifluoromethyl)phenyl) butanoic acid A. (1SR,2SR-2-carbethoxycycloprop-1-yl) (2-(4-(trifluoromethyl)phenyl)ethyl) ketone: A solution of 5.1 g (17 mmol) of 1-iodo-2-(4-(trifluoromethyl)phenyl)ethane and 2.1 g (32.7 mmol) of zinc/copper couple in 47 mL of benzene and 4.7 mL of N,N-dimethylacetamide was stirred for 2 hr at 60° C. The heating bath was removed and the mixture treated with 0.32 g (0.28 mmol) of tetrakis (triphenylphosphine)palladium(0). 2.5 g (14.2 mmol) of the material from Preparation 1 was added and the mixture stirred at room temperature for 2 hr. The mixture was diluted with 50 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried ($MgSO_4$), filtered and concentrated in vacuo. Chromatography (200 g of silica gel, 20% ethyl acetate/hexane) of the residue afforded 1.8 g (39%) of the title compound.

Analysis calculated for $C_{16}H_{17}O_3F_3$: %C, 61.14; %H, 5.45. Found: %C, 61.34 %H, 5.20.

Field Desorption Mass Spectrum: M=314.

B. (1SR,2SR-2-carboxycycloprop-1-yl) (2-(4-(trifluoromethyl)phenyl)ethyl) ketone: A solution of 1.8 g (5.6 mmol) of the compound from Example 56A in 20 mL of ethanol and 6.2 mL of 1N sodium hydroxide was stirred 24 hr at room temperature, then concentrated in vacuo. The residue was dissolved in 50 mL of 10% sodium bisulfate and extracted three times with 25 mL each of ethyl acetate, then the combined organics were dried ($MgSO_4$), filtered and concentrated in vacuo to afford 1.5 g (95%) of the title compound.

Analysis calculated for $C_{14}H_{13}O_3F_3$: %C, 58.74; %H, 4.58. Found: %C, 59.00 %H, 4.63.

Field Desorption Mass Spectrum: M=286.

C. 5SR- and 5RS-5-(1SR,2SR-2-carboxycyclopropan-1-yl)-5-(2-(4-(trifluoromethyl)phenyl)ethyl)imidazolidine-2,4-dione: A solution of 1.5 g (5.3 mmol) of the compound from Example 56B in 9 mL of ethanol was added to a solution of 1.7 g (26.7 mmol) of potassium cyanide and 4.6 g (48.1 mmol) of ammonium carbonate in 9 mL of water, then this mixture was heated to 55° C. for 24 hr. The mixture was cooled and added to 150 mL of 10% sodium bisulfate, and the resulting precipitate was filtered, washed three times with water, then recrystallized from water and acetone. Drying in vacuo at 60° C. afforded 1.5 g (76%) of the title compound.

Field Desorption Mass Spectrum: M=356.

D. A solution of 1.5 g (4.1 mmol) of the compound from Example 56C and 6.4 g (20.4 mmol) of barium hydroxide in 30 mL of water was heated to 250° C. for 24 hr in a stainless steel high pressure reactor. The mixture was cooled and acidified to pH 3 with concentrated sulfuric acid, affording a solid that was filtered then rinsed two times with 10 mL of hot 10% aqueous pyridine. Cation exchange chromatography of the filtrate afforded a solid that was suspended in water, filtered and rinsed with water, acetone and ether and dried in vacuo at 60° C. to afford 0.23 g. This solid was suspended in acetone and heated at reflux for two hr, cooled and filtered. The resulting solid was refluxed in 5 mL of water for 2.5 hr, then cooled, filtered and rinsed with water, acetone and ether, and dried in vacuo at 60° C. to afford 0.11 g (8%) of the title compound.

Analysis calculated for $C_{15}H_{16}NO_4F_3 \cdot C_3H_6O$: %C, 55.53; %H, 5.70; %N, 3.60. Found: %C, 55.32; %H, 5.85; %N, 3.15.

Field Desorption Mass Spectrum: M=332.

EXAMPLE 57

Preparation of 2SR- and 2RS-2-amino-2-(1SR,2SR-2-carboxycyclopropan-1-yl)-4-(2-(trifluoromethyl)phenyl) butanoic acid A. (1SR,2SR-2-carbethoxycycloprop-1-yl) (2-(2-(trifluoromethyl)phenyl)ethyl) ketone: A solution of 5.1 g (17 mmol) of 1-iodo-2-(2-(trifluoromethyl)phenyl)ethane and 2.1 g (32.7 mmol) of zinc/copper couple in 47 mL of benzene and 4.7 mL of N,N-dimethylacetamide was stirred for 2 hr at 60° C. The heating bath was removed and the mixture treated with 0.32 g (0.28 mmol) of tetrakis (triphenylphosphine)palladium(0). 2.5 g (14.2 mmol) of the material from Preparation 1 was added and the mixture stirred at room temperature for 2 hr. The mixture was diluted with 50 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried (MgSO$_4$), filtered and concentrated in vacuo. Chromatography (150 g of silica gel, 15% ethyl acetate/hexane) of the residue afforded 1.2 g (27%) of the title compound.

Analysis calculated for $C_{16}H_{17}O_3F_3$: %C, 61.14; %H, 5.45. Found: %C, 61.38 %H, 5.44.

Field Desorption Mass Spectrum: M=314.

B. (1SR,2SR-2-carboxycycloprop-1-yl) (2-(2-(trifluoromethyl)phenyl)ethyl) ketone: A solution of 1.2 g (3.9 mmol) of the compound from Example 57A in 15 mL of ethanol and 4.2 mL of 1N sodium hydroxide was stirred 24 hr at room temperature, then concentrated in vacuo. The residue was dissolved in 50 mL of 10% sodium bisulfate and extracted three times with 25 mL each of ethyl acetate, then the combined organics were dried (MgSO$_4$), filtered and concentrated in vacuo to afford 0.9 g (83%) of the title compound.

Analysis calculated for $C_{14}H_{13}O_3F_3$: %C, 58.74; %H, 4.58. Found: %C, 58.52 %H, 4.47.

Field Desorption Mass Spectrum: M=287.

C. 5SR- and 5RS-5-(1SR,2SR-2-carboxycyclopropan-1-yl)-5-(2-(2-(trifluoromethyl)phenyl)ethyl)imidazolidine-2,4-dione: A solution of 0.9 g (3.2 mmol) of the compound from Example 57B in 5 mL of ethanol was added to a solution of 1.1 g (16.1 mmol) of potassium cyanide and 2.8 g (28.9 mmol) of ammonium carbonate in 5 mL of water, then this mixture was heated to 55° C. for 24 hr. The mixture was cooled and added to 150 mL of 10% sodium bisulfate, and the resulting precipitate was filtered, washed three times with water, then recrystallized from water and acetone. Drying in vacuo at 60° C. afforded 0.9 g (76%) of the title compound.

Field Desorption Mass Spectrum: M=357.

D. A solution of 0.8 g (2.3 mmol) of the compound from Example 57C and 3.6 g (11.4 mmol) of barium hydroxide in 17 mL of water was heated to 250° C. for 24 hr in a stainless steel high pressure reactor. The mixture was cooled and acidified to pH 3 with concentrated sulfuric acid, affording a solid that was filtered, rinsed with water, then rinsed two times with 10 mL of hot 10% aqueous pyridine. Cation exchange chromatography of the filtrate afforded a solid that was suspended in water, filtered and rinsed with water, acetone and ether, and dried in vacuo at 60° C. to afford 0.22 g (30%) of the title compound.

Analysis calculated for $C_{15}H_{16}NO_4F_3$: %C, 54.38; %H, 4.87; %N, 4.23. Found: %C, 54.11; %H, 4.77; %N, 4.14.

Field Desorption Mass Spectrum: M−2=329.

EXAMPLE 58

Preparation of 2SR- and 2RS-2-amino-2-(1SR,2SR-2-carboxycyclopropan-1-yl)-4-(2-thienyl)butanoic acid A. (1SR,2SR-2-carbethoxycycloprop-1-yl) (2-(2-thienyl)ethyl) ketone: A solution of 5.1 g (21.3 mmol) of 1-iodo-2-(2-thienyl)ethane and 2.1 g (32.7 mmol) of zinc/copper couple in 47 mL of benzene and 4.7 mL of N,N-dimethylacetamide was stirred for 2 hr at 60° C. The heating bath was removed then the mixture treated with 0.32 g (0.28 mmol) of tetrakis(triphenylphosphine)palladium(0). After 5 min, 2.5 g (14.2 mmol) of the material from Preparation 1 was added and the mixture stirred at room temperature for 1.5 hr. The mixture was diluted with 50 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried (MgSO$_4$), filtered and concentrated in vacuo. Chromatography (200 g of silica gel, 20% ethyl acetate/hexane) of the residue afforded 2.2 g (60%) of the title compound.

Analysis calculated for $C_{13}H_{16}O_3S$: %C, 61.88; %H, 6.39. Found: %C, 61.65; %H, 6.26.

Field Desorption Mass Spectrum: M=252.

B. (1SR,2SR-2-carboxycycloprop-1-yl) (2-(2-thienyl)ethyl) ketone: A solution of 2.1 g (8.1 mmol) of the compound from Example 58A in 25 mL of ethanol and 8.9 mL of 1N sodium hydroxide was stirred 24 hr at room temperature, then concentrated in vacuo. The residue was dissolved in 50 mL of 10% sodium bisulfate and extracted four times with 25 mL each of ethyl acetate, then the combined organics were dried (MgSO$_4$), filtered and concentrated in vacuo to afford 1.6 g (88%) of the title compound.

Analysis calculated for $C_{11}H_{12}O_3S$: %C, 58.91; %H, 5.39. Found: %C, 60.17; %H, 5.52.

Field Desorption Mass Spectrum: M=224.

C. 5SR- and 5RS-5-(1SR,2SR-2-carboxycyclopropan-1-yl)-5-(2-(2-thienyl)ethyl)imidazolidine-2,4-dione: A solution of 1.6 g (7.1 mmol) of the compound from Example 58B in 7.5 mL of ethanol was added to a solution of 2.3 g (35.7 mmol) of potassium cyanide and 6.2 g (64.2 mmol) of ammonium carbonate in 7.5 mL of water, then this mixture was heated to 55° C. for 24 hr. The mixture was cooled and added to 150 mL of 10% sodium bisulfate, and the resulting precipitate was filtered, washed three times with water, then recrystallized from water and acetone. Drying in vacuo at 60° C. afforded 1.5 g (72%) of the title compound.

Analysis calculated for $C_{13}H_{14}O_4S$: %C, 53.05; %H, 4.79; %N, 9.52. Found: %C, 53.30; %H, 4.75; %N, 9.37.

Field Desorption Mass Spectrum: M=294.

D. A solution of 1.5 g (4.9 mmol) of the compound from Example 58C and 7.8 g (24.7 mmol) of barium hydroxide in 37 mL of water was heated to 250° C. for 24 hr in a stainless steel high pressure reactor. The mixture was cooled and acidified to pH 2 with concentrated sulfuric acid, affording a solid that was filtered and rinsed with water. The solid was suspended in 20 mL of hot 10% aqueous pyridine then filtered and rinsed with 10 mL of hot 10% aqueous pyridine. The filtrates were combined and concentrated in vacuo to remove most of the pyridine. Cation exchange chromatography afforded a solid that was suspended in water, filtered and washed with water, acetone and ether, and dried in vacuo at 0° C. to afford 0.52 g (39%) of the title compound.

Analysis calculated for $C_{12}H_{15}NO_4S$: %C, 53.52; %H, 5.61; %N, 5.20. Found: %C, 53.23; %H, 5.49; %N, 5.05.

Field Desorption Mass Spectrum: M−1=268.

EXAMPLE 59

Preparation of 2SR- and 2RS-2-amino-2-(1SR,2SR-2-carboxycyclopropan-1-yl)-4-(3-thienyl) butanoic acid A. (1SR,2SR-2-carbethoxycycloprop-1-yl) (2-(3-thienyl ethyl) ketone: A solution of 7.7 g (32.5 mmol) of 1-iodo-2-(3-thienyl)ethane and 4.1 g (62.3 mmol) of zinc/copper couple in 85 mL of benzene and 8.5 mL of N,N-dimethylacetamide was stirred for 2 hr at 60° C. The heating bath was removed then the mixture treated with 0.62 g (0.54 mmol) of tetrakis(triphenylphosphine)palladium(0). After 5 min, 4.8 g (27.1 mmol) of the material from Preparation 1 was added and the mixture stirred at room temperature for 2 hr. The mixture was diluted with 85 mL of ethyl acetate and filtered through diatomaceous earth. The filtrate was washed with 75 mL of 1N hydrochloric acid, 75 mL of saturated aqueous sodium bicarbonate and 75 mL of saturated aqueous sodium chloride. The organic layer was dried (MgSO$_4$), filtered and concentrated in vacuo. Chromatography (250 g of silica gel, 15% ethyl acetate/hexane) of the residue afforded 2.4 g (35%) of the title compound.

Analysis calculated for $C_{13}H_{16}O_3S$: %C, 61.88; %H, 6.39. Found: %C, 62.08; %H, 6.39.

Field Desorption Mass Spectrum: M=252.

B. (1SR,2SR-2-carboxycycloprop-1-yl) (2-(3-thienyl) ethyl) ketone: A solution of 2.3 g (9.2 mmol) of the compound from Example 59A in 30 mL of ethanol and 10.2 mL of 1N sodium hydroxide was stirred 24 hr at room temperature, then concentrated in vacuo. The residue was dissolved in 50 mL of 10% sodium bisulfate and extracted four times with 25 mL each of ethyl acetate, then the combined organics were dried (MgSO$_4$), filtered and concentrated in vacuo to afford 1.9 g (92%) of the title compound.

Analysis calculated for $C_{11}H_{12}O_3S$: %C, 58.91; %H, 5.39. Found: %C, 58.65; %H, 5.35.

Field Desorption Mass Spectrum: M=224.

C. 5SR- and 5RS-5-(1SR,2SR-2-carboxycyclopropan-1-yl)-5-(2-(3-thienyl)ethyl)imidazolidine-2,4-dione: A solution of 1.9 g (8.4 mmol) of the compound from Example 59B in 10 mL of ethanol was added to a solution of 2.7 g (42.1 mmol) of potassium cyanide and 7.3 g (75.9 mmol) of ammonium carbonate in 10 mL of water, then this mixture was heated to 55° C. for 4 hr. The mixture was cooled and added to 150 mL of 10% sodium bisulfate, and the resulting precipitate was filtered, washed three times with water, then recrystallized from water and acetone. Drying in vacuo at 60° C. afforded 1.9 g (78%) of the title compound.

Analysis calculated for $C_{13}H_{14}O_4S$: %C, 53.05; %H, 4.79; %N, 9.52. Found: %C, 53.29; %H, 5.03; %N, 9.37.

Field Desorption Mass Spectrum: M=294.

D. A solution of 1.9 g (6.6 mmol) of the compound from Example 59C and 10.4 g (33.0 mmol) of barium hydroxide in 50 mL of water was heated to 250° C. for 24 hr in a stainless steel high pressure reactor. The mixture was cooled and acidified to pH 2 with concentrated sulfuric acid, affording a solid that was filtered and washed once with water and twice with hot 10% aqueous pyridine. Cation exchange chromatography of the filtrate afforded a solid that was suspended in water, filtered, washed with water, acetone and ether and dried in vacuo at 60° C. to afford 0.9 g (51%) of the title compound.

Analysis calculated for $C_{12}H_{15}NO_4S$: %C, 53.52; %H, 5.61; %N, 5.20. Found: %C, 53.46; %H, 5.57; %N, 5.13.

Field Desorption Mass Spectrum: M=269.

EXAMPLE 60

Preparation of 2SR- and 2RS-2-amino-2-(1SR,2SR-2-carboxycyclopropan-1-yl)-4-(3-phenoxyphenyl) butanoic acid A. (1SR,2SR-2-carbethoxycycloprop-1-yl) (2-(3-phenoxyphenyl)ethenyl) ketone: A solution of 2.5 g (9.5 mmol) of the material from Preparation 4 in 5 mL of tetrahydrofuran was added to a suspension of 0.4 g (9.9 mmol) of sodium hydride in 5 mL of tetrahydrofuran, and the mixture was stirred for 30 min at room temperature. 3-phenoxybenzaldehyde was added and the mixture stirred for 20 min at room temperature. The mixture was diluted with 15 mL of water and extracted three times with 10 mL each of ether. The combined organics were dried (MgSO$_4$), filtered and concentrated in vacuo to afford 3.47 g (100%) of the title compound.

B. (1SR,2SR-2-carbethoxycycloprop-1-yl) (2-(3-phenoxyphenyl)ethyl) ketone: A solution of 3.47 g (9.46 mmol) of the compound from Example 60A in 50 mL of ethanol and 0.13 g of 5% palladium on carbon was degassed (brief evacuation under vacuum for about 30 seconds followed by venting to nitrogen the first time and then to hydrogen the subsequent two times) and then stirred 24 hr at room temperature under hydrogen (in a balloon). The mixture was diluted with 50 mL of ethyl acetate, filtered through diatomaceous earth and concentrated in vacuo. Chromatography (175 g of silica gel, 20% ethyl acetate/hexane) of the residue afforded 2.5 g (79%) of the title compound.

Analysis calculated for $C_{21}H_{22}O_4$: %C, 74.54; %H, 6.55. Found: %C, 74.50; %H, 6.68.

Field Desorption Mass Spectrum: M=338.

C. (1SR,2SR-2-carboxycycloprop-1-yl) (2-(3-phenoxyphenyl)ethyl) ketone: A solution of 2.5 g (7.4 mmol) of the compound from Example 60B in 26 mL of ethanol and 8.2 mL of 1N sodium hydroxide was stirred 24 hr at room temperature, then concentrated in vacuo. The residue was dissolved in 50 mL of 10% aqueous sodium bisulfate and extracted four times with 25 mL each of ethyl acetate. The combined organics were dried (MgSO$_4$), filtered and concentrated in vacuo at 50° C. to afford 2.2 g (93%) of the title compound.

D. 5SR- and 5RS-5-(1SR,2SR-2-carboxycyclopropan-1-yl)-5-(2-(3-phenoxyphenyl)ethyl)imidazolidine-2,4-dione: A solution of 2.2 g (6.9 mmol) of the compound from Example 60C in 12.5 mL of ethanol was added to a solution of 2.3 g (34.7 mmol) of potassium cyanide and 6.0 g (62.4 mmol) of ammonium carbonate in 12.5 mL of water, then this mixture was heated to 55° C. for 24 hr. The mixture was cooled and added to 200 mL of 10% aqueous sodium bisulfate. The resulting solid was filtered, washed three times with water, and dried in vacuo at 60° C. to afford 2.3 g (88%) of the title compound. Analysis calculated for $C_{21}H_2O\ N_2O_5$: %C, 66.31; %H, 5.30; %N, 7.36. Found: %C, 66.52; %H, 5.36; %N, 7.28.

Field Desorption Mass Spectrum: M=380.

E. A solution of 2.3 g (6.0 mmol) of the compound from Example 60D and 9.4 g (29.9 mmol) of barium hydroxide in 40 mL of water was heated to 200° C. for 24 hr in a stainless steel high pressure reactor. The mixture was cooled and acidified to pH 2 with 4N sulfuric acid. The mixture was then filtered through diatomaceous earth and washed twice with 0.25N sodium hydroxide and once with water. Cation exchange chromatography of the filtrate afforded a solid that was suspended in water and filtered, washed with water, acetone, and ether and dried in vacuo at 60° C. to afford 0.74 g (35%) of the title compound.

Analysis calculated for $C_{20}H_{21}NO_5 \cdot 0.25\ H_2O$: %C, 66.75; %H, 6.02; %N, 3.89. Found: %C, 66.76; %H, 6.05; %N, 3.70.

Field Desorption Mass Spectrum: M=355.

EXAMPLE 61

Preparation of 2SR- and 2RS-2-amino-2-(1SR,2SR-2-carboxycyclopropan-1-yl)-4-(1-methylindol -3-yl) butanoic acid A. (1SR,2SR-2-carbethoxycycloprop-1-yl) (2-(1-methylindol-3-yl)ethenyl) ketone: A solution of 2.0 g (7.6 mmol) of the material from Preparation 4 in 10 mL of tetrahydrofuran was added to a suspension of 0.3 g (7.6 mmol) sodium hydride in 15 mL of tetrahydrofuran, and the mixture was stirred for 20 min at room temperature. A solution of 1.3 g (7.6 mmol) of 1-methylindole-3-carboxaldehyde in 10 mL of tetrahydrofuran was added and the mixture stirred for 16 hr at reflux. The mixture was cooled to room temperature, diluted with 30 mL of water and extracted three times with 15 mL each of ether. The combined organics were dried (MgSO$_4$), filtered and concentrated in vacuo to afford 2.2 g (96%) of the title compound.

B. (1SR,2SR-2-carbethoxycycloprop-1-yl) (2-(1-methylindol-3-yl)ethyl) ketone: A solution of 2.2 g (7.2 mmol) of the compound from Example 61A in 50 mL of ethanol and 0.1 g of 5% palladium on carbon was degassed (brief evacuation under vacuum for about 30 seconds followed by venting to nitrogen the first time and then to hydrogen the subsequent two times) and then stirred 3.5 hr at room temperature under hydrogen (in a balloon). The mixture was filtered through diatomaceous earth and concentrated in vacuo. Chromatography (100 g of silica gel, 20% ethyl acetate/hexane) of the residue afforded 1.4 g (63%) of the title compound.

Analysis calculated for $C_{18}H_{21}NO_3$: %C, 72.22; %H, 7.07; %N, 4.68. Found: %C, 72.16; %H, 7.06; %N, 4.64.

Field Desorption Mass Spectrum: M=299.

C. (1SR,2SR-2-carboxycycloprop-1-yl) (2-(1-methylindol-3-yl)ethyl) ketone: A solution of 1.3 g (4.3 mmol) of the compound from Example 61B in 15 mL of ethanol and 4.7 mL of 1N sodium hydroxide was stirred 24 hr at room temperature, then concentrated in vacuo. The residue was dissolved in 25 mL of 10% aqueous sodium bisulfate and extracted three times with 20 mL each of ethyl acetate, then the combined organics were dried (MgSO$_4$), filtered and concentrated in vacuo to afford 1.2 g (100%) of the title compound.

Analysis calculated for $C_{16}H_{17}NO_3$: %C, 70.83; %H, 6.32; %N, 5.16. Found: %C, 70.85; %H, 6.28; %N, 4.96.

Field Desorption Mass Spectrum: M=271.

D. 5SR- and 5RS-5-(1SR,2SR-2-carboxycyclopropan-1-yl)-5-(2-(1-methylindol-3-yl)ethyl)imidazolidine-2,4-dione: A solution of 1.2 g (4.3 mmol) of the compound from Example 61C in 8 mL of ethanol was added to a solution of 1.4 g (21.6 mmol) of potassium cyanide and 3.7 g (38.8 mmol) of ammonium carbonate in 8 mL of water, then this mixture was heated to 55° C. for 24 hr. The mixture was cooled and added to 125 mL of 10% aqueous sodium bisulfate. The resulting solid was filtered, washed three times with water, and dried in vacuo at 60° C. to afford 1.1 g (77%) of the title compound.

Analysis calculated for $C_{18}H_{19}N_3O_4 \cdot 0.5\ H_2O$: %C, 61.71; %H, 5.75; %N, 11.99. Found: %C, 61.97; %H, 5.72; %N, 12.03.

Field Desorption Mass Spectrum: M=341.

E. A solution of 1.1 g (3.3 mmol) of the compound from Example 61D and 5.2 g (16.6 mmol) of barium hydroxide in 27 mL of water was heated to 250° C. for 24 hr in a stainless steel high pressure reactor. The mixture was cooled and acidified to pH 3 with concentrated sulfuric acid. The resulting solution was filtered and the solid suspended in 20 mL of refluxing 10% aqueous pyridine for 10 min, then filtered. Cation exchange chromatography of the combined filtrates afforded a solid that was dissolved in water and concentrated in vacuo twice. The solid was recrystallized from water/acetone, filtered, washed with water, acetone and ether, and dried in vacuo at 60° C. to afford 0.11 g (11%) of the title compound.

Analysis calculated for $C_{17}H_{20}N_2O_4 \cdot H_2O$: %C, 61.07; %H, 6.63 N, 8.38. Found: %C, 61.33; %H, 6.39; %N, 8.06.

Field Desorption Mass Spectrum: M=316.

EXAMPLE 62

Preparation of 2SR- and 2RS-2-amino-2-(1SR,2SR-2-carboxycyclopropan-1-yl)-3-cyclohexylpropanoic acid A. (1SR,2SR-2-carbethoxycycloprop-1-yl) ((cyclohexyl)methyl) ketone: A solution of 5.4 g (24.2 mmol) of (cyclohexyl)methyl iodide and 3.3 g (50.6 mmol) of zinc/copper couple in 66 mL of benzene and 8 mL of N,N-dimethylacetamide was stirred for 3 hr at 50° C., then treated with 0.5 g (0.44 mmol) of tetrakis(triphenylphosphine) palladium(0) and heated for 5 min more. The heating bath was removed, 3.8 g (22 mmol) of the material from Preparation 1 was added and the mixture stirred at room temperature for 1 hr. The mixture was diluted with 66 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 10% ethyl acetate/hexane) of the residue afforded 1.5 g (43%) of the title compound.

Analysis calculated for $C_{12}H_{18}O_3$: %C, 70.56; %H, 9.30. Found: %C, 70.14; %H, 8.94.

B. (1SR,2SR-2-carboxycycloprop-1-yl) ((cyclohexyl)methyl) ketone: A solution of 3.3 g (15.7 mmol) of the compound from Example 62A in 14 mL of ethanol and 7.0 mL of 1N sodium hydroxide was stirred 24 hr at 75° C., then concentrated in vacuo. The residue was dissolved in 20 mL of water and extracted twice with 20 mL each of ether. The aqueous layer was acidified to pH 1 and extracted three times with 20 mL each of ether. The combined organics were dried (MgSO$_4$), filtered and concentrated in vacuo to afford 0.7 g (56%) of the title compound.

C. 5SR- and 5RS-5-(1SR,2SR-2-carboxycyclopropan-1-yl)-5-((cyclohexyl)methyl)imidazolidine-2,4-dione: A solution of 0.7 g (3.5 mmol) of the compound from Example 62B in 10 mL of ethanol was added to a solution of 1.1 g (17.6 mmol) of potassium cyanide and 2.5 g (31.7 mmol) of ammonium carbonate in 10 mL of water, then this mixture was stirred for 24 hr at 50° C. At this time, an additional 1.1 g (17.6 mmol) of potassium cyanide and 2.5 g (31.7 mmol) of ammonium carbonate were added and the mixture was stirred for 24 hr at 60° C. The mixture was cooled, added to 150 mL of 10% aqueous sodium bisulfate, the resulting solid was filtered and washed three times with water, then dried in vacuo overnight at 60° C. to afford 0.7 g (74%) of the title compound.

D. A solution of 0.7 g (2.6 mmol) of the compound from Example 62C in 25 mL of 5N sodium hydroxide was heated to 250° C. for 24 hr in a stainless steel high pressure reactor. The mixture was cooled and acidified to pH 7 with concentrated hydrochloric acid. Cation exchange chromatography of this solution gave a solid that was suspended in water, filtered, washed with water, acetone and ether and dried in vacuo at 60° C. to afford 0.44 g (66%) of the title compound.

Analysis calculated for $C_{13}H_{21}NO_4 \cdot 0.25\ H_2O$: %C, 60.10; %H, 8.34; %N, 5.39. Found: %C, 59.72; %H, 7.26; %N, 5.36.

Field Desorption Mass Spectrum: M+1=256.

EXAMPLE 63

Preparation of 2R 2-amino-2-(1S,2S-2-carboxycyclopropan-1-yl)-4,4-diphenylbutanoic acid A. (1S,2S-2-(1R,2S,5R-Carbomenthyloxy)cycloprop-1-yl) (2,2-(diphenyl)ethyl) ketone: A solution of 5.5 g (18 mmol) of 2,2-diphenyl-1-iodoethane and 2.8 g (42.9 mmol) of zinc/copper couple in 60 mL of benzene and 8 mL of dimethylacetamide was stirred for 3 hr at 60° C., then treated with 0.8 g (0.7 mmol) of tetrakis(triphenylphosphine)palladium(0) and heated for 5 min more. The heating bath was removed, 4.7 g (16.4 mmol) of the material from Preparation 5 was added and the mixture stirred at room temperature for 1 hr. The mixture was diluted with 60 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried ($MgSO_4$), filtered and concentrated in vacuo. Chromatography (200 g of silica gel, 10% ethyl acetate/hexane) of the residue afforded 5.2 g (73%) of the title compound.

Analysis calculated for $C_{29}H_{36}O_3$: %C, 80.52; %H, 8.39. Found: %C, 80.31; %H, 8.26.

Field Desorption Mass Spectrum: M=432. $[\alpha]_D^{20}=+28.4°$ (c=1, MeOH).

B. (1S,2S-2-carboxycycloprop-1-yl) (2,2-(diphenyl)ethyl) ketone: A solution of 5.1 g (11.8 mmol) of the compound from Example 63A in 26 mL of ethanol and 13 mL of in sodium hydroxide was stirred overnight at 55° C., then concentrated in vacuo. The residue was dissolved in 50 mL of water, extracted three times with 20 mL each of ether, then the aqueous layer was brought to pH 1 with concentrated hydrochloric acid. The resulting solution was extracted three times with 20 mL each of ether, then the combined organics were dried ($MgSO_4$), filtered and concentrated in vacuo to afford 2.52 g (72%) of the title compound.

C. 5SR-5-(1S,2S-2-carboxycyclopropan-1-yl)-5-(2,2-(diphenyl)ethyl)imidazolidine-2,4-dione: A solution of 2.5 g (8.5 mmol) of the compound from Example 63B in 14 mL of ethanol was added to a solution of 2.8 g (42.8 mmol) of potassium cyanide and 6.0 g (77.0 mmol) of ammonium carbonate in 14 mL of water, then this mixture was heated to 55° C. for 24 hr. The mixture was cooled and added to 200 mL of 10% aqueous sodium bisulfate. The resulting mixture was allowed to stand overnight at room temperature, then the solid was filtered, and recrystallization from acetone and water afforded 2.2 g (71%) of the title compound.

Analysis calculated for $C_{21}H_{20}N_2O_4 \cdot 0.25\ H_2O$: %C, 68.37; %H, 5.60, %N, 7.59. Found: %C, 68.42; %H, 5.48, %N, 7.15.

D. 5R-(1S,2S-2-(carbo(4-methoxy)benzyloxy)cyclopropan-1-yl)-5-(2,2-(diphenyl)ethyl)-3-(4-methoxybenzyl)imidazolidine-2,4-dione and 5S-(1S,2S-2-(carbo(4-methoxy)benzyloxy)cyclopropan-1-yl)-5-(2,2-(diphenyl)ethyl)-3-(4-methoxybenzyl)imidazolidine-2,4-dione: A solution of 2.1 g (5.9 mmol) of the compound from Example 63C and 1.6 g (16.5 mmol) of potassium bicarbonate in 20 mL of N,N-dimethylformamide was treated with 2.1 g (13.6 mmol) of 4-methoxybenzyl chloride and heated to 100° C. for 18 hr. The mixture was diluted with 40 mL of ether and 40 mL of water. The organic layer was separated and the aqueous layer was extracted three times with 20 mL each of ether, then the combined organics were dried ($MgSO_4$), filtered and concentrated in vacuo. Chromatography (250 g of silica gel, 30% ethyl acetate/hexane) of the residue afforded 1.2 g (32%) of the 5R-isomer of title compound (higher $R_f$ material) and 1.2 g (35%) of the 5S-isomer of the title compound (lower $R_f$ material).

5R-isomer: Analysis calculated for $C_{37}H_{36}N_2O_6$: %C, 73.49; H, 6.00; %N, 4.63. Found: %C, 73.76; %H, 6.13; %N, 4.57.

Field Desorption Mass Spectrum: M=604.

$[\alpha]_D^{20}=+51.0°$ (c=1, $CH_2Cl_2$).

5S-isomer: Analysis calculated for $C_{37}H_{36}N_2O_6 \cdot C_6H_{14}$: %C, 74.76; %H, 7.29; %N, 4.05. Found: %C, 74.73; %H, 7.00; %N, 4.46.

Field Desorption Mass Spectrum: M=604.

$[\alpha]_D^{20}=+63.2°$ (c=1, $CH_2Cl_2$).

E. 5R-5-(1S,2S-2-carboxycyclopropan-1-yl)-5-(2,2-(diphenyl)ethyl)imidazolidine-2,4-dione: A solution of 1.0 g (1.6 mmol) of the 5R-isomer from Example 63D in 50 mL of acetonitrile was added to a solution of 7.2 g (13.2 mmol) of ceric ammonium nitrate in 15 mL of water, then this mixture was stirred at room temperature for 5 hr. The mixture was diluted with 50 mL of brine. The organic layer was separated and the aqueous layer was extracted four times with 50 mL each of ethyl acetate, then the combined organics were dried ($MgSO_4$), filtered and concentrated in vacuo. Chromatography (150 g of silica gel, 2% glacial acetic acid/50% ethyl acetate/48%hexane) of the residue afforded 0.37 g (63%) of the title compound.

F. A solution of 0.37 g (1.0 mmol) of the compound from Example 63E and 1.6 g (5 mmol) of barium hydroxide in 10 mL of water was heated to 200° C. for 24 hr in a stainless steel high pressure reactor. The mixture was cooled and acidified to pH 7 with 0.27 mL (5 mmol) of concentrated sulfuric acid. The resulting solid was filtered and washed three times with 10 mL each of water. Cation exchange chromatography of the filtrate afforded a solid that was suspended in water and filtered, washed with water, acetone and ether and dried in vacuo at 60° C. to afford 0.028 g (8%) of the title compound.

Analysis calculated for $C_{20}H_{21}NO_4 \cdot 0.25\ H_2O$: %C, 69.99; %H, 6.30; %N, 4.38. Found: %C, 69.59; %H, 6.15; %N, 4.72.

Field Desorption Mass Spectrum: M=339.

$[\alpha]_D^{20}=+44.0°$ (c=0.5, 1N NaOH).

G. Alternative preparation of 5SR-5-(1S,2S-2-carboxycyclopropan-1-yl)-5-(2,2-(diphenyl)ethyl)imidazolidine-2,4-dione: A solution of 9.4 g (21.7 mmol) of the compound from Example 63A in 50 mL of ethanol and 24 mL of 1N sodium hydroxide was stirred overnight at 55° C. 7.7 g (119.0 mmol) of potassium cyanide, 19.5 g (195.0 mmol) of ammonium carbonate and 24 mL of water were added, then this mixture was heated to 55° C. for 120 hr. The mixture was cooled, extracted once with 30 mL of ether then added to 300 mL of 10% aqueous sodium bisulfate. The resulting mixture was allowed to stand at room temperature, then the solid was filtered, and recrystallization from acetone and water afforded 4.0 g (50%) of the title compound.

H. Alternative preparation or 5R-(1S,2S-2-(carbo(4-methoxy)benzyloxy)cyclopropan-1-yl)-5-(2,2-(diphenyl)ethyl)-(4-methoxybenzyl)imidazolidine-2,4-dione and 5S-(1S,2S-2-(carbo(4-methoxy)benzyloxy)cyclopropan-1-yl)-5-(2,2-(diphenyl)ethyl)-3-(4-methoxybenzyl)imidazolidine-2,4-dione: A solution of 4.0 g (11.0 mmol) of the compound from Example 63G and 3.1 g (30.7 mmol) of potassium bicarbonate in 40 mL of N,N-dimethylformamide was treated with 3.9 g (25.2 mmol) of 4-methoxybenzyl chloride and heated to 130° C. for 3 hr. The mixture was diluted with 40 mL of ether and 80 mL of water. The organic layer was separated and the aqueous layer was extracted three times with 30 mL each of ether, then the combined organics were dried (MgSO$_4$), filtered and concentrated in vacuo. Chromatography (700 g of silica gel, 30% ethyl acetate/hexane) of the residue afforded 2.0 g (30%) of the 5R-isomer of title compound (higher R$_f$ material) and 2.7 g (41%) of the 5S-isomer of the title compound (lower R$_f$ material).

5R-isomer: Analysis calculated for C$_{37}$H$_{36}$N$_2$O$_6$: %C, 73.49; %H, 6.00; %N, 4.63. Found: %C, 73.19; %H, 5.98; %N, 4.51.

Field Desorption Mass Spectrum: M+1=605.

[α]$_D$$^{20}$=+47.8° (c=1, CH$_2$Cl$_2$).

5S-isomer: Analysis calculated for C$_{37}$H$_{36}$N$_2$O$_6$: %C, 73.49; %H, 6.00; %N, 4.63. Found: %C, 73.63; %H, 6.24; %N, 4.51.

Field Desorption Mass Spectrum: M=604.

[α]$_D$$^{20}$=+63.8° (c=1, CH$_2$Cl$_2$).

EXAMPLE 64

Preparation of 2S-2-amino-2-(1S,2S-2-carboxycyclopropan-1-yl)-4,4-diphenylbutanoic acid A. 5S-5-(1S,2S-2-carboxycyclopropan-1-yl)-5-(2,2-(diphenyl)ethyl)imidazolidine-2,4-dione: A solution of 1.13 g (1.9 mmol) of the 5S-isomer from Example 63D in 50 mL of acetonitrile was added to a solution of 8.2 g (15.0 mmol) of ceric ammonium nitrate in 15 mL of water, then this mixture was stirred at room temperature for 3 hr. The mixture was diluted with 50 mL of brine. The organic layer was separated and the aqueous layer was extracted four times with 50 mL each of ethyl acetate, then the combined organics were dried (MgSO$_4$), filtered and concentrated in vacuo. Chromatography (150 g of silica gel, 2% glacial acetic acid/50% ethyl acetate/48%hexane) of the residue afforded 0.24 g (35%) of the title compound.

B. A solution of 0.24 g (0.7 mmol) of the compound from Example 64A and 1.1 g (3.5 mmol) of barium hydroxide in 10 mL of water was heated to 200° C. for 24 hr in a stainless steel high pressure reactor. The mixture was cooled and acidified to pH 7 with 0.27 mL (5 mmol) of concentrated sulfuric acid. The resulting solid was filtered and washed three times with 10 mL each of water. Cation exchange chromatography of the filtrate afforded a solid that was suspended in water and filtered, washed with water, acetone and ether and dried in vacuo at 60° C. to afford 0.014 g (6%) of the title compound.

Analysis calculated for C$_{20}$H$_{21}$NO$_4$.H$_2$O.0.25 C$_5$H$_5$N: %C, 67.67; %H, 6.48; %N, 4.64. Found: %C, 67.72; %H, 6.11; %N, 4.95.

Field Desorption Mass Spectrum: M=339.

[α]$_D$$^{20}$=+46.0° (c=0.5, 1N NaOH).

C. Alternative preparation of 2S-2-amino-2-(1S,2S-2-carboxycyclopropane-1-yl)-4,4-diphenylbutanoic acid. A solution of 2.7 g (4.5 mmol) of the compound from Example 63H in 100 mL of 1N sodium hydroxide was heated to 200° C. for 24 hr in a stainless steel high pressure reactor. The mixture was cooled, washed three times with 30 mL each of ether, then acidified to pH 7 with concentrated hydrochloric acid. This solution was concentrated to half its volume, then cation exchange chromatography afforded a solid that was suspended in water and filtered, washed with water, acetone and ether and dried in vacuo at 60° C. to afford 0.91 g (59%) of the title compound.

Analysis calculated for C$_{20}$H$_{21}$NO$_4$.0.25 H$_2$O: %C, 69.85; %H, 6.30; %N, 4.07. Found: %C, 69.50; %H, 6.71; %N, 4.07.

Field Desorption Mass Spectrum: M=339.

[α]$_D$$^{20}$=+42.8° (c=0.5, 1N NaOH).

EXAMPLE 65

Preparation of 2R 2-amino-2-(1R,2R-2-carboxycyclopropan-1-yl)-4,4-diphenylbutanoic acid A. (1R,2R-2-(1S,2R,5S-Carbomenthyloxy)cycloprop-1-yl) (2,2-(diphenyl)ethyl) ketone: A solution of 7.1 g (23.0 mmol) of 2,2-diphenyl-1-iodoethane and 2.9 g (44.2 mmol) of zinc/copper couple in 65 mL of benzene and 6.5 mL of N,N-dimethylacetamide was stirred for 2.5 hr at 60° C., then treated with 0.44 g (0.38 mmol) of tetrakis (triphenylphosphine)palladium(0). The heating bath was removed, 5.5 g (19.2 mmol) of the material from Preparation 6 was added and the mixture stirred at room temperature for 1 hr. The mixture was diluted with 65 mL of ethyl acetate and filtered through diatomaceous earth. The filtrate was washed with 60 mL of 10% aqueous sodium bisulfate, 60 mL of saturated aqueous sodium bicarbonate and 60 mL of saturated aqueous sodium chloride. The organic layer was dried (MgSO$_4$), filtered and concentrated in vacuo. Chromatography (400 g of silica gel, 10% ethyl acetate/hexane) of the residue afforded 4.5 g (54%) of the title compound.

Analysis calculated for C$_{29}$H$_{36}$O$_3$: %C, 80.52; %H, 8.39. Found: %C, 80.81; %H, 8.38.

Field Desorption Mass Spectrum: M=432.

[α]$_D$$^{20}$=−95.5° (c=1, CH$_2$Cl$_2$).

B. 5R-(1R,2R-2-(1S,2R,5S-Carbomenthyloxy)cycloprop-1-yl)-5-(2,2-(diphenyl)ethyl)imidazolidine-2,4-dione: A solution of 6.3 g (14.5 mmol) of the compound from Example 65A in 35 mL of ethanol was added to a solution of 4.7 g (72.3 mmol) of potassium cyanide and 12.5 g (130.1 mmol) of ammonium carbonate in 20 mL of water, then this mixture was heated to 55° C. for 24 hr. The mixture was cooled and 25 mL of water was added. The mixture was extracted four times with 30 mL each of ethyl acetate, then the combined organics were dried (MgSO$_4$), filtered and concentrated in vacuo. Recrystallization from ethyl acetate afforded 0.54 g (7%) of the title compound. The mother liquors were concentrated in vacuo to afford 1.2 g (16%) of a mixture of two diastereomers, 5R-(1R,2R-2-(1S,2R,5S-carbomenthyloxy)cycloprop-1-yl)-5-(2,2-(diphenyl)ethyl)imidazolidine-2,4-dione and 5S-(1R,2R-2-(1S,2R,5S-carbomenthyloxy)cycloprop-1-yl)-5-(2,2-(diphenyl)ethyl) imidazolidine-2,4-dione. Analysis calculated for C$_{31}$H$_{38}$N$_2$O$_4$: %C, 74.07; %H, 7.62, %N, 5.57. Found: %C, 74.21; %H, 7.64, %N, 5.65.

Field Desorption Mass Spectrum: M=502.

[α]$_D$$^{20}$=+3.6° (c=1, CH$_2$Cl$_2$).

C. 5R-(1R,2R-2-(1S,2R,5S-Carbomenthyloxy) cycloprop-1-yl)-3-benzenesulfonyl-5-(2,2-(diphenyl)ethyl) imidazolidine-2,4-dione: A solution of 0.51 g (1.0 mmol) of the compound from Example 65B in 12 mL THF was treated with 1.1 mL (1.1 mmol) of a 1M THF solution of sodium bis(trimethylsilyl)amide. The mixture was stirred at room temperature for 30 min. 0.19 g (1.1 mmol) of benzenesulfonyl chloride was added and the mixture was heated to reflux for 16 hr. The mixture was cooled, diluted with 15 mL of water then extracted three times with ether. The combined organics were dried (MgSO$_4$), filtered and concentrated in vacuo. Chromatography (75 g of silica gel, 30% ethyl acetate/hexane) of the residue afforded 0.41 g (63% of the title compound.

D. A solution of 0.41 g (0.64 mmol) of the compound from Example 65C in 25 mL of 1N aqueous sodium hydroxide was heated to reflux for 18 hr. The mixture was cooled and extracted twice with 20 mL each of ether. The aqueous portion was acidified to pH 2 with 5N hydrochloric acid and the resulting precipitate was filtered, washed two times with 5 mL each of water, then with acetone whereupon the solid dissolved. Cation exchange chromatography of the filtrate afforded a solid which was dissolved in acetone and concentrated in vacuo. The solid was suspended in ether, filtered and dried in vacuo at 60° C. to afford 7 mg (3%) of the title compound. The forerun from the cation exchange column was concentrated in vacuo and heated to reflux for 18 hr in 6N aqueous hydrochloric acid. The mixture was cooled and concentrated in vacuo. Water was added and the mixture was concentrated in vacuo again. The resulting solid was suspended in 10 mL of water, filtered and rinsed once with water, twice with acetone and twice with ether then dried in vacuo at 60° C. to afford another 24 mg (10%) of the title compound.

Analysis calculated for $C_{20}H_{21}NO_4 \cdot 1.5$ NaCl: %C, 56.25; %H, 4.96; %N, 3.28. Found: %C, 56.24; %H, 4.94; %N, 3.25.

Field Desorption Mass Spectrum: M=339.

$[\alpha]_D^{20}$=−40.0° (c=0.25, in NaOH).

EXAMPLE 66

Preparation of 2S-2-amino-2-(1R,2R-2-carboxycyclopropan-1-yl)-4,4-diphenylbutanoic acid A. 5S-(1R,2R-2-(1S,2R,5S-Carbomenthyloxy)cycloprop-1-yl)-3-benzenesulfonyl-5-(2,2-(diphenyl)ethyl) imidazolidine-2,4-dione: A solution of 1.1 g (2.1 mmol) of the mixture of 5R- and 5S-(1R,2R-2(1S,2R,5S-carbomenthyloxy)cycloprop-1-yl)-5-(2,2-(diphenyl)ethyl) imidazolidine-2,4-dione from Example 65B in 15 mL of THF was treated with 2.3 mL (2.3 mmol) of a 1M THF solution of sodium bis(trimethylsilyl)amide and stirred at room temperature for 20 min. To the mixture was added 0.4 g (2.2 mmol) of benzenesulfonyl chloride and the reaction was refluxed for 2 hr. The reaction was cooled, diluted with 15 mL of water and extracted three times with 20 mL each of ethyl acetate. The combined organics were dried (MgSO$_4$), filtered and concentrated in vacuo. Chromatography (150 g of silica gel, 25% ethyl acetate/hexane) of the residue afforded 0.55 g (43%) of the title compound, 0.21g (16%) of the mixture of 5R- and 5S-diastereomers and 0.05 g (4%) of the 5R isomer.

Analysis calculated for $C_{37}H_{42}N_2O_6S$: %C, 69.14; %H, 6.59; %N, 4.36. Found: %C, 69.41; %H, 6.67; %N, 4.60.

Field Desorption Mass Spectrum: M=642.

B. A mixture of 0.51 g (0.8 mmol) of the compound from Example 66A and 1.3 g (4.0 mmol) of barium hydroxide in 10 mL of water was heated to reflux for 18 hr. The mixture was cooled and acidified to pH 3 with 4N sulfuric acid and heated to reflux for 1 hr. While hot, the mixture was filtered through celite and the filtrate was concentrated in vacuo. The resulting solid was suspended in 0.5 mL of water and ten drops of 1N sodium hydroxide were added. The mixture was then filtered and the filtrate acidified to pH 2 with 1N hydrochloric acid, whereupon a precipitate formed. The precipitate was filtered, washed with water, acetone and ether, then dried in vacuo at 60° C. to afford 20 mg (7%) of the title compound.

Analysis calculated for $C_{20}H_{21}NO_4 \cdot 0.75$ H$_2$O: %C, 68.07; %H, 6.43; %N, 3.97. Found: %C, 68.45; %H, 6.39; %N, 4.09.

Field Desorption Mass Spectrum: M=339.

$[\alpha]_D^{20}$=−18.9° (c=0.3, 1N NaOH)

EXAMPLE 67

Preparation of 2R-2-amino-2-(1S,2S-2-carboxycyclopropan-1-yl)-4-(3-methylphenyl)butanoic acid A. ((1S,2S-2-(1R, 2S,5R-Carbomenthyloxy) cycloprop-1-yl) (2-(3-methylphenyl)ethyl) ketone: A solution of 5.4 g (22 mmol) of 1-iodo-2-(3-methylphenyl)ethane and 3.4 g (52 mmol) of zinc/copper couple in 66 mL of benzene and 8 mL of N,N-dimethylacetamide was stirred for 3 hr at 60° C., then treated with 0.9 g (0.8 mmol) of tetrakis (triphenylphosphine)palladium(0) and heated for 5 min more. The heating bath was removed, 5.7 g (20 mmol) of the material from Preparation 5 was added and the mixture stirred at room temperature for 1 hr. The mixture was diluted with 60 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (250 g of silica gel, 5% ethyl acetate/hexane) of the residue afforded 4.6 g (61%) of the title compound.

Analysis calculated for $C_{24}H_{34}O_3$: %C, 77.80; %H, 9.25. Found: %C, 78.06; %H, 9.26.

$[\alpha]_D^{20}$=+105° (c=1, CH$_2$Cl$_2$).

B. (1S,2S-2-carboxycycloprop-1-yl) (2-(3-methylphenyl)ethyl) ketone: A solution of 4.4 g (11.8 mmol) of the compound from Example 67A in 25 mL of ethanol and 13 mL of in sodium hydroxide was stirred 18 hr at 55° C., then concentrated in vacuo. The residue was dissolved in 30 mL of water, extracted three times with 10 mL each of ether, then the aqueous layer was brought to pH 1 with concentrated hydrochloric acid. The resulting solution was extracted three times with 10 mL each of ether, then the combined organics were dried (MgSO$_4$), filtered and concentrated in vacuo to afford 2.3 g (85%) of the title compound.

C. 5SR- 5-(1S2S-2-carboxycyclopropan-1-yl)-5-(2-(3-methylphenyl)ethyl)imidazolidine-2,4-dione: A solution of 2.3 g (10.0 mmol) of the compound from Example 67B in 20 mL of ethanol was added to a solution of 3.2 g (50.0 mmol) of potassium cyanide and 7.0 g (90.0 mmol) of ammonium carbonate in 20 mL of water, then this mixture was heated to 55° C. for 24 hr. The mixture was cooled and added to 150 mL of 10% aqueous sodium bisulfate. The resulting mixture was allowed to stand at room temperature, then the solid was filtered, and recrystallization from acetone and water afforded 2.6 g (89%) of the title compound.

D. 5R-(1S,2S-2-(carbo(4-methoxy)benzyloxy) cyclopropan-1-yl)-3-(4-methoxybenzyl)-5-(2-(3-methylphenyl)ethyl)imidazolidine-2,4-dione and 5S-(1S, 2S-2-(carbo(4-methoxy)benzyloxy)cyclopropan-1-yl)-3-(4-methoxybenzyl)-5-(2-(3-methylphenyl)ethyl)imidazolidine-2,4-dione: A solution of 2.6 g (8.9 mmol) of the compound from Example 67C and 2.5 g (25.1 mmol) of potassium bicarbonate in 30 mL of N,N-dimethylformamide was treated with 3.2 g (20.6 mmol) of 4-methoxybenzyl chloride and heated to 130° C. for 3 hr. The mixture was diluted with 30 mL of ether and 60 mL of water. The organic layer was removed and the aqueous layer was extracted three times with 30 mL each of ether, then the combined organics were dried (MgSO$_4$), filtered and concentrated in vacuo. Chromatography (250 g of silica gel, 30% ethyl acetate/hexane) of the residue afforded 1.6 g (33%) of the 5R-isomer of title compound (higher R$_f$ material) and 1.6 g (33%) of the 5S-isomer of title compound (lower R$_f$ material).

5R-isomer: Analysis calculated for $C_{32}H_{34}N_2O_6$: %C, 70.83; %H, 6.32; %N, 5.16. Found: %C, 70.92; %H, 6.34; %N, 5.31.

Field Desorption Mass Spectrum: M=542.

$[\alpha]_D^{20}$=+48.4° (c=1, CH$_2$Cl$_2$).

5S-isomer: Analysis calculated for $C_{32}H_{34}N_2O_6$: %C, 70.83; %H, 6.32; %N, 5.16. Found: %C, 70.71; %H, 6.28; %N, 5.31.

Field Desorption Mass Spectrum: M=542.

$[\alpha]_D^{20}$=+67.4° (c=1, CH$_2$Cl$_2$).

E. 5R- 5-(1S,2S-2-carboxycyclopropan-1-yl)-5-(2-(3-methylphenyl)ethyl)imidazolidine-2,4-dione: A solution of 1.5 g (2.8 mmol) of the 5R-isomer from Example 67D in 90 mL of acetonitrile was added to a solution of 12.3 g (22.4 mmol) of ceric ammonium nitrate in 30 mL of water, then this mixture was stirred at room temperature for 2.5 hr. The mixture was diluted with 90 mL of brine. The organic layer was separated and the aqueous layer was extracted four times with 30 mL each of ethyl acetate, then the combined organics were dried (MgSO$_4$), filtered and concentrated in vacuo. Chromatography (150 g of silica gel, 2% glacial acetic acid/50% ethyl acetate/48% hexane) of the residue afforded 0.49 g (60% of the title compound.

F. A solution of 0.49 g (1.7 mmol) of the compound from Example 67E and 2.7 g (8.5 mmol) of barium hydroxide in 10 mL of water was heated to 200° C. for 24 hr in a stainless steel high pressure reactor. The mixture was cooled and acidified to pH 7 with 0.5 mL (8.5 mmol) of concentrated sulfuric acid. The resulting solution was heated at 100° C. for 1 hr, then the solid was filtered and washed three times with 10 mL each of water. Cation exchange chromatography of the filtrate afforded a solid that was suspended in water and filtered, washed with water, acetone and ether and dried in vacuo at 60° C. to afford 0.21 g (44%) of the title compound.

Analysis calculated for $C_{15}H_{19}NO_4$: %C, 64.97; %H, 6.91; %N, 5.05. Found: %C, 64.49; %H, 6.75; %N, 5.45.

Field Desorption Mass Spectrum: M=277.

$[\alpha]_D^{20}$=+46.0° (c=0.5, 1N NaOH).

G. Alternative preparation of 5SR- 5-(1S2S-2-carboxycyclopropan-1-yl)-5-(2-(3-methylphenyl)ethyl)imidazolidine-2,4-dione: A solution of 25.5 g (69.0 mmol) of the compound from Example 67A in 150 mL of ethanol and 76 mL of 1N sodium hydroxide was stirred 24 hr at 55° C. 22.4 g (344.0 mmol) of potassium cyanide, 48.3 g (619.0 mmol) of ammonium carbonate and 75 mL of water were added and the mixture was heated to 55° C. for 24 hr. The mixture was cooled and added to 350 mL of 5N hydrochloric acid. The resulting mixture was allowed to stand at room temperature, then the solid was filtered, and recrystallization from acetone and water afforded 18.1 g (90%) of the title compound.

H. Alternative preparation of 5R-(1S,2S-2-(carbo(4-methoxy)benzyloxy)cyclopropan-1-yl)-3-(4-methoxybenzyl)-5-(2-(3-methylphenyl)ethyl)imidazolidine-2,4-dione and 5S-(1S,2S-2-(carbo(4-methoxy)benzyloxy)cyclopropan-1-yl)-3-(4-methoxybenzyl)-5-(2-(3-methylphenyl)ethyl)imidazolidine-2,4-dione: A solution of 2.6 g (8.9 mmol) of the compound from Example 67G and 2.5 g (25.1 mmol) of potassium bicarbonate in 30 mL of N,N-dimethylformamide was treated with 3.2 g (20.6 mmol) of 4-methoxybenzyl chloride and heated to 130° C. for 3 hr. The mixture was diluted with 30 mL of ether and 60 mL of water. The organic layer was removed and the aqueous layer was extracted three times with 30 mL each of ether, then the combined organics were dried (MgSO$_4$), filtered and concentrated in vacuo. Chromatography (250 g of silica gel, 30% ethyl acetate/hexane) of the residue afforded 1.6 g (33%) of the 5R-isomer of title compound (higher R$_f$ material) and 1.6 g (33%) of the 5S-isomer of title compound (lower R$_f$ material).

5R-isomer: Analysis calculated for $C_{32}H_{34}N_2O_6$: %C, 70.83; %H, 6.32; %N, 5.16. Found: %C, 70.92; %H, 6.34; %N, 5.31.

Field Desorption Mass Spectrum: M=542.

$[\alpha]_D^{20}$=+48.4° (c=1, CH$_2$Cl$_2$).

5S-isomer: Analysis calculated for $C_{32}H_{34}N_2O_6$: %C, 70.83; %H, 6.32; %N, 5.16. Found: %C, 70.71; %H, 6.28; %N, 5.31.

Field Desorption Mass Spectrum: M=542.

$[\alpha]_D^{20}$=+67.4° (c=1, CH$_2$Cl$_2$).

EXAMPLE 68

Preparation of 2S-2-amino-2-(1S,2S-2-carboxycyclopropan-1-yl)-4-(3-methylphenyl)butanoic acid A. 5S 5-(1S2S-2-carboxycyclopropan-1-yl)-5-(2-(3-methylphenyl)ethyl)imidazolidine-2,4-dione: A solution of 1.4 g (2.5 mmol) of the 5R-isomer from Example 67D in 80 mL of acetonitrile was added to a solution of 10.9 g (19.9 mmol) of ceric ammonium nitrate in 25 mL of water, then this mixture was stirred at room temperature for 2.5 hr. The mixture was diluted with 80 mL of brine. The organic layer was separated and the aqueous layer was extracted four times with 50 mL each of ethyl acetate, then the combined organics were dried (MgSO$_4$), filtered and concentrated in vacuo. Chromatography (150 g of silica gel, 2% glacial acetic acid/50% ethyl acetate/48%hexane) of the residue afforded 0.35 g (48% of the title compound.

B. A solution of 0.35 g (1.2 mmol) of the compound from Example 68E and 1.9 g (6.0 mmol) of barium hydroxide in 10 mL of water was heated to 200° C. for 24 hr in a stainless steel high pressure reactor. The mixture was cooled and acidified to pH 7 with 0.33 mL (6.0 mmol) of concentrated sulfuric acid. The resulting solution was heated at 100° C. for 1 hr., then the solid was filtered and washed three times with 10 mL each of water. Cation exchange chromatography of the filtrate afforded a solid that was suspended in water and filtered, washed with water, acetone and ether and dried in vacuo at 60° C. to afford 0.11 g (34%) of the title compound.

Analysis calculated for $C_{15}H_{19}NO_4 \cdot 0.25\ H_2O$: %C, 63.93; %H, 6.97; %N, 4.97. Found: %C, 64.04 %H, 6.82; %N, 5.03.

Field Desorption Mass Spectrum: M=277.

$[\alpha]_D^{20}$=+62.0° (c=0.5, 1N NaOH).

C. Alternative preparation of 2S-2-amino-2-(1S,2S-2-carboxycyclopropan-1-yl)-4-(3-methylphenyl)butanoic acid A solution of 7.3 g (13.4 mmol) of the compound from Example 63H in 100 mL of 1N sodium hydroxide was heated to 200° C. for 24 hr in a stainless steel high pressure reactor. The mixture was cooled, washed three times with 30 mL each of ether, then acidified to pH 7 with concentrated hydrochloric acid. Cation exchange chromatography of this solution afforded a solid that was suspended in water and filtered, washed with water, acetone and ether and dried in vacuo at 60° C. to afford 1.9 g (50%) of the title compound.

Analysis calculated for $C_{15}H_{19}NO_4 \cdot 0.25 \, H_2O$: %C, 63.93; %H, 6.97; %N, 4.97. Found: %C, 64.04 %H, 6.82; %N, 5.03.

Field Desorption Mass Spectrum: M=277.

$[\alpha]_D^{20} = +62.0°$ (c=0.5, 1N NaOH).

EXAMPLE 69

Preparation of 2R-2-amino-2-(1R,2R-2-carboxycyclopropan-1-yl)-4-(3-methylphenyl)butanoic acid A. 1R,2R,2-(1S,2R,5S-carbomenthyloxy)cycloprop-1-yl) (2-(3-methylphenyl)ethyl) ketone: A solution of 5.7 g (23.0 mmol) of 1-iodo-2-(3-methylphenyl)ethane and 2.9 g (44.2 mmol) of zinc/copper couple in 65 mL of benzene and 6.5 mL of dimethylacetamide was stirred for 2.5 hr at 60° C. The heating bath was removed and the mixture was treated with 0.44 g (0.38 mmol) of tetrakis(triphenylphosphine)palladium(0). After 10 min, 5.5 g (19.2 mmol) of the material from Preparation 6 was added and the mixture stirred at room temperature for 1 hr. The mixture was diluted with 65 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried ($MgSO_4$), filtered and concentrated in vacuo. Chromatography (400 g of silica gel, 10% ethyl acetate/hexane) of the residue afforded 4.7 g (65%) of the title compound.

Analysis calculated for $C_{24}H_{34}O_3$: %C, 77.80; %H, 9.25. Found: %C, 78.06; %H, 9.26.

Field Desorption Mass Spectrum: M=371.

$[\alpha]_D^{20} = -98.3°$ (c=1, $CH_2Cl_2$).

B. (1R,2R-2-carboxycycloprop-1-yl) (2-(3-methylphenyl)ethyl) ketone: A solution of 4.4 g (11.8 mmol) of the compound from Example 69A in 35 mL of ethanol and 14.3 mL of 1N sodium hydroxide was stirred 18 hr at 65° C., then concentrated in vacuo. The residue was dissolved in 30 mL of water, extracted three times with 10 mL each of ether, then brought to pH 2 with 10% aqueous sodium bisulfate. The resulting solution was extracted four times with 15 mL each of ethyl acetate, then the combined organics were dried ($MgSO_4$), filtered and concentrated in vacuo at 60° C. to afford 2.3 g (95%) of the title compound.

Analysis calculated for $C_{14}H_{16}O_3$: %C, 72.39; %H, 6.94. Found: %C, 72.23; %H, 6.98.

Field Desorption Mass Spectrum: M=232.

$[\alpha]_D^{20} = -227.4°$ (c=1, $CH_2Cl_2$).

C. 5SR-5-(1R2R-2-carboxycyclopropan-1-yl)-5-(2-(3-methylphenyl)ethyl)imidazolidine-2,4-dione: A solution of 2.4 g (10.3 mmol) of the compound from Example 69B in 16 mL of ethanol was added to a solution of 3.4 g (51.7 mmol) of potassium cyanide and 8.9 g (93.0 mmol) of ammonium carbonate in 16 mL of water, then this mixture was heated to 55° C. for 24 hr. The mixture was cooled and added to 200 mL of 10% aqueous sodium bisulfate. The resulting mixture was allowed to stand at room temperature, then the solid thus obtained was filtered, and recrystallization from acetone and water afforded 2.0 g (63%) of the title compound.

D. 5S-(1R,2R-2-(carbo(4-methoxy)benzyloxycyclopropan-1-yl)-3-(4-methoxybenzyl)-5-(2-(3-methylphenyl)ethyl)imidazolidine-2,4-dione and 5R-(1R,2R-2-(carbo(4-methoxy)benzyloxycyclopropan-1-yl)-3-(4-methoxybenzyl)-5-(2-(3-methylphenyl)ethyl)imidazolidine-2,4-dione: A solution of 2.0 g (6.5 mmol) of the compound from Example 69C and 1.8 g (18.3 mmol) of potassium bicarbonate in 25 mL of dimethylformamide was treated with 2.4 g (15.0 mmol) of 4-methoxybenzyl chloride and heated to 125° C. for 3 hr. The mixture was diluted with 60 mL of water, the organic layer was extracted twice with 30 mL each of ethyl acetate, then the combined organics were dried ($MgSO_4$), filtered and concentrated in vacuo. Chromatography (300 g of silica gel, 30% ethyl acetate/hexane) of the residue afforded 1.7 g (48%) of the 5S-isomer of title compound (higher $R_f$ material) and 1.2 g (34%) Of the 5R-isomer of the title compound (lower $R_f$ material).

5S-isomer: Analysis calculated for $C_{32}H_{34}N_2O_6$: %C, 70.83; %H, 6.32; %N, 5.16. Found: %C, 70.86; %H, 6.37; %N, 5.22.

Field Desorption Mass Spectrum: M=542.

$[\alpha]_D^{20} = -51.8°$ (c=1, $CH_2Cl_2$).

5R-isomer: Analysis calculated for $C_{32}H_{34}N_2O_6 \cdot 0.05 \, CHCl_3$: %C, 70.17; %H, 6.26; %N, 5.11. Found: %C, 70.27; %H, 6.31; %N, 5.08.

Field Desorption Mass Spectrum: M=542.

$[\alpha]_D^{20} = -67.8°$ (c=1, $CH_2Cl_2$).

E. 5R- 5-(1R,2R-2-carboxycyclopropan-1-yl)-5-(2-(3-methylphenyl)ethyl)imidazolidine-2,4-dione: A solution of 1.0 g (1.9 mmol) of the 5R-isomer from Example 69D in 60 mL of acetonitrile was added to a solution of 8.3 g (15.2 mmol of ceric ammonium nitrate in 20 mL of water, then this mixture was stirred at room temperature for 2.5 hr. The mixture was diluted with 60 mL of brine and extracted four times with 20 mL each of ethyl acetate, then the combined organics were dried ($MgSO_4$), filtered and concentrated in vacuo. Chromatography (50 g of silica gel, 2% glacial acetic acid/50% ethyl acetate/48%hexane) of the residue afforded a solid which was recrystallized from water/acetone. The crystals were filtered, rinsed with water, and dried in vacuo at 60° C. to afford 0.25 g (42%) of the title compound.

Field Desorption Mass Spectrum: M=303.

F. A solution of 0.53 g (1.75 mmol) of the compound from Example 69E and 2.8 g (8.8 mmol) of barium hydroxide in 15 mL of water was heated to 250° C. for 16 hr in a stainless steel high pressure reactor. The mixture was cooled and acidified to pH 2 with concentrated sulfuric acid. The resulting solution was heated at 90° C. for 1 hr., then the solid was filtered through celite and washed three times with 10 mL each of water and three times with 10 mL each of 0.33N sodium hydroxide. Concentrated in vacuo to a 10 mL volume. Cation exchange chromatography of the filtrate afforded a solid that was suspended in water and filtered, washed with water, acetone and ether and dried in vacuo at 60° C. to afford 0.09 g (19%) of the title compound.

Analysis calculated for $C_{15}H_{19}NO_0$: %C, 64.97; %H, 6.91; %N, 5.05. Found: %C, 64.73; %H, 6.78; %N, 5.09.

$[\alpha]_D^{20} = -28.3°$ (c=0.5, 1N NaOH).

EXAMPLE 70

Preparation of 2S-2-amino-2-(1R,2R,2-carboxycyclopropan-1-yl)-4-(3-methylphenyl)butanoic acid A. 5S-5-(1R,2R-2-carboxycyclopropan-1-yl)-5-(2-(3-methylphenyl)ethyl)imidazolidine-2,4-dione: A solution of 1.6 g (2.9 mmol) of the 5S-isomer from Example 69D in 90 mL of acetonitrile was added to a solution of 12.5 g (22.9 mmol) of ceric ammonium nitrate in 30 mL of water, then this mixture was stirred at room temperature for 2.5 hr. The mixture was diluted with 60 mL of brine and extracted four times with 40 mL each of ethyl acetate, then the combined organics were dried (MgSO$_4$), filtered and concentrated in vacuo. Chromatography (200 g of silica gel, 2% glacial acetic acid/50% ethyl acetate/48%hexane) of the residue afforded a solid which was recrystallized from water/acetone. The crystals were filtered, rinsed with water, and dried in vacuo at 60° C. to afford 0.44 g (50%) of the title compound.

B. A solution of 0.44 g (1.4 mmol) of the compound from Example 70E and 2.3 g (7.2 mmol) of barium hydroxide in 12 mL of water was heated to 250° C. for 16 hr in a stainless steel high pressure reactor. The mixture was cooled and acidified to pH 2 with concentrated sulfuric acid. The resulting solution was heated at 90° C. for 1 hr., then the solid was filtered and washed three times with 10 mL each of water. The filtrate was concentrated in vacuo to a volume of 10 mL. Cation exchange chromatography of the filtrate afforded a solid that was dissolved in water and concentrated in vacuo. The resulting solid was suspended in acetone, filtered and washed with acetone and ether, then dried in vacuo at 60° C. to afford 21 mg (5%) of the title compound.

Analysis calculated for $C_{15}H_{19}NO_4 \cdot 0.75\ H_2O$: %C, 61.95; %H, 7.10; %N, 4.82. Found: %C, 62.31; %H, 6.65; %N, 4.94.

Field Desorption Mass Spectrum: M=278.

$[\alpha]_D^{20} = -56.0°$ (c=0.5, 1N NaOH).

EXAMPLE 71

Preparation of 2R-2 amino-2-(1S,2S-2-carboxycyclopropan-1-yl)-3-(dibenzopyran-4-yl)propanoic acid A. ((1S,2S-2-(1R,2S,5R-Carbomenthyloxy)cycloprop-1-yl) ((dibenzopyran-4-yl)methyl) ketone: A solution of 11.3 g (35 mmol) of (dibenzopyran-4-yl)methyl iodide and 5.5 g (84 mmol) of zinc/copper couple in 115 mL of benzene and 16 mL of N,N-dimethylacetamide was stirred for 3 hr at 60° C., then treated with 1.6 g (1.4 mmol) of tetrakis(triphenylphosphine)palladium(0) and heated for 5 min more. The heating bath was removed, 10 g (35 mmol) of the material from Preparation 5 was added and the mixture stirred at room temperature for 1 hr. The mixture was diluted with 115 mL of ethyl acetate and filtered through diatomaceous earth. The filtrate was washed with 200 mL of 10% aqueous sodium bisulfate, 200 mL of saturated aqueous sodium bicarbonate and 200 mL of saturated aqueous sodium chloride. The organic layer was dried (MgSO$_4$), filtered and concentrated in vacuo. Chromatography (500 g of silica gel, 10% ethyl acetate/hexane) of the residue afforded 9.6 g (61%) of the title compound.

Analysis calculated for $C_{29}H_{34}O_4$: %C, 78.00; %H, 7.67. Found: %C, 78.22; %H, 7.63.

$[\alpha]_D^{20} = +64.2°$ (c=1, CH$_2$Cl$_2$).

B. (1S,2S-2-carboxycycloprop-1-yl) ((dibenzopyran-4-yl)methyl) ketone: A solution of 9.0 g (20 mmol) of the compound from Example 71A in 45 mL of ethanol and 22.2 mL of in sodium hydroxide was stirred 24 hr at 60° C., then concentrated in vacuo. The residue was dissolved in 100 mL of water and extracted four times with 30 mL each of ether, then the aqueous layer was brought to pH 1 with concentrated hydrochloric acid. The resulting solution was extracted three times with 50 mL each of ether, then the combined organics were dried (MgSO$_4$), filtered and concentrated in vacuo at 60° C. to afford 5.4 g (87%) of the title compound.

C. 5SR-5-(1SR,2SR-2-carboxycyclopropan-1-yl)-5-((dibenzopyran-4-yl)methyl)imidazolidine-2,4-dione: A solution of 5.3 g (17.2 mmol) of the compound from Example 71B in 30 mL of ethanol was added to a solution of 5.6 g (85.9 mmol) of potassium cyanide and 12.1 g (155 mmol) of ammonium carbonate in 30 mL of water, then this mixture was heated to 55° C. for 72 hr. The mixture was cooled and added to 200 mL of 10% aqueous sodium bisulfate. The resulting mixture was allowed to stand at room temperature, then the solid was filtered, and recrystallization from acetone and water afforded 3.8 g (59%) of the title compound.

D. 5R-(1S,2S-2-(carbo(4-methoxy)benzyloxy)cyclopropan-1-yl)-5-((dibenzopyran-4-yl)methyl)-3-(4-methoxybenzyl)imidazolidine-2,4-dione and 5S-(1S,2S-2-(carbo(4-methoxy)benzyloxy)cyclopropan-1-yl)-5-((dibenzopyran-4-yl)methyl)-3-(4-methoxybenzyl)imidazolidine-2,4-dione: A solution of 3.8 g (10 mmol) of the compound from Example 71C and 2.8 g (28 mmol) of potassium bicarbonate in 30 mL of N,N-dimethylformamide was treated with 3.6 g (23 mmol) of 4-methoxybenzyl chloride and heated to 125° C. for 2 hr. The mixture was diluted with 30 mL of ether and 60 mL of water. The organic layer was removed and the aqueous layer was extracted three times with 20 mL each of ether, then the combined organics were dried (MgSO$_4$), filtered and concentrated in vacuo. Chromatography (600 g of silica gel, 30% ethyl acetate/hexane) of the residue afforded 2.3 g (38%) of the 5R-isomer of title compound (higher R$_f$ material) and 2.2 g (36%) Of the 5S-isomer of title compound (lower R$_f$ material).

5R-isomer: Analysis calculated for $C_{37}H_{34}N_2O_7$: %C, 71.83; %H, 5.54; %N, 4.53. Found: %C, 71.73; %H, 5.28; %N, 4.55.

Field Desorption Mass Spectrum: M–2=616.

$[\alpha]_D^{20} = +60.4°$ (c=1, CH$_2$Cl$_2$).

5S-isomer: Analysis calculated for $C_{37}H_{34}N_2O_7$: %C, 71.83; %H, 5.54; %N, 4.53. Found: %C, 71.86; %H, 5.74; %N, 4.50.

Field Desorption Mass Spectrum: M–2=616.

$[\alpha]_D^{20} = +85.2°$ (c=1, CH$_2$Cl$_2$).

E. A solution of 2.3 g (3.7 mmol) of the 5R-isomer from Example 71D and 5.9 g (18.6 mmol) of barium hydroxide in 25 mL of water was heated to 200° C. for 24 hr in a stainless steel high pressure reactor. The mixture was cooled and acidified to pH 7 with 1.0 mL (18.6 mmol) of concentrated sulfuric acid. The resulting solution was heated at 100° C. for 1 hr, then the solid was filtered and washed three times with 10 mL each of water. Cation exchange chromatography of the filtrate afforded a solid that was suspended in water and filtered, washed with water, acetone and ether and dried in vacuo at 60° C. to afford 0.15 g (11%) of the title compound.

Analysis calculated for $C_{20}H_{19}NO_5$: %C, 67.98; %H, 5.42; %N, 3.96. Found: %C, 68.24 %H, 5.55; %N, 4.01.

Field Desorption Mass Spectrum: M=353.

$[\alpha]_D^{20}$=+46.0° (c=0.5, 1N NaOH).

F. Alternative preparation of 5SR-5-(1SR,2SR-2-carboxycyclopropan-1-yl)-5-((dibenzopyran-4-yl)methyl)imidazolidine-2,4-dione: A solution of 26.6 g (59.6 mmol) of the compound from Example 71A in 135 mL of ethanol and 65.5 mL of 1N sodium hydroxide was stirred 24 hr at 55° C. 19.4 g (298.0 mmol) of potassium cyanide, 41.8 g (536 mmol) of ammonium carbonate and 65 mL of water were added, then this mixture was heated to 55° C. for 48 hr. The mixture was cooled, extracted once with 100 mL of ether then added to 300 mL of 5N hydrochloric acid. The resulting mixture was allowed to stand at room temperature, then the solid was filtered, and recrystallization from acetone and water afforded 11.5 g (51%) of the title compound.

G. Alternative preparation of 5R-(1S,2S-2-(carbo(4-methoxy)benzyloxy)cyclopropan-1-yl)-5-((dibenzopyran-4-yl)methyl)-3-(4-methoxybenzyl)imidazolidine-2,4-dione and 5S-(1S,2S-2-(carbo(4-methoxy)benzyloxy)cyclopropan-1-yl)-5-((dibenzopyran-4-yl)methyl)-3-(4-methoxybenzyl)imidazolidine-2,4-dione: A solution of 3.8 g (10 mmol) of the compound from Example 71F and 2.8 g (28 mmol) of potassium bicarbonate in 30 mL of N,N-dimethylformamide was treated with 3.6 g (23 mmol) of 4-methoxybenzyl chloride and heated to 125° C. for 2 hr. The mixture was diluted with 30 mL of ether and 60 mL of water. The organic layer was removed and the aqueous layer was extracted three times with 20 mL each of ether, then the combined organics were dried (MgSO$_4$), filtered and concentrated in vacuo. Chromatography (600 g of silica gel, 30% ethyl acetate/hexane) of the residue afforded 2.3 g (38%) of the 5R-isomer of title compound (higher R$_f$ material) and 2.2 g (36%) of the 5S-isomer of title compound (lower R$_f$ material).

5R-isomer: Analysis calculated for $C_{37}H_{34}N_2O_7$: %C, 71.83; %H, 5.54; %N, 4.53. Found: %C, 71.73; %H, 5.28; %N, 4.55.

Field Desorption Mass Spectrum: M−2=616.

$[\alpha]_D^{20}$=+60.4° (c=1, CH$_2$Cl$_2$).

5S-isomer: Analysis calculated for $C_{37}H_{34}N_2O_7$: %C, 71.83; %H, 5.54; %N, 4.53. Found: %C, 71.86; %H, 5.74; %N, 4.50.

Field Desorption Mass Spectrum: M−2=616.

$[\alpha]_D^{20}$=+85.2° (c=1, CH$_2$Cl$_2$).

EXAMPLE 72

Preparation of 2S-2-amino-2-(1S,2S-2-carboxycyclopropan-1-yl)-3-(dibenzopyran-4-yl)propanoic acid A. A solution of 2.2 g (3.5 mmol) of the 5S-isomer from Example 71D and 5.6 g (17.8 mmol) of barium hydroxide in 25 mL of water was heated to 200° C. for 24 hr in a stainless steel high pressure reactor. The mixture was cooled and acidified to pH 7 with 0.9 mL (17.8 mmol) of concentrated sulfuric acid. The resulting solution was heated at 100° C. for 1 hr, then the solid was filtered and washed three times with 10 mL each of water. Cation exchange chromatography of the filtrate afforded a solid that was suspended in water and filtered, washed with water, acetone and ether and dried in vacuo at 60° C. to afford 0.23 g (19%) of the title compound.

Analysis calculated for $C_{20}H_{19}NO_5$.0.5 H$_2$O: %C, 66.29; %H, 5.23; %N, 3.44. Found: %C, 66.01%H, 5.56; %N, 3.87.

Field Desorption Mass Spectrum: M=353.

$[\alpha]_D^{20}$=+36.0° (c=0.5, 1N NaOH).

B. Alternative preparation of 2S-2-amino-(1S,2S-2-carboxycyclopropan-1-yl)-3-(dibenzopyran-4-yl)propanoic acid. A solution of 5.2 g (8.4 mmol) of the 5S-isomer from Example 71G in 100 mL of 1N sodium hydroxide was heated to 200° C. for 24 hr in a stainless steel high pressure reactor. The mixture was cooled, extracted three times with 30 mL each of ether, then acidified to pH 7 with concentrated hydrochloric acid. Cation exchange chromatography of this solution afforded a solid that was suspended in water and filtered, washed with water, acetone and ether and dried in vacuo at 60° C. to afford 1.5 g (52%) of the title compound.

Analysis calculated for $C_{20}H_{19}NO_5$.0.5 H$_2$O: %C, 66.29; %H, 5.23; %N, 3.44. Found: %C, 66.01%H, 5.56; %N, 3.87.

Field Desorption Mass Spectrum: M=353.

$[\alpha]_D^{20}$=+36.0° (c=0.5, 1N NaOH).

EXAMPLE 73

Preparation of 2S-2 amino-2-(1R,2R-2-carboxycyclopropan-1-yl)-3-(dibenzopyran-4-yl)propanoic acid A. (1R,2R-2-(1S,2R,5S-carbomenthyloxy)cycloprop-1-yl) ((dibenzopyran-4-yl)methyl) ketone: A solution of 6.7 g (20.7 mmol) of (dibenzopyran-4-yl)methyl iodide and 2.6 g (39.6 mmol) of zinc/copper couple in 60 mL of benzene and 6 mL of N,N-dimethylacetamide was stirred for 2.5 hr at 60° C. The heating bath was removed then 0.4 g (0.34 mmol) of tetrakis(triphenylphosphine)palladium(0) was added. After 10 min, 4.9 g (17.2 mmol) of the material from Preparation 6 was added and the mixture stirred at room temperature for 1 hr. The mixture was diluted with 60 mL of ethyl acetate and filtered through diatomaceous earth. The filtrate was washed with 75 mL of 10% aqueous sodium bisulfate, 75 mL of saturated aqueous sodium bicarbonate and 50 mL of saturated aqueous sodium chloride. The organic layer was dried (MgSO$_4$), filtered and concentrated in vacuo. Chromatography (500 g of silica gel, 10% ethyl acetate/hexane) of the residue afforded 5.0 g (65%) of the title compound.

Analysis calculated for $C_{29}H_{34}O_4$: %C, 78.00; %H, 7.67. Found: %C, 78.51; %H, 7.01.

Field Desorption Mass Spectrum: M=446.

$[\alpha]_D^{20}$=−85.0° (c=1, CH$_2$Cl$_2$).

B. (1R,2R-2-carboxycycloprop-1-yl) ((dibenzopyran-4-yl)methyl) ketone: A solution of 4.7 g (10.5 mmol) of the compound from Example 73A in 30 mL of ethanol and 11.5 mL of 1N sodium hydroxide was stirred 7 hr at 65° C., then 5.2 mL (5.2 mmol) more 1N sodium hydroxide was added. The reaction mixture was stirred for an additional 16 hr at 60° C. The mixture was concentrated in vacuo and the residue was dissolved in 50 mL of water and extracted three times with 50 mL each of ether, then brought to pH 1 with 10% aqueous sodium bisulfate. The resulting solution was extracted three times with 50 mL each of ethyl acetate, then the combined organics were dried (MgSO$_4$), filtered and concentrated in vacuo to afford 3.1 g (95%) of the title compound.

Field Desorption Mass Spectrum: M=309.

$[\alpha]_D^{20}$=−157.1° (c=1, CH$_2$Cl$_2$).

C. 5SR-5-(1R,2R-2-carboxycyclopropan-1-yl)-5-((dibenzopyran-4-yl)methyl)imidazolidine-2,4-dione: A solution of 7.12 g (23.1 mmol) of the compound from Example 73B in 40 mL of ethanol was added to a solution of 7.52 g (115.5 mmol) of potassium cyanide and 19.97 g (207.4 mmol) of ammonium carbonate in 40 mL of water, then this mixture was heated to 55° C. for 120 hr. The mixture was cooled and added to 400 mL of 10% aqueous sodium bisulfate. The resulting mixture was allowed to stand at room temperature, then the solid was filtered, and recrystallization from acetone and water afforded 6.78 g (78%) of the title compound.

D. 5S-5-(1R,2R-2-(carbo(4-methoxybenzyl)oxy) cyclopropan-1-yl)-5-((dibenzopyran-4-yl)methyl)-3-(4-methoxybenzyl)imidazolidine-2,4-dione and 5R-5-(1R,2R-2-(carbo(4-methoxybenzyl)oxy)cyclopropan-1-yl)-5-((dibenzopyran-4-yl)methyl)-3-(4-methoxybenzyl) imidazolidine-2,4-dione: A solution of 5.8 g (15.3 mmol) of the compound from Example 73C and 4.3 g (42.8 mmol) of potassium bicarbonate in 60 mL of N,N-dimethylformamide was treated with 5.51 g (35.2 mmol) of 4-methoxybenzyl chloride and heated to 125° C. for 3 hr. The mixture was diluted with 60 mL of water and extracted three times with 30 mL each of ethyl acetate, then the combined organics were dried (MgSO$_4$), filtered and concentrated in vacuo. Chromatography (600 g of silica gel, 35% to 50% ethyl acetate/hexane) of the residue afforded afforded 4.0 g (43%) of the 5S-isomer of title compound (higher $R_f$ material) and 4.2 g (44%) of the 5R-isomer of the title compound (lower $R_f$ material).

5S-isomer: Analysis calculated for $C_{37}H_{34}N_2O_7$: %C, 71.83; %H, 5.54; %N, 4.53. Found: %C, 71.60; %H, 5.53; %N, 4.43.

Field Desorption Mass Spectrum: M-2=616.

$[\alpha]_D^{20}$=-87.8° (c=1, CH$_2$Cl$_2$).

5R-isomer: Analysis calculated for $C_{37}H_{34}N_2O_7$·0.25 H$_2$O: %C, 71.31; %H, 5.58; %N, 4.50. Found: %C, 71.35; %H, 5.65; %N, 4.56.

Field Desorption Mass Spectrum: M-2=616.

$[\alpha]_D^{20}$=-66.0° (c=1, CH$_2$Cl$_2$).

E. A mixture of 3.7 g (6.1 mmol) of the 5S-isomer from Example 73D and 9.5 g (30.3 mmol) of barium hydroxide in 40 mL of water was heated to 200° C. for 24 hr in a stainless steel high pressure reactor. The mixture was cooled and acidified to pH 2 with 4N sulfuric acid. The resulting solution was heated at 100° C. for 1 hr, then the solid was filtered and washed three times with 50 mL each of 0.2N sodium hydroxide. Cation exchange chromatography of the filtrate afforded 80 mg of a solid that was soluble in acetone. The filter cake from filtration after acidification was washed two times with 0.25N sodium hydroxide and once with 30 mL of water. After adjusting to pH 2 with 5N hydrochloric acid, cation exchange chromatography afforded a solid which was suspended in acetone, filtered, rinsed with acetone and ether, then dried in vacuo at 60° C. to afford 41 mg (2%) of the title compound.

Analysis calculated for $C_{20}H_{19}NO_5$·H$_2$O: %C, 64.68; %H, 5.70; %N, 3.77. Found: %C, 64.72 %H, 5.59; %N, 3.68.

Field Desorption Mass Spectrum: M=353.

$[\alpha]_D^{20}$=-24.0° (c=0.25, in NaOH).

EXAMPLE 74

Preparation of 2R-2- amino-2-(1R,2R-2-carboxycyclopropan-1-yl)-3-(dibenzopyran-4-yl)propanoic acid A. A solution of 4.0 g (6.5 mmol) of the 5R-isomer from Example 73D and 10.2 g (32.3 mmol) of barium hydroxide in 40 mL of water was heated to 200° C. for 24 hr in a stainless steel high pressure reactor. The mixture was cooled and acidified to pH 2 with 4N sulfuric acid. The resulting solution was filtered through diatomaceous earth and washed two times with 25 mL each of 0.25N sodium hydroxide. Cation exchange chromatography of the filtrate afforded a solid that was suspended in water and filtered, washed with water, acetone and ether and dried in vacuo at 60° C. to afford 1.0 g (43%) of the title compound.

Analysis calculated for $C_{20}H_{19}NO_5$·0.5 H$_2$O·0.05 C$_5$H$_5$N: %C, 66.39; %H, 5.57; %N, 4.01. Found: %C, 66.27 %H, 5.33; %N, 4.39 $[\alpha]_D^{20}$=-27.0° (c=1, 1N NaOH).

EXAMPLE 75

Preparation of 2SR- and 2RS-2-amino-2-(1SR,2SR-2-carboxycyclopropan-1-yl)-4-(3,5-dichlorophenyl) butanoic acid A. (1SR,2SR-2-carbethoxycycloprop-1-yl) (2-(3,5-dichlorophenyl)ethenyl) ketone: A solution of 3.0 g (11.3 mmol) of diethyl (1SR,2SR-2-carbethoxycycloprop-1-yl)-2-oxoethylphosphonate in 5 mL of tetrahydrofuran was added to a suspension of 0.45 g (11.3 mmol) sodium hydride in 30 mL of tetrahydrofuran and stirred for 20 min at room temperature. A solution of 2.0 g (11.3 mmol) of 3,5-dichlorobenzaldehyde in 5 mL of tetrahydrofuran was added and the mixture stirred for 2 hr at room temperature. The mixture was added to 80 mL of water and 40 mL of ether, the organic phase separated and the aqueous phase extracted three times with 20 mL each of ether. The combined organics were dried (MgSO$_4$), filtered and concentrated in vacuo to afford 2.9 g (83%) of the title compound after recrystallization from ethyl acetate/hexane.

Analysis calculated for $C_{15}H_{14}O_3Cl_2$: %C, 57.53; %H, 4.51. Found: %C, 57.74; %H, 4.47.

Field Desorption Mass Spectrum: M-1=312.

B. (1SR,2SR-2-carbethoxycycloprop-1-yl) (2-(3,5-dichlorophenyl)ethyl) ketone: A solution of 2.9 g (9.2 mmol) of the compound from Example 75A in 30 mL of ethanol and 0.6 g of 5% palladium on carbon was degassed (brief evacuation under vacuum for about 30 seconds followed by venting to nitrogen the first time and then to hydrogen the subsequent two times) and then stirred 24 hr at room temperature under hydrogen (in a balloon). The mixture was diluted with 30 mL of ethyl acetate, filtered through diatomaceous earth and concentrated in vacuo. Chromatography (150 g of silica gel, 10% ethyl acetate/hexane) of the residue afforded 1.7 g (60%) of the title compound.

C. (1SR,2SR-2-carboxycycloprop-1-yl) (2-(3,5-dichlorophenyl)ethyl) ketone: A solution of 1.7 g (5.4 mmol) of the compound from Example 75B in 12 mL of ethanol and 6.0 mL of 1N sodium hydroxide was heated to 55° C. for 4 hr. The mixture was cooled and then concentrated in vacuo. The residue was dissolved in 10 mL of 5N hydrochloric acid and 6 mL brine, extracted three times with 10 mL each of ether, then the combined organics were dried (MgSO$_4$), filtered and concentrated in vacuo at 60° C. to afford 1.2 g (78%) of the title compound.

D. 5SR- and 5RS-5-(1SR,2SR-2-carboxycyclopropan-1-yl)-5-(2-(3,5-dichlorophenyl)ethyl)imidazolidine-2,4-dione: A solution of 1.2 g (4.2 mmol) of the compound from Example 75C in 14 mL of ethanol was added to a solution of 1.4 g (21.2 mmol) of potassium cyanide and 3.0 g (38.2 mmol) of ammonium carbonate in 12 mL of water, then this mixture was heated to 55° C. for 24 hr. The mixture was cooled and added to 100 mL of 10% aqueous sodium bisulfate. The resulting mixture was allowed to stand at room temperature, then the solid was filtered, and recrystallization from acetone and water afforded 0.9 g (60%) of the title compound.

E. 5 mL (5.0 mmol) of in sodium bis(trimethylsilyl)amide was added to a solution containing 0.9 g (2.5 mmol) of the compound from Example 75D and 0.7 g (5.0 mmol) of N,N-diisopropylethylamine in 8 mL of tetrahydrofuran. The mixture was stirred 20 min., then 1.0 g (5.0 mmol) of p-toluenesulfonyl chloride was added and stirring continued overnight. The mixture was added to 10 mL of 10% aqueous sodium bisulfate, then extracted three times with 5 mL each of ethyl acetate. The combined organics were dried ($MgSO_4$), filtered and concentrated in vacuo. The residue and 4.0 g (12.5 mmol) of barium hydroxide in 20 mL of water was heated to 200° C. for 24 hr in a stainless steel high pressure reactor. The mixture was cooled and acidified to pH 7 with 0.7 mL (12.5 mmol) concentrated sulfuric acid. The resulting solid was filtered and washed three times with 10 mL each of 0.25N sodium hydroxide. Cation exchange chromatography of the filtrate afforded a solid that was suspended in water and filtered, washed with water, acetone, and ether and dried in vacuo at 60° C. to afford 0.11 g (14%) of the title compound.

Analysis calculated for $C_{14}H_{15}NO_4Cl_2$: %C, 50.62; %H, 4.55 %N, 4.22. Found: %C, 52.43; %H, 5.19; %N, 4.55.

Field Desorption Mass Spectrum: M=332.

EXAMPLE 76

Preparation of 2SR- and 2RS-2-amino-2-(1SR,2SR-2-carboxycyclopropan-1-yl)-4-(3-biphenyl)butanoic acid A. (1SR,2SR-2-carbethoxycycloprop-1-yl) (2-(3-biphenyl)ethyl) ketone: A solution of 2.8 g (9.0 mmol) of 1-iodo-2-(3-biphenyl)ethane and 1.4 g (22 mmol) of zinc/copper couple in 30 mL of benzene and 4 mL of N,N-dimethylacetamide was stirred for 3 hr at 60° C., then treated with 0.4 g (0.3 mmol) of tetrakis(triphenylphosphine)palladium(0) and heated for 5 min more. The heating bath was removed, 1.6 g (9.0 mmol) of the material from Preparation 1 was added and the mixture stirred at room temperature for 1 hr. The mixture was diluted with 40 mL of ethyl acetate and filtered through diatomaceous earth. The filtrate was washed with 60 mL of 10% aqueous sodium bisulfate, 60 mL of saturated aqueous sodium bicarbonate and 60 mL of saturated aqueous sodium chloride. The organic layer was dried ($MgSO_4$), filtered and concentrated in vacuo. Chromatography (200 g of silica gel, 10% ethyl acetate/hexane) of the residue afforded 1.2 g (41%) of the title compound.

Analysis calculated for $C_{21}H_{22}O_3$: %C, 78.23; %H, 6.88. Found: %C, 78.18; %H, 6.99.

B. 5SR- and 5RS-5-(1SR,2SR-2-carboxycyclopropan-1-yl)-5-(2-(3-biphenyl)ethyl)imidazolidine-2,4-dione: A solution of 1.2 g (3.7 mmol) of the compound from Example 76A in 8 mL of ethanol and 4.1 mL of 1N sodium hydroxide was stirred 2 hr at 55° C., then a solution of 1.2 g (18.6 mmol) of potassium cyanide and 2.6 g (33.6 mmol) of ammonium carbonate in 4 mL of water was added and the mixture heated at 55° C. for 24 hr. The mixture was cooled and added to 100 mL of 10% aqueous sodium bisulfate. The mixture was allowed to stand at room temperature, the resulting solid was filtered and recrystallized from acetone and water to afford 1.5 g (100%) of the title compound.

Analysis calculated for $C_{21}H_2O$ $N_2O_4$: %C, 69.22; %H, 5.53, %N, 7.69. Found: %C, 69.50; %H, 5.55, %N, 7.40.

C. A solution of 1.5 g (3.7 mmol) of the compound from Example 76B and 5.8 g (18.5 mmol) of barium hydroxide in 20 mL of water was heated to 200° C. for 24 hr in a stainless steel high pressure reactor. The mixture was cooled and acidified to pH 7 with 1.0 mL (18 mmol) of concentrated sulfuric acid. The resulting solid was filtered and washed three times with 10 mL each of 0.25N sodium hydroxide. Cation exchange chromatography of the filtrate afforded a solid that was suspended in water and filtered, washed with water and dried in vacuo at 60° C. to afford 0.02 g (2%) of the title compound.

Analysis calculated for $C_{20}H_{21}NO_4 \cdot 0.5\ H_2O$: %C, 68.95; %H, 6.36; %N, 4.02. Found: %C, 69.17; %H, 6.09; %N, 4.36.

Field Desorption Mass Spectrum: M=339.

EXAMPLE 77

Preparation of 2SR- and 2RS-2-amino-2-(1SR,2SR-2-carboxycyclopropan-1-yl)-4-(2,4-difluorophenyl)butanoic acid A. (1SR,2SR-2-carbethoxycycloprop-1-yl) (2-(2,4-difluorophenyl)ethyl) ketone: A solution of 3.6 g (13.5 mmol) of 1-iodo-2-(2,4-difluorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis(triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 70 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried ($MgSO_4$), filtered and concentrated in vacuo. Chromatography (200 g of silica gel, 10% ethyl acetate/hexane) of the residue afforded 2.5 g (62%) of the title compound.

Analysis calculated for $C_{15}H_{16}O_3F_2$: %C, 63.82; %H, 5.71. Found: %C, 63.76; %H, 5.72.

B. 5SR- and 5RS-5-(1SR,2SR-2-carboxycyclopropan-1-yl)-5-(2-(2,4-difluorophenyl)ethyl)imidazolidine-2,4-dione: A solution of 2.3 g (8.1 mmol) of the compound from Example 77A in 18 mL of ethanol and 9.0 mL of 1N sodium hydroxide was stirred 2 hr at 55° C., then a solution of 2.6 g (40.7 mmol) of potassium cyanide and 5.7 g (73 mmol) of ammonium carbonate in 9 mL of water was added and the mixture heated at 55° C. for 24 hr. The mixture was cooled and added to 100 mL of 10% aqueous sodium bisulfate. The resulting mixture was allowed to stand at room temperature, the resulting solid was filtered and recrystallized from acetone and water to afford 2.0 g (76%) of the title compound.

Analysis calculated for $C_{15}H_{14}N_2O_4F_2$: %C, 55.56; %H, 4.35, N, 8.64. Found: %C, 55.71; %H, 4.30, %N, 8.81.

C. A solution of 2.0 g (6.2 mmol) of the compound from Example 77B and 9.7 g (30.8 mmol) of barium hydroxide in 25 mL of water was heated to 200° C. for 24 hr in a stainless steel high pressure reactor. The mixture was cooled and acidified to pH 7 with 1.7 mL (30.8 mmol) of concentrated sulfuric acid. The resulting solid was filtered and washed three times with 10 mL each of 0.25N sodium hydroxide. Cation exchange chromatography of the filtrate afforded a solid that was suspended in water and filtered, washed with water, acetone, and ether and dried in vacuo at 60° C. to afford 0.17 g (10%) of the title compound.

Analysis calculated for $C_{14}H_{15}NO_4F_2$: %C, 56.19; %H, 5.05; %N, 4.68. Found: %C, 55.90; %H, 5.01; %N, 4.90.

Field Desorption Mass Spectrum: M=300.

EXAMPLE 78

Preparation of 2SR- and 2RS-2-amino-2-(1SR,2SR-2-carboxycyclopropan-1-yl)-4-(3,4-difluorophenyl)butanoic acid A. (1SR,2SR-2-carbethoxycycloprop-1-yl) (2-(3,4-difluorophenyl)ethyl) ketone: A solution of 3.6 g (13.5 mmol) of 1-iodo-2-(3,4-difluorophenyl)ethane and 2.0 g (31 mmol) of zinc/copper couple in 66 mL of benzene and 8 mL of N,N-dimethylacetamide was stirred for 3 hr at 60° C., then treated with 0.6 g (0.5 mmol) of tetrakis (triphenylphosphine)palladium(0) and heated for 5 min more. The heating bath was removed, 2.4 g (13.5 mmol) of the material from Preparation 1 was added and the mixture stirred at room temperature for 1 hr. The mixture was diluted with 70 mL of ethyl acetate and filtered through diatomaceous earth. The filtrate was washed with 100 mL of 10% aqueous sodium bisulfate, 100 mL of saturated aqueous sodium bicarbonate and 100 mL of saturated aqueous sodium chloride. The organic layer was dried (MgSO$_4$), filtered and concentrated in vacuo. Chromatography (200 g of silica gel, 10% ethyl acetate/hexane) of the residue afforded 1.6 g (41%) of the title compound.

Analysis calculated for $C_{15}H_{16}O_3F_2$: %C, 63.82; %H, 5.71. Found: %C, 63.98; %H, 5.64.

B. 5SR- and 5RS-5-(1SR,2SR-2-carboxycyclopropan-1-yl)-5-(2-(3,4-difluorophenyl)ethyl)imidazolidine-2,4-dione: A solution of 1.5 g (5.3 mmol) of the compound from Example 78A in 12 mL of ethanol and 6.0 mL of 1N sodium hydroxide was stirred 2 hr at 55° C., then a solution of 1.7 g (26.6 mmol) of potassium cyanide and 3.7 g (47.8 mmol) of ammonium carbonate in 6 mL of water was added and the mixture heated at 55° C. for 24 hr. The mixture was cooled and added to 100 mL of 10% aqueous sodium bisulfate. The resulting mixture was allowed to stand at room temperature, the resulting solid was filtered and recrystallized from acetone and water to afford 1.3 g (78%) of the title compound.

Analysis calculated for $C_{15}H_{14}N_2O_4F_2$: %C, 55.56; %H, 4.35, %N, 8.64. Found: %C, 55.71; %H, 4.40, %N, 8.65.

C. A solution of 1.3 g (4 mmol) of the compound from Example 78B and 6.3 g (20 mmol) of barium hydroxide in 20 mL of water was heated to 200° C. for 24 hr in a stainless steel high pressure reactor. The mixture was cooled and acidified to pH 7 with 1.1 mL (20 mmol) of concentrated sulfuric acid. The resulting solid was filtered and washed three times with 10 mL each of 0.25N sodium hydroxide. Cation exchange chromatography of the filtrate afforded a solid that was suspended in water and filtered, washed with water, acetone, and ether and dried in vacuo at 60° C. to afford 0.48 g (39%) of the title compound.

Analysis calculated for $C_{14}H_{15}NO_4F_2$: %C, 56.19; %H, 5.05; %N, 4.68. Found: %C, 55.92; %H, 5.00; %N, 4.82.

Field Desorption Mass Spectrum: M=299.

EXAMPLE 79

Preparation of 2SR- and 2RS-2-amino-2-(1SR,2SR-2-carboxycyclopropan-1-yl)-4-(3-carboxyphenyl)butanoic acid A. (1SR,2SR-2-carbethoxycycloprop-1-yl) (2-(3-cyanophenyl)ethenyl) ketone: 11.3 mL (11.3 mmol) of 1N sodium bis(trimethylsilyl)amide was added to a solution of 3.0 g (11.3 mmol) of diethyl (1SR,2SR-2-carbethoxycycloprop-1-yl)-2-oxoethylphosphonate in 30 mL of tetrahydrofuran and stirred for 20 min at room temperature. A solution of 1.5 g (11.3 mmol) of 3-cyanobenzaldehyde in 5 mL of tetrahydrofuran was added and the mixture stirred for 3 hr at room temperature. The mixture was added to 60 mL of water and 30 mL of ether, the organic layer was separated and the aqueous layer extracted three times with 25 mL each of ether. The combined organics were dried (MgSO$_4$), filtered and concentrated in vacuo. Chromatography (150 g of silica gel, 25% ethyl acetate/hexane) of the residue afforded 2.7 g (89%) of the title compound.

B. (1SR,2SR-2-carbethoxycycloprop-1-yl) (2-(3-cyanophenyl)ethyl) ketone: A solution of 0.93 g (3.5 mmol) of the compound from Example 79A in 10 mL of ethyl acetate and 0.04 g of 5% palladium on carbon was degassed (brief evacuation under vacuum for about 30 seconds followed by venting to nitrogen the first time and then to hydrogen the subsequent two times) and then stirred 2 hr at room temperature under hydrogen (in a balloon). The mixture was diluted with 10 mL of ethyl acetate, filtered through diatomaceous earth and concentrated in vacuo to afford 1.0 g (88%) of the title compound.

Analysis calculated for $C_{16}H_{17}NO_3$: %C, 70.83; %H, 6.32; %N, 5.16. Found: %C, 70.88; %H, 6.49; %N, 5.20.

C. 5SR- and 5RS-5-(1SR,2SR-2-carboxycyclopropan-1-yl)-5-(2-(3-cyanophenyl)ethyl)imidazolidine-2,4-dione: A solution of 1.0 g (3.7 mmol) of the compound from Example 79B in 8 mL of ethanol and 4.0 mL of 1N sodium hydroxide was stirred 3 hr at 55° C., then a solution of 1.2 g (18.5 mmol) of potassium cyanide and 2.6 g (33.3 mmol) of ammonium carbonate in 4 mL of water was added and the mixture heated at 55° C. for 24 hr. The mixture was cooled and added to 100 mL of 10% aqueous sodium bisulfate. The resulting solution was extracted four times with 30 mL each of ether, then the combined organics were dried (MgSO$_4$), filtered and concentrated in vacuo at 60° C. to afford 0.8 g (69%) of the title compound.

D. A solution of 0.8 g (2.6 mmol) of the compound from Example 79C and 4.1 g (13 mmol) of barium hydroxide in 20 mL of water was heated to 200° C. for 24 hr in a stainless steel high pressure reactor. The mixture was cooled and acidified to pH 7 with 0.7 mL (13 mmol) of concentrated sulfuric acid. The resulting solid was filtered and washed two times with 10 mL each of 0.25N sodium hydroxide. Cation exchange chromatography of the filtrate afforded a solid that was suspended in water and filtered, washed with water, acetone, and ether and dried in vacuo at 60° C. to afford 0.27 g (33%) of the title compound.

Analysis calculated for $C_{15}H_{17}NO_6 \cdot 0.3\ H_2O$: %C, 57.5; %H, 5.68 %N, 4.47. Found: %C, 57.56; %H, 5.68; %N, 4.06.

Field Desorption Mass Spectrum: M+1=308.

EXAMPLE 80

Preparation of 2SR- and 2RS-2-amino-2-(1SR,2SR-2-carboxycyclopropan-1-yl)-4-(4-carboxyphenyl) butanoic acid A. (1SR,2SR-2-carbethoxycycloprop-1-yl) (2-(4-cyanophenyl)ethenyl) ketone: 11.3 mL (11.3 mmol) of 1N sodium bis(trimethylsilyl)amide was added to a solution of 3.0 g (11.3 mmol) of diethyl (1SR,2SR-2-carbethoxycycloprop-1-yl)-2-oxoethylphosphonate in 30 mL of tetrahydrofuran and stirred for 20 min at room temperature. A solution of 1.5 g (11.3 mmol) of 3-cyanobenzaldehyde in 5 mL of tetrahydrofuran was added and the mixture stirred for 3 hr at room temperature. The mixture was added to 60 mL of water and 30 mL of ether, the organic layer was separated and the aqueous layer extracted three times with 25 mL each of ether. The combined organics were dried (MgSO$_4$), filtered and concentrated in vacuo. Chromatography (150 g of silica gel, 25% ethyl acetate/hexane) of the residue afforded 1.5 g (49%) of the title compound.

B. (1SR,2SR-2-carbethoxycycloprop-1-yl) (2-(4-cyanophenyl)ethyl) ketone: A solution of 1.47 g (5.5 mmol) of the compound from Example 80A in 40 mL of ethyl acetate and 0.07 g of 5% palladium on carbon was degassed (brief evacuation under vacuum for about 30 seconds followed by venting to nitrogen the first time and then to hydrogen the subsequent two times) and then stirred 4 hr at room temperature under hydrogen (in a balloon). The mixture was diluted with 10 mL of ethyl acetate and filtered through diatomaceous earth and concentrated in vacuo to afford 1.4 g (94%) of the title compound.

Analysis calculated for $C_{16}H_{17}NO_3$: %C, 70.83; %H, 6.32; %N, 5.16. Found: %C, 70.77; %H, 6.53; %N, 5.18.

C. 5SR- and 5RS-5-(1SR,2SR-2-carboxycyclopropan-1-yl)-5-(2-(4-cyanophenyl)ethyl)imidazolidine-2,4-dione: A solution of 1.4 g (5.2 mmol) of the compound from Example 80B in 11 mL of ethanol and 5.7 mL of 1N sodium hydroxide was stirred 3 hr at 55° C., then a solution of 1.7 g (26 mmol) of potassium cyanide and 3.6 g (46.8 mmol) of ammonium carbonate in 6 mL of water was added and the mixture heated at 55° C. for 24 hr. The mixture was cooled and added to 100 mL of 10% aqueous sodium bisulfate. The mixture was allowed to stand at room temperature, then the resulting solid was filtered and washed with water to afford 1.2 g (72%) of the title compound.

D. A solution of 1.18 g (3.8 mmol) of the compound from Example 80C and 5.9 g (19 mmol) of barium hydroxide in 25 mL of water was heated to 200° C. for 24 hr in a stainless steel high pressure reactor. The mixture was cooled and acidified to pH 7 with 1 mL (18 mmol) of concentrated sulfuric acid. The resulting solid was filtered and washed two times with 10 mL each of 0.25N sodium hydroxide. Cation exchange chromatography of the filtrate afforded a solid that was suspended in water and filtered, washed with water, acetone, and ether and dried in vacuo at 60° C. to afford 0.3 g (26%) of the title compound.

Analysis calculated for $C_{15}H_{17}NO_6$: %C, 58.63; %H, 5.58 %N, 4.56. Found: %C, 58.48; %H, 5.59; %N, 4.60.

Field Desorption Mass Spectrum: M+1=308.

EXAMPLE 81

Preparation of 2SR- and 2RS-2-amino-2-(1SR,2SR-2-carboxycyclopropan-1-yl)-4-(3-fluorophenyl)butanoic acid A. (1SR,2SR-2-carbethoxycycloprop-1-yl) (2-(3-fluorophenyl)ethenyl) ketone: A solution of 2.0 g (7.6 mmol) of dimethyl(1SR,2SR-2-carbethoxycycloprop-1-yl)-2-oxoethylphosphonate in 5 mL of tetrahydrofuran was added to a suspension of 0.3 g (8.0 mmol) sodium hydride in 5 mL dry tetrahydrofuran, and the mixture was stirred for 25 min at room temperature. 1.0 g (8.3 mmol) of 3-fluorobenzaldehyde was added and the mixture stirred for 1 hr. The mixture was diluted with 20 mL of water and extracted three times with 15 mL each of ether. The combined organics were dried (MgSO$_4$), filtered and concentrated in vacuo to afford 1.8 g (91%) of the title compound.

B. (1SR,2SR-2-carbethoxycycloprop-1-yl) (2-(3-fluorophenyl)ethyl) ketone: A solution of 1.80 g (6.86 mmol) of the compound from Example 81A in 50 mL of ethanol and 0.1 g of 5% palladium on carbon was degassed (brief evacuation under vacuum for about 30 seconds followed by venting to nitrogen the first time and then to hydrogen the subsequent two times) and then stirred 16 hrs at room temperature under hydrogen (in a balloon). The mixture was filtered through diatomaceous earth and concentrated in vacuo. Chromatography (100 g of silica gel, 20% ethyl acetate/hexane) of the residue afforded 1.5 g (83%) of the title compound.

C. (1SR,2SR-2-carboxycycloprop-1-yl) (2-(3-fluorophenyl)ethyl) ketone: A solution of 1.5 g (5.6 mmol) of the compound from Example 81B in 20 mL of ethanol and 6.2 mL of 1N sodium hydroxide was stirred 24 hr at room temperature, then concentrated in vacuo. The residue was dissolved in 40 mL of 10% aqueous sodium bisulfate and extracted four times with 20 mL each of ethyl acetate, then the combined organics were dried (MgSO$_4$), filtered and concentrated in vacuo at 50° C. to afford 1.2 g (92%) of the title compound.

D. 5SR- and 5RS-5-(1SR,2SR-2-carboxycyclopropan-1-yl)-5-(2-(3-fluorophenyl)ethyl)imidazolidine-2,4-dione: A solution of 1.2 g (5.2 mmol) of the compound from Example 81C in 10 mL of ethanol was added to a solution of 1.7 g (26.1 mmol) of potassium cyanide and 4.5 g (46.9 mmol) of ammonium carbonate in 10 mL of water, then this mixture was heated to 55° C. for 96 hr. The mixture was cooled and added to 125 mL of 10% aqueous sodium bisulfate. The resulting solid was filtered, washed three times with water and recrystallized from acetone and water to afford 1.2 g (75%) of the title compound.

Analysis calculated for $C_{15}H_{15}N_2O_4F \cdot 0.25\ H_2O$: %C, 57.97; %H, 5.03; %N, 9.01. Found: %C, 58.13; %H, 5.03; %N, 9.06.

Field Desorption Mass Spectrum: M=306.

E. A solution of 1.19 g (3.9 mmol) of the compound from Example 81D and 6.1 g (19.5 mmol) of barium hydroxide in 25 mL of water was heated to 200° C. for 24 hr in a stainless steel high pressure reactor. The mixture was cooled and acidified to pH 2 with concentrated sulfuric acid. The resulting solution was filtered and the solid washed two times with 25 mL each of 0.2N sodium hydroxide, one time with 20 mL of water, one time with 10 mL of 1N sodium hydroxide then two times with 10 mL of water. The filtrate was adjusted to pH 3 with 5N hydrochloric acid. Cation exchange chromatography of the filtrate afforded a solid that was suspended in water, filtered and rinsed with H$_2$O , acetone then ether. Drying in vacuo at 60° C. to afforded 0.43 g (40%) of the title compound.

Analysis calculated for $C_{14}H_{16}NO_4F$: %C, 59.78; %H, 5.73 %N, 4.98. Found: %C, 59.58; %H, 5.68; %N, 4.72.

Field Desorption Mass Spectrum: M+1=282.

EXAMPLE 82

Preparation of 2SR- and 2RS-2-amino-2-(1SR,2SR-2-carboxycyclopropan-1-yl)-4-(4-bromophenyl) butanoic acid A. (1SR,2SR-2-carbethoxycycloprop-1-yl) (2-(4-bromophenyl)ethyl) ketone: A solution of 5.3 g (17 mmol) of 1-iodo-2-(4-bromophenyl)ethane and 2.1 g (32.7 mmol) of zinc/copper couple in 47 mL of benzene and 4.7 mL of N,N-dimethylacetamide was stirred for 2 hr at 60° C. The heating bath was removed, then the mixture treated with 0.32 g (0.28 mmol) of tetrakis(triphenylphosphine) palladium(0). 2.5 g (14.2 mmol) of the material from Preparation 1 was added and the mixture stirred at room temperature for 1.5 hr. The mixture was diluted with 50 mL of ethyl acetate and filtered through diatomaceous earth. The filtrate was washed with 50 mL of 1N hydrochloric acid, 50 mL of saturated aqueous sodium bicarbonate and 50 mL of saturated aqueous sodium chloride. The organic layer was dried (MgSO$_4$), filtered and concentrated in vacuo. Chromatography (150g of silica gel, 10% ethyl acetate/hexane) of the residue afforded 1.8 g (38%) of the title compound.

B. (1SR,2SR-2-carboxycycloprop-1-yl) (2-(4-bromophenyl)ethyl) ketone: A solution of 1.8 g (5.4 mmol) of the compound from Example 82A in 20 mL of ethanol and 6.0 mL of 1N sodium hydroxide was stirred 24 hr at room temperature, then concentrated in vacuo. The residue was dissolved in 50 mL of 10% sodium bisulfate and extracted four times with 25 mL each of ethyl acetate, then the combined organics were dried (MgSO$_4$), filtered and concentrated in vacuo to afford 1.5 g (94%) of the title compound.

C. 5SR- and 5RS-5-(1SR,2SR-2-carboxycyclopropan-1-yl)-5-(2-(4-bromophenyl)ethyl)imidazolidine-2,4-dione: A solution of 1.5 g (5.1 mmol) of the compound from Example 82B in 7.5 mL of ethanol was added to a solution of 1.7 g (25.6 mmol) of potassium cyanide and 4.4 g (46.0 mmol) of ammonium carbonate in 7.5 mL of water, then this mixture was heated to 55° C. for 24 hr. The mixture was cooled and added to 150 mL of 10% sodium bisulfate, and the resulting precipitate was filtered and washed three times with water. Drying in vacuo at 60° C. afforded 1.6 g (83%) of the title compound.

Analysis calculated for $C_{15}H_{15}N_2O_4Br$: %C, 49.07; %H, 4.12; %N, 7.63. Found: %C, 49.24; %H, 4.37; %N, 7.38.

Field Desorption Mass Spectrum: M+1=368.

D. A solution of 1.6 g (4.3 mmol) of the compound from Example 82C and 6.7 g (21.3 mmol) of barium hydroxide in 30 mL of water was heated to 250° C. for 16 hr in a stainless steel high pressure reactor. The mixture was cooled and acidified to pH 2 with concentrated sulfuric acid, affording a solid that was filtered then rinsed two times with 10 ml of hot 10% aqueous pyridine. Cation exchange chromatography of the filtrate afforded a solid that was dissolved in water and concentrated in vacuo two times. The residue was recrystallized from glacial acetic acid, and the resulting solid was dried in vacuo at 60° C. to afford 25 mg (2%) of the title compound.

Analysis calculated for $C_{14}H_{16}NO_4Br$: %C, 49.14; %H, 4.71; %N, 4.09. Found: %C, 53.55; %H, 5.29; %N, 3.84.

Field Desorption Mass Spectrum: M+2=344.

EXAMPLE 83

Preparation of 2SR- and 2RS-2-amino-2-(1SR,2SR-2-carboxycyclopropan-1-yl)-4-(9-bicyclo[3.3.1]nonanyl) butanoic acid A. (1SR,2SR-2-carbethoxycycloprop-1-yl) (2-(9-bicyclo[3.3.1]nonanyl)ethenyl) ketone: A solution of 2.5 g (9.5 mmol) of dimethyl(1SR,2SR-2-carbethoxycycloprop-1-yl)-2-oxoethylphosphonate in 5 mL of tetrahydrofuran was added to a suspension of 0.4 g (9.9 mmol) sodium hydride in 5 mL of tetrahydrofuran, and the mixture was stirred for 20 min at room temperature. 1.6 g (10.4 mmol) of bicyclo[3.3.1]nonan-9-one in 7 mL of tetrahydrofuran was added and the mixture stirred for 1 hr. The mixture was diluted with 20 mL of water and extracted three times with 15 mL each of ether. The combined organics were dried (MgSO$_4$), filtered and concentrated in vacuo to afford 2.4 g (87%) of the title compound.

B. (1SR,2SR-2-carbethoxycycloprop-1-yl) (2-(9-bicyclo[3.3.1]nonanyl)ethyl) ketone: A solution of 2.4 g (8.3 mmol) of the compound from Example 83A in 50 mL of ethanol and 0.1 g of 5% palladium on carbon was degassed (brief evacuation under vacuum for about 30 seconds followed by venting to nitrogen the first time and then to hydrogen the subsequent two times) and then stirred 16 hrs at room temperature under hydrogen (in a balloon). The mixture was filtered through diatomaceous earth and concentrated in vacuo. The residue was dissolved in 50 mL of ethanol and 0.1 g of 10% palladium on carbon was added. The mixture was stirred under a hydrogen atmosphere (balloon) for 5 hr, then diluted with 30 mL of ethyl acetate, filtered through diatomaceous earth and concentrated in vacuo. Chromatography (125 g of silica gel, 5% ethyl acetate/hexane) of the residue afforded 1.5 g (62%) of the title compound.

Analysis calculated for $C_{18}H_{28}O_3$: %C, 73.93; %H, 9.65. Found: %C, 73.69; %H, 9.41.

Field Desorption Mass Spectrum: M=292.

C. 5SR- and 5RS-5-(1SR,2SR-2-carboxycyclopropan-1-yl)-5-(2-(9-bicyclo[3.3.1]nonanyl)ethyl)imidazolidine-2,4-dione: A solution of 1.5 g (5.1mmol) of the compound from Example 83B in 20 mL of ethanol and 5.6 mL of 1N sodium hydroxide was stirred 3 hr at 60° C., then cooled and concentrated in vacuo. To the residue was added 1.7 g (25.3 mmol) of potassium cyanide, 4.4 g (45.5 mmol) of ammonium carbonate, 10 mL of water and 10 mL of ethanol. The mixture was heated to 55 C. for 16 hr then cooled and added to 125 mL of 10% aqueous sodium bisulfate. The resulting solid was filtered, washed three times with water and recrystallized from acetone and water then dried in vacuo at 60° C. to afford 1.6 g (92%) of the title compound.

Analysis calculated for $C_{18}H_{26}N_2O_4 \cdot 0.3H_2O$: %C, 63.62; %H, 7.89; %N, 8.24. Found: %C, 64.00; %H, 7.63; %N, 7.84.

Field Desorption Mass Spectrum: M=334.

D. A solution of 1.6 g (4.6 mmol) of the compound from Example 83C and 7.3 g (23.2 mmol) of barium hydroxide in 30 mL of water was heated to 200° C. for 24 hr in a stainless steel high pressure reactor. The mixture was cooled and acidified to pH 2 with concentrated sulfuric acid. The resulting solution was filtered and the solid washed two times with 10 mL each of 1N sodium hydroxide and two times with 20 mL each of water. The filtrate was adjusted to pH 3 with 5N hydrochloric acid. Cation exchange chromatography of the filtrate afforded a solid that was suspended in water and concentrated in vacuo. The residue was suspended in acetone, filtered and rinsed with acetone then ether. Drying in vacuo at 60° C. to afforded 0.27 g (18%) of the title compound.

Analysis calculated for $C_{17}H_{27}NO_4$: %C, 65.99; %H, 8.80 %N, 4.53. Found: %C, 61.73; %H, 8.41; %N, 4.57.

Field Desorption Mass Spectrum: M+1=310.

EXAMPLE 84

Preparation of 2SR- and 2RS-2-amino-2-(1SR,2SR-2-carboxycyclopropan-1-yl)-4-(2-phenoxyphenyl)butanoic acid A. (1SR,2SR-2-carbethoxycycloprop-1-yl) (2-(2-phenoxyphenyl)ethenyl) ketone: A solution of 2.0 g (7.6 mmol) of dimethyl(1SR,2SR-2-carbethoxycycloprop-1-yl)-2-oxoethylphosphonate in 5 mL of tetrahydrofuran was added to a suspension of 0.3 g (8.0 mmol) sodium hydride in 5 mL of tetrahydrofuran, and the mixture was stirred for 20 min at room temperature. A solution of 2-phenoxybenzaldehyde in 5 mL of tetrahydrofuran was added and the mixture stirred for 1.5 hr at room temperature. The mixture was diluted with 15 mL of water and extracted three times with 10 mL each of ether. The combined organics were dried (MgSO$_4$), filtered and concentrated in vacuo to afford 2.2 g (86%) of the title compound.

B. (1SR,2SR-2-carbethoxycycloprop-1-yl) (2-(2-phenoxyphenyl)ethyl) ketone: A solution of 2.2 g (6.5 mmol) of the compound from Example 84A in 50 mL of ethanol and 0.1 g of 5% palladium on carbon was degassed (brief evacuation under vacuum for about 30 seconds followed by venting to nitrogen the first time and then to hydrogen the subsequent two times) and then stirred 3.5 hr at room temperature under hydrogen (in a balloon). The mixture was diluted with 50 mL of ethyl acetate and filtered through diatomaceous earth and concentrated in vacuo. Chromatography (125 g of silica gel, 15% ethyl acetate/hexane) of the residue afforded 1.8 g (83%) of the title compound.

Analysis calculated for $C_{21}H_{22}O_4$: %C, 74.54; %H, 6.55. Found: %C, 74.54; %H, 6.55.

Field Desorption Mass Spectrum: M=338.

C. 5SR- and 5RS-5-(1SR,2SR-2-carboxycyclopropan-1-yl)-5-(2-(2-phenoxyphenyl)ethyl)imidazolidine-2,4-dione: A solution of 1.8 g (5.4mmol) of the compound from Example 84B in 20 mL of ethanol and 5.9 mL of 1N sodium hydroxide was stirred 3 hr at 60° C., then cooled and concentrated in vacuo. To the residue was added 1.8 g (26.9 mmol) of potassium cyanide, 4.7 g (48.4 mmol) of ammonium carbonate, 10 mL of water and 10 mL of ethanol. The mixture was heated to 55° C. for 16 hr then cooled and added to 125 mL of 10% aqueous sodium bisulfate. The aqueous mixture was extracted four times with ethyl acetate. The combined organics were dried over magnesium sulfate, filtered and concentrated in vacuo. The residue was recrystallized from acetone and water then dried in vacuo at 60° C. to afford 1.8 g (86%) of the title compound.

Analysis calculated for $C_{21}H_2O\ N_2O_5 \cdot 0.4\ H_2O$: %C, 65.07; %H, 5.41; %N, 7.23. Found: %C, 65.30; %H, 5.20; %N, 6.84.

Field Desorption Mass Spectrum: M=380.

D. A solution of 1.8 g (4.6 mmol) of the compound from Example 84C and 7.3 g (23.1 mmol) of barium hydroxide in 30 mL of water was heated to 200° C. for 24 hr in a stainless steel high pressure reactor. The mixture was cooled and acidified to pH 2 with 4N sulfuric acid. The mixture was then filtered through diatomaceous earth and rinsed two times with 10 mL each of 1N sodium hydroxide and two times with 10 mL each of H$_2$O. The filtrate was adjusted to pH 3 with 5N hydrochloric acid. Cation exchange chromatography of the filtrate afforded a solid that was suspended in water and filtered, washed with water, acetone, and ether and dried in vacuo at 60° C. to afford 0.7 g (41%) of the title compound.

Analysis calculated for $C_{20}H_{21}NO_5$: %C,67.59; %H, 5.96; %N, 3.94. Found: %C, 67.33; %H, 5.98; %N, 4.11.

Field Desorption Mass Spectrum: M+1=356.

We claim:

1. A compound of formula

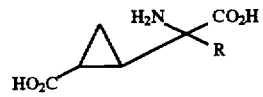

I in which

R represents a group of formula —L—Q in which

L represents a bond or a diradical of formula —(CH$_2$)$_m$(Z$^1$)$_p$(CH$_2$)$_n$— in which m is 1 to 10;

p is 0 or 1;

n is 0 to 6; and

Z$^1$ is oxygen, sulphur or a group of formula NR$^a$ in which R$^a$ represents hydrogen, (1–6C)alkyl or phenyl(1–3C)alkyl; and Q is hydrogen, an unsubstituted or substituted heteroaromatic group, an unsubstituted or substituted aromatic group, a non-aromatic carbocyclic group, a non-aromatic heterocyclic group, or a non-aromatic monocyclic carbocyclic group fused with one or two monocyclic aromatic or heteroaromatic groups, a non-aromatic monocyclic heterocyclic group fused with one or two monocyclic aromatic or heteroaromatic groups; or a group of formula —C(R$^1$R$^2$R$^3$)

in which R$^1$ represents (1–6C)alkyl, an unsubstituted or substituted heteroaromatic group, an unsubstituted or substituted aromatic group, a non-aromatic carbocyclic group, a non-aromatic heterocyclic group, a non-aromatic monocyclic carbocyclic group fused with one or two monocyclic aromatic or heteroaromatic groups, or a non-aromatic monocyclic heterocyclic group fused with one or two monocyclic aromatic or heteroaromatic groups;

one or both of R$^2$ and R$^3$ is as defined for R$^1$ or represents a group of formula —Z$^2$—R$^4$ in which Z$^2$ represents a bond, O, S, CH$_2$ or —NR$^b$— in which R$^b$ represents hydrogen, (1–6C) alkyl or phenyl(1–3C)alkyl, and R$^4$ represents an unsubstituted or substituted heteroaromatic group or an unsubstituted or substituted aromatic group;

and the other of R$^2$ and R$^3$, if any, represents hydrogen;

provided that when Q represents hydrogen, L does not represent a bond or methylene;

or a pharmaceutically acceptable metabolically labile ester or amide thereof;

or a pharmaceutically acceptable salt thereof.

2. A compound as claimed in claim 1, in which Q is hydrogen; a phenyl, naphthyl, furyl, thiophenyl, oxazolyl, isoxazolyl, thiazoyl, isothiazolyl, imidazolyl, benzofuryl, benzothiophenyl, benzimidazolyl, benzoxazolyl, benzothiazolyl or indolyl group unsubstituted or substituted with amino, hydroxy, nitro, halogeno, (1–6C) alkyl, (1–6C) alkoxy, carboxy, (1–6C) alkoxycarbonyl, carbamoyl, (1–6C) alkanoylamino, (1–6C)alkylsulphonyl, (1–6C) alkylsulphonylamino, phenyl, phenoxy, phenylthio, phenylsulphonyl, phenylsulphonylamino, toluenesulphonylamino or (1–6C)-fluoroalkyl; (3–10C)cycloalkyl; 1-adamantyl, 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl, and bicyclo[3,3,1]non-1-yl,-2yl,-3yl or -9yl; azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl; indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, - 5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl; 2,3-dihydrobenzopyran-2-yl, -3-yl or -4-yl, xanthen-9-yl, 1,2,3,4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl; or a group of formula —C(R$^1$,R$^2$,R$^3$)

in which R$^1$ represents (1–6C)alkyl; a phenyl, naphthyl, furyl, thiophenyl, oxazolyl, isoxazolyl, thiazoyl, isothiazolyl, imidazolyl, benzofuryl, benzothiophenyl, benzimidazolyl, benzoxazolyl, benzothiazolyl or indolyl group unsubstituted or substituted with amino, hydroxy, nitro, halogeno, (1–6C) alkyl, (1–6C) alkoxy, carboxy, (1–6C) alkoxycarbonyl, carbamoyl, (1–6C) alkanoylamino, (1–6C)alkylsulphonyl, (1–6C) alkylsulphonylamino, phenyl, phenoxy, phenylthio, phenylsulphonyl, phenylsulphonylamino, toluenesulphonylamino or (1–6C)fluoroalkyl; (3–10C) cycloalkyl; 1-adamantyl, 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl and bicyclo[3,3,1]non-1-yl,-2-yl,-3-yl or -9-yl; azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl; indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, -5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl; 2,3-dihydrobenzopyran-2-yl, -3-yl or -4-yl, xanthen-9-yl, 1,2,3,4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl;

one or both of R$^2$ and R$^3$ is as defined for R$^1$ or represents a group of formula —Z$^2$—R$^4$ in which Z$^2$ represents a bond, O, S, CH$_2$ or —NR$^b$— in which R$^b$ represents hydrogen, (1–6C) alkyl or phenyl(1–3C)alkyl, and R$^4$ represents a phenyl, naphthyl, furyl, thiophenyl, oxazolyl, isoxazolyl, thiazoyl, isothiazolyl, imidazolyl, benzofuryl, benzothiophenyl, benzimidazolyl, benzoxazolyl, benzothiazolyl or indolyl group unsubstituted or substituted with amino, hydroxy, nitro, halogeno, (1–6C) alkyl, (1–6C) alkoxy, carboxy, (1–6C) alkoxycarbonyl, carbamoyl, (1–6C) alkanoylamino, (1–6C)alkylsulphonyl, (1–6C) alkylsulphonylamino, phenyl, phenoxy, phenylthio, phenylsulphonyl, phenylsulphonylamino, toluenesulphonylamino or (1–6C)fluoroalkyl;

and the other of R$^2$ and R$^3$, if any represents hydrogen.

3. A compound as claimed in claim 2, in which Q is hydrogen; 1-methylindol-3-yl; 2-thiophenyl; 3-thiophenyl; naphth-1-yl-; naphth-2-yl; phenyl which is unsubstituted or substituted by one or two of hydroxy, halogeno, (1–6C) alkyl, (1–6C)alkoxy, carboxy, phenyl, phenoxy or (1–6C) fluoroalkyl; pentafluorophenyl; cyclobutyl; cyclopentyl; cyclohexyl; 1-adamantyl; piperidin-4-yl; indan-2-yl; xanthen-9-yl; isopropyl; 1-phenylethyl; dibenzylmethyl, diphenylmethyl or di-(4-chlorophenyl)methyl.

4. A compound as claimed in claim 3, in which Q is hydrogen, 1-methylindol-3-yl, 2-thiophenyl, 3-thiophenyl, 1-naphthyl, 2-naphthyl, phenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4-dichlorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluoromethyl, 2-fluoro-5-trifluoromethylphenyl, 2-phenoxyphenyl, 3-phenoxyphenyl, 3-carboxyphenyl, 4-carboxyphenyl, cyclobutyl, cyclopentyl, cyclohexyl, 1-adamantyl, piperidin-4-yl, indan-2-yl, xanthen-9-yl, bicyclo[3,3,1]non-9-yl, isopropyl, 1-phenylethyl, dibenzylmethyl, diphenylmethyl or di-(4-chlorophenyl)methyl.

5. A compound as claimed in claim 4, in which Q is 3-methylphenyl, diphenylmethyl, xanthen-9-yl, 4-fluorophenyl, 3,5-dichlorophenyl, or 3,4-difluorophenyl.

6. A compound as claimed in any one of claims 1 to 5, in which m is 1, 2, 3, 4, 5, or 6;

p is 0 or 1;

n is 0; and

Z$^1$ is O, S or NH.

7. A compound as claimed in any one of claims 1 to 5, in which L is a bond, methylene, ethylene, propylene, butylene, pentylene or methyleneoxy.

8. A compound as claimed in claim 1 in which R represents (dibenzopyran-4-yl)methyl, (2,2-diphenyl)ethyl, 2-(3-methylphenyl)ethyl, 2-(4-fluorophenyl)ethyl, 2-(3,5-dichlorophenyl)ethyl or 2-(3,4-difluorophenyl)ethyl.

9. A compound as claimed in claim 1, which is in the S,S,S configuration.

10. A compound as claimed in claim 1, which is selected from 2SR- and 2RS-2-amino-2-(1SR,2SR-2-carboxycyclopropan-1-yl)-3-(dibenzopyran-4-yl)propanoic acid; 2S-2-amino-2-(1S,2S-2-carboxycyclopropan-1-yl)-4-(3-methylphenyl)butanoic acid; 2S-2-amino-2-(1S,2S-2-carboxycyclopropan-1-yl)-3-(dibenzopyran-4-yl)propanoic acid; 2SR- and 2RS-2-amino-2-(1SR,2SR-2-carboxycyclopropan-1-yl -4-(4-fluorophenyl)butanoic acid; 2SR- and 2RS-2-amino-2-(1SR,2SR-2-carboxycyclopropan-1-yl -4-(3,5-dichlorophenyl)butanoic acid; 2S-2-amino-2-(1S,2S-2-carboxycyclopropan-1-yl)-4,4-diphenylbutanoic acid; 2SR- and 2RS-2-amino-2-(1SR,2SR-2-carboxycyclopropan-1-yl)-4-(3,4-difluorophenyl) butanoic acid; 2SR- and 2RS-2-amino-2-(1SR,2SR-2-carboxycyclopropan-1-yl)-4-(3,4-dichlorophenyl)butanoic acid; 2SR- and 2RS-2-amino-2-(1SR,2SR-2- carboxycyclopropan-1-yl)-4-(3-methylphenyl)butanoic acid; 2SR- and 2RS-2-amino-2-(1SR,2SR-2-carboxycyclopropan-1-yl)-4-(3-methoxyphenyl)butanoic acid; 2SR- and 2RS-2-amino-2-(1SR,2SR-2-carboxycyclopropan-1-yl)-4-(3-carboxyphenyl)butanoic acid; 2SR- and 2RS-2-amino-2-(1SR,2SR-2-carboxycyclopropan-1-yl)-4-(3-bromophenyl)butanoic acid; 2SR- and 2RS-2-amino-2-(1SR,2SR-2-carboxycyclopropan-1-yl)-4-(2,4-difluorophenyl)butanoic acid; 2SR- and 2RS-2-amino-2-(1SR,2SR-2-carboxycyclopropan-1-yl)-4-(3-(trifluoromethyl)phenyl) butanoic acid; 2SR- and 2RS-2-amino-2-(1SR,2SR-2-carboxycyclopropan-1-yl)-4,4-diphenylbutanoic acid; 2SR- and 2RS-2-amino-2-(1SR,2SR-2-carboxycyclopropan-1-yl)-4,4-di(4,4'-dichloro)phenylbutanoic acid; 2SR- and 2RS-2-amino-2-(1SR,2SR-2-carboxycyclopropan-1-yl)-4-(3-hydroxyphenyl)butanoic acid; 2SR- and 2RS-2-amino-2-(1SR,2SR-2-carboxycyclopropan-1-yl)-4-(3,5-dimethoxyphenyl)butanoic acid; 2SR- and 2RS-2-amino-2-(1SR,2SR-2-carboxycyclopropan-1-yl)-4-(2-hydroxyphenyl)butanoic acid; and 2SR- and 2RS-2-amino-2-(1SR,2SR-2-carboxycyclopropan-1-yl)-4-(3-fluorophenyl)butanoic acid.

11. A process for the preparation of a compound of formula I, or a pharmaceutically acceptable metabolically labile ester or amide thereof, or a pharmaceutically acceptable salt thereof, as defined in claim 1, which comprises (a) hydrolyzing a compound of formula

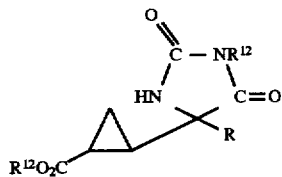

II or (b) deprotecting a compound of formula

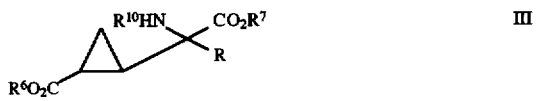

III in which $R^{12}$ represents a hydrogen atom, a (1–4C) alkyl group, a phenyl (1–4C)alkyl group in which the phenyl group is unsubstituted or substituted by halogeno, (1–4C)alkyl or (1–4C)alkoxy; one or both of $R^6$ and $R^7$ represents a carboxyl protecting group, and the other of $R^6$ and $R^7$, if any, represents hydrogen; and $R^{10}$ represents an amine protecting group.

12. A pharmaceutical composition, which comprises an effective amount of a compound as claimed in claim 1 and a pharmaceutically acceptable diluent or carrier.

13. A method of antagonizing one or more of the actions of L-glutamate at L-glutamate metabotropic receptors in a warm blooded animal requiring such treatment, which comprises administering to said animal an effective amount of a compound as claimed in claim 1.

14. A method of treating psychosis, which comprises administering to a mammal in need of treatment an effective amount of a compound as claimed in claim 1.

* * * * *